US012151058B2

(12) United States Patent
Savastano et al.

(10) Patent No.: US 12,151,058 B2
(45) Date of Patent: Nov. 26, 2024

(54) SYSTEMS, DEVICES, AND METHODS FOR ACCESSING A SUBDURAL SPACE

(71) Applicant: Mayo Foundation for Medical Education and Research, Rochester, MN (US)

(72) Inventors: Luis E. Savastano, Hillsborough, CA (US); Yang Liu, Shanghai (CN)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/469,376

(22) Filed: Sep. 18, 2023

(65) Prior Publication Data
US 2024/0148959 A1 May 9, 2024

Related U.S. Application Data

(60) Provisional application No. 63/422,799, filed on Nov. 4, 2022.

(51) Int. Cl.
*A61B 18/24* (2006.01)
*A61B 18/14* (2006.01)
(Continued)

(52) U.S. Cl.
CPC ........... *A61M 1/84* (2021.05); *A61B 18/1487* (2013.01); *A61B 2018/00565* (2013.01);
(Continued)

(58) Field of Classification Search
CPC ......... A61B 2018/00434; A61B 2018/00446; A61B 2018/00404; A61B 2018/0041;
(Continued)

(56) References Cited

U.S. PATENT DOCUMENTS

| 6,726,677 B1 | 4/2004 | Flaherty et al. |
| 7,134,438 B2 | 11/2006 | Makower et al. |

(Continued)

FOREIGN PATENT DOCUMENTS

| AU | 2020265573 A1 | 11/2021 |
| WO | WO-2015179324 A2 | 11/2015 |

(Continued)

OTHER PUBLICATIONS

Co-pending U.S. Appl. No. 18/469,437, inventors Savastano; Luis E. et al., filed Sep. 18, 2023.

(Continued)

*Primary Examiner* — Deanna K Hall
(74) *Attorney, Agent, or Firm* — COOLEY LLP

(57) ABSTRACT

Disclosed herein are systems, devices, and methods for accessing a subdural space. In some embodiments, an apparatus may comprise a shaft configured to be slidably disposed within a lumen of a catheter. The shaft may be configured to be advanced distally from a distal end of the catheter and into a blood vessel of a subject. The shaft may include a perforating tip including an energy element configured to generate radiofrequency energy to form an opening through a wall of the blood vessel and dura of the subject and into an extravascular space of the subject. A curved section may be configured to be radially constrained within the lumen of the catheter and to curve toward the wall of the blood vessel and the dura upon exiting the lumen of the catheter such that the energy element is positioned to form the opening.

25 Claims, 42 Drawing Sheets
(34 of 42 Drawing Sheet(s) Filed in Color)

(51) Int. Cl.
*A61M 1/00* (2006.01)
*A61B 18/00* (2006.01)

(52) U.S. Cl.
CPC .............. *A61B 2018/00601* (2013.01); *A61B 2218/007* (2013.01); *A61M 2205/32* (2013.01); *A61M 2210/005* (2013.01); *A61M 2210/0687* (2013.01)

(58) Field of Classification Search
CPC ...... A61B 2018/00416; A61B 18/1487; A61B 2018/00565; A61B 2218/007; A61B 2018/00601; A61M 1/84; A61M 2205/32; A61M 2210/005; A61M 2210/06; A61M 2210/0687; A61M 2210/0693
See application file for complete search history.

(56) References Cited

U.S. PATENT DOCUMENTS

| | | |
|---|---|---|
| 7,141,041 B2 | 11/2006 | Seward |
| 8,663,304 B2 | 3/2014 | Wallace et al. |
| 9,211,163 B1 | 12/2015 | Jaramaz et al. |
| 9,585,692 B2 | 3/2017 | Kurth et al. |
| 2002/0169377 A1 | 11/2002 | Khairkhahan et al. |
| 2003/0014016 A1* | 1/2003 | Purdy .................. A61B 10/02 604/9 |
| 2003/0181807 A1 | 9/2003 | Murphy et al. |
| 2004/0186368 A1 | 9/2004 | Ramzipoor et al. |
| 2005/0043673 A1 | 2/2005 | Lieberman |
| 2005/0148880 A1 | 7/2005 | Tower |
| 2005/0240205 A1 | 10/2005 | Berg et al. |
| 2006/0095066 A1 | 5/2006 | Chang et al. |
| 2007/0219471 A1 | 9/2007 | Johnson et al. |
| 2010/0217276 A1 | 8/2010 | Garrison et al. |
| 2011/0087261 A1 | 4/2011 | Wittkampf et al. |
| 2011/0238083 A1 | 9/2011 | Moll et al. |
| 2012/0059285 A1 | 3/2012 | Soltani et al. |
| 2012/0330196 A1 | 12/2012 | Nita |
| 2014/0324080 A1 | 10/2014 | Wallace |
| 2014/0343348 A1 | 11/2014 | Kaplan et al. |
| 2015/0196741 A1 | 7/2015 | Heilman et al. |
| 2016/0136398 A1 | 5/2016 | Heilman et al. |
| 2018/0049759 A1 | 2/2018 | Thomas |
| 2018/0229010 A1 | 8/2018 | Walzman |
| 2019/0069949 A1 | 3/2019 | Vrba et al. |
| 2019/0105477 A1* | 4/2019 | Heilman ........... A61M 25/0155 |
| 2019/0201093 A1 | 7/2019 | Thom |
| 2019/0269392 A1 | 9/2019 | Celermajer et al. |
| 2019/0298977 A1 | 10/2019 | Heilman et al. |
| 2020/0038057 A1 | 2/2020 | Rai et al. |
| 2020/0069927 A1 | 3/2020 | Malek et al. |
| 2020/0113619 A1 | 4/2020 | Tsukashima et al. |
| 2020/0289061 A1 | 9/2020 | Rapoport et al. |
| 2020/0375766 A1 | 12/2020 | Malek |
| 2020/0390455 A1 | 12/2020 | Nguyen et al. |
| 2022/0183695 A1 | 6/2022 | Julason, Jr. |
| 2022/0202486 A1 | 6/2022 | Morales |
| 2022/0273322 A1 | 9/2022 | Goyal |
| 2022/0409857 A1 | 12/2022 | Saadat et al. |
| 2023/0114949 A1 | 4/2023 | Savastano et al. |
| 2023/0233819 A1 | 7/2023 | Malek et al. |

FOREIGN PATENT DOCUMENTS

| | | |
|---|---|---|
| WO | WO-2018145212 A1 | 8/2018 |
| WO | WO-2019148094 A1 | 8/2019 |
| WO | WO-2021007346 A1 | 1/2021 |
| WO | WO-2021222157 A1 | 11/2021 |
| WO | WO-2022087369 A1 | 4/2022 |
| WO | WO-2024098065 A1 | 5/2024 |

OTHER PUBLICATIONS

Final Office Action for U.S. Appl. No. 17/976,667 dated May 24, 2023, 28 pages.
International Search Report and Written Opinion for International Application No. PCT/US2021/029276, mailed Sep. 23, 2021, 8 pages.
Invitation to Pay Additional Fees for International Application No. PCT/US2021/029276, mailed Jul. 19, 2021, 2 pages.
Kim, Wi Jin, et al. "Endovascular transmural access to carotid artery perivascular tissues: safety assessment of a novel technique." Journal of NeuroInterventional Surgery (2022): 1-8.
Mercator. Bullfrog Micro-Infusion Device Brochure. http://www.mercatormed.com/bullfrog-micro-infusion-device, Feb. 17, 2016, Accessed online Nov. 16, 2022, 3 pages.
Non-Final Office Action for U.S. Appl. No. 17/976,667 dated Mar. 10, 2023, 28 pages.
EP Application No. 21797425.2 Extended European Search Report dated Feb. 12, 2024, 8 pages.
PCT/US2023/078841 International Search Report and Written Opinion dated Feb. 26, 2024, 15 pages.
U.S. Appl. No. 18/469,437 Non-Final Office Action dated Nov. 21, 2023, 22 pages.

* cited by examiner

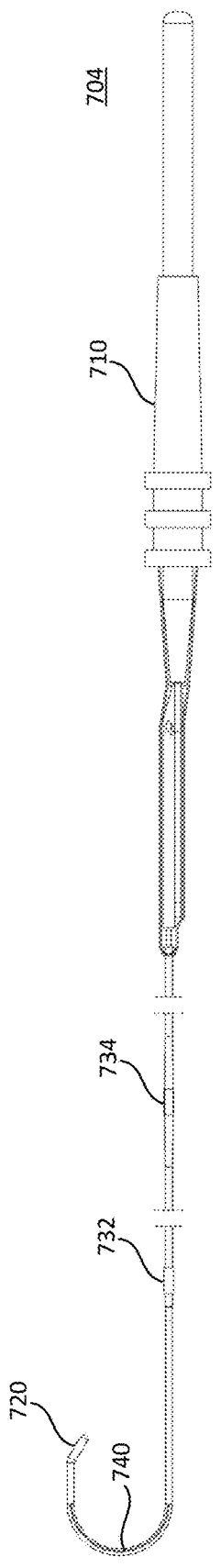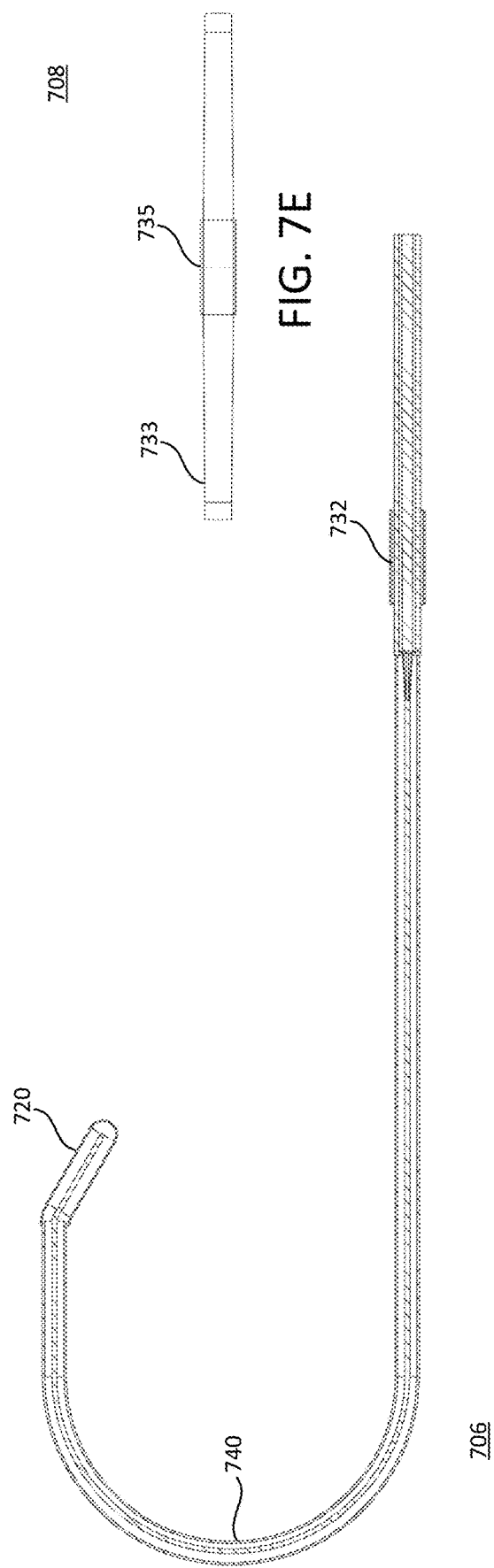

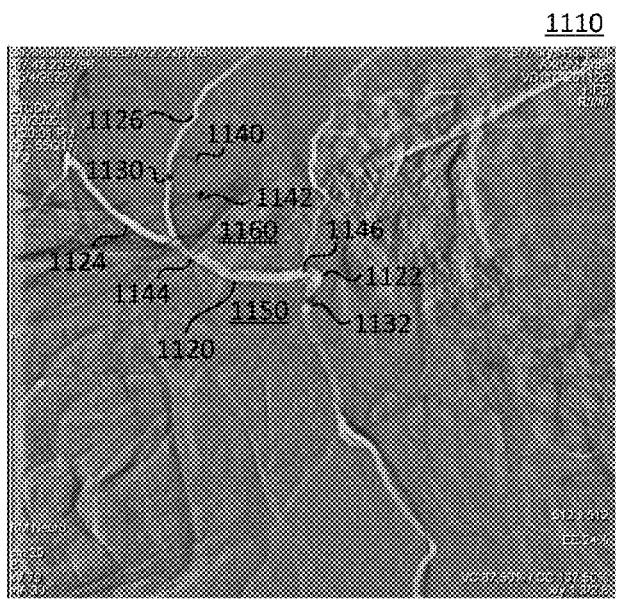
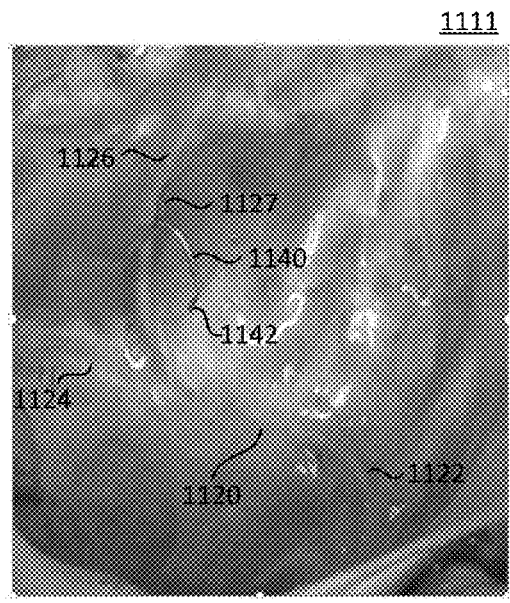
FIG. 11H
FIG. 11I
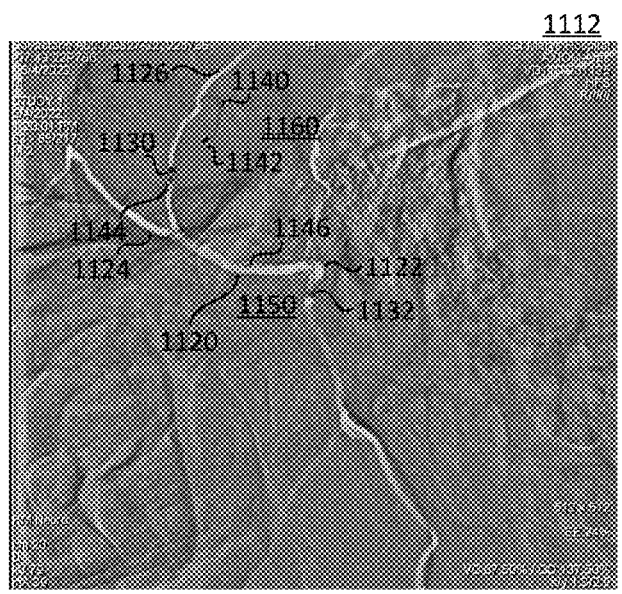
FIG. 11J

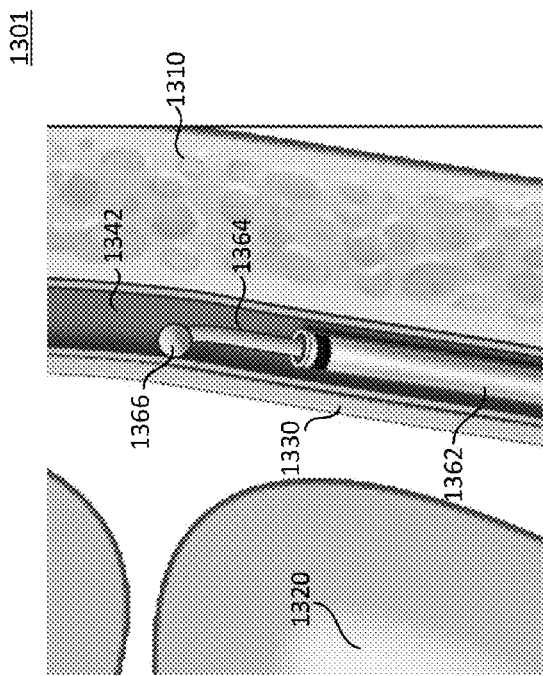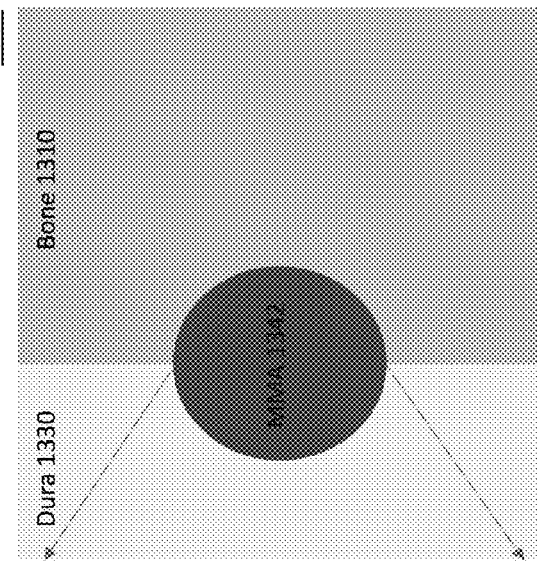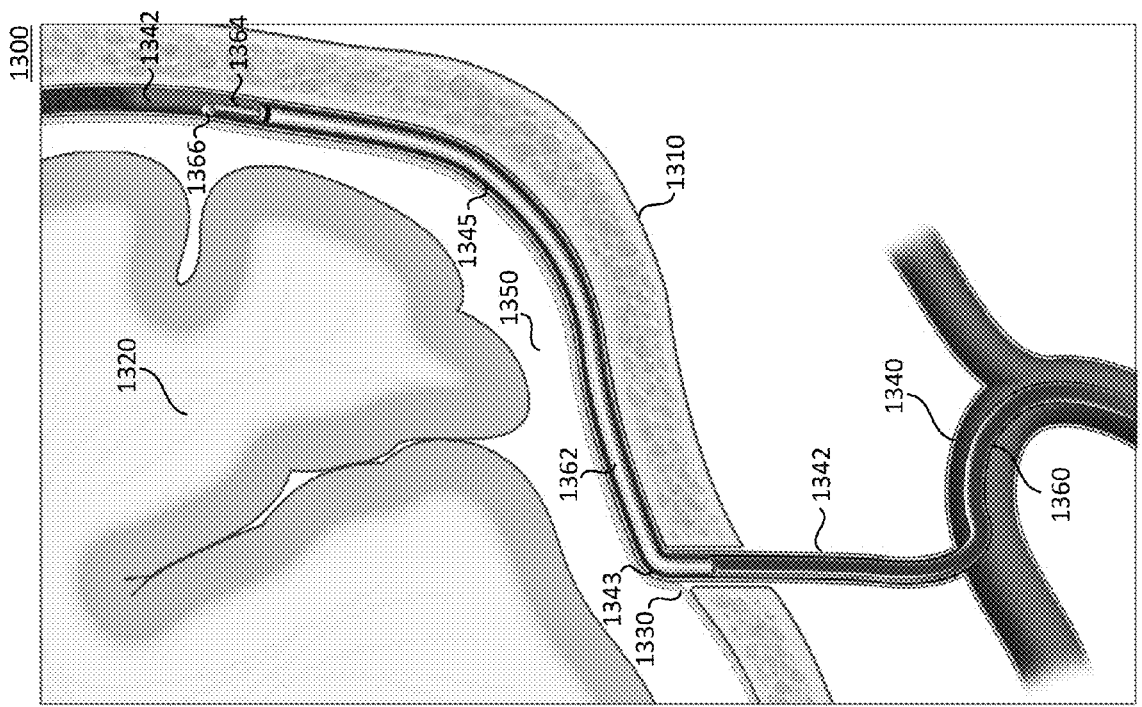
FIG. 13A
FIG. 13B
FIG. 13C

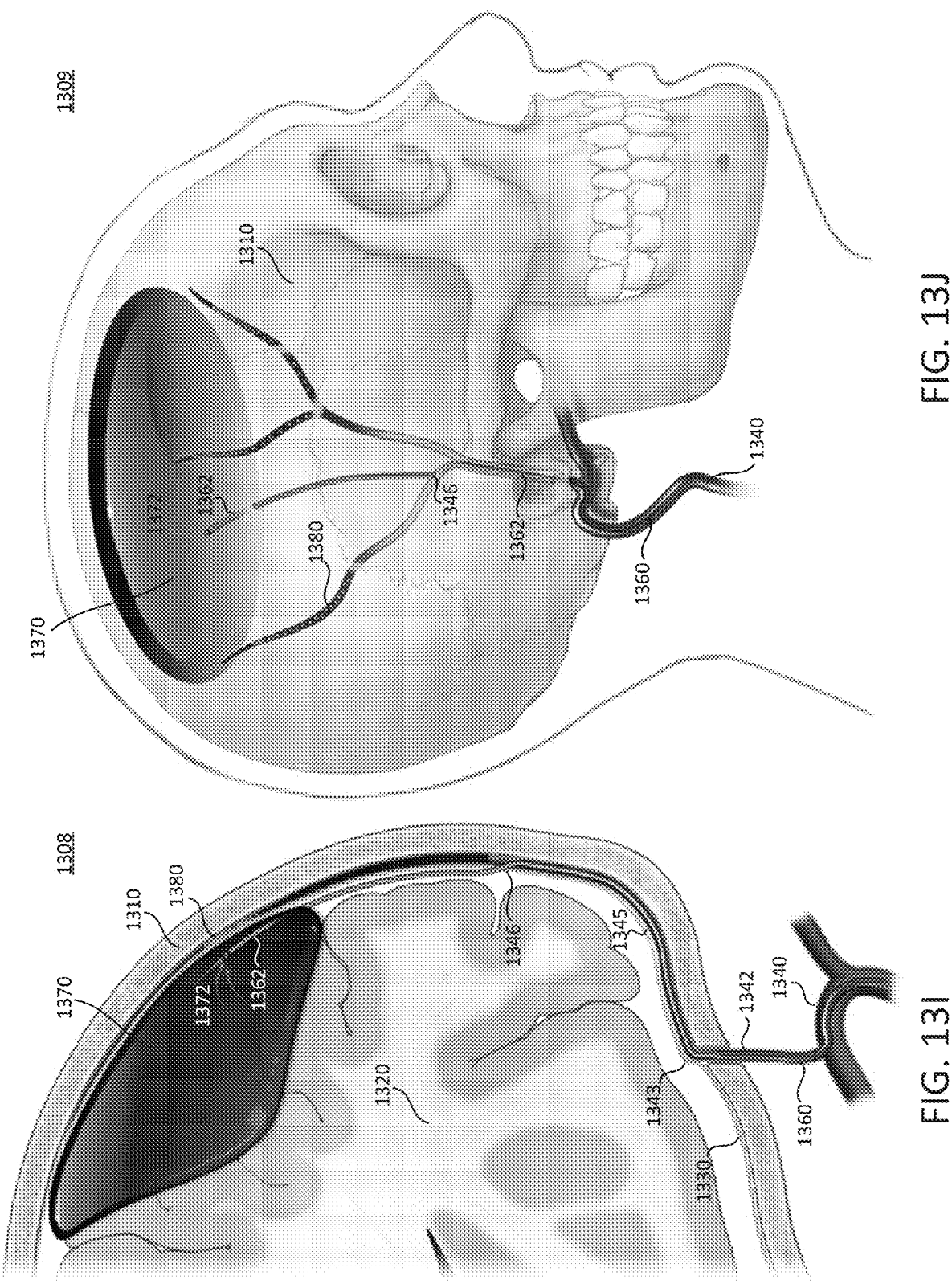

SYSTEMS, DEVICES, AND METHODS FOR ACCESSING A SUBDURAL SPACE

CROSS-REFERENCE TO RELATED APPLICATIONS

This application claims the benefit of U.S. Provisional Application No. 63/422,799, filed Nov. 4, 2022, the content of which is hereby incorporated by reference in its entirety.

TECHNICAL FIELD

Devices, systems, and methods herein relate to minimally invasive procedures for accessing an intracranial extravascular space in a subject, including but not limited to treating a subdural hematoma.

BACKGROUND

A subdural hematoma (SDH) is a collection of blood outside the brain generally resulting from head trauma and commonly associated with blood thinners. If not surgically drained, a SDH may cause an increase in the pressure inside the skull, damage the delicate brain tissue, and become life-threatening. Initially, acute SDH (aSDH) are generally formed by stiff clots, but may progressively liquefy in subsequent days into a viscous subacute SDH (saSDH), which tends to perpetuate and expand into a chronic SDH (cSDH). A chronic subdural hematoma (cSDH) is a collection of blood on the brain's surface that generally begins forming weeks after head trauma and expands, with the potential to cause brain compression, neurologic deficits, and death. cSDH is expected to be the most common neurosurgical diagnosis in the US by the year 2030 and has an in-hospital mortality rate of 16.7%, a 1-year mortality rate of 32% with only 21.1% of patients admitted returning home, and is associated with a marked reduction in patient's life expectancy. cSDH is becoming a public health issue in aging populations as it is associated with brain atrophy in elderly patients and anti-coagulation with the use of blood thinners. Furthermore, acute-on-chronic SDH (acSDH) occurs for more than 10% of patients with cSDH and may be formed by encapsulated liquefied hematoma mixed with solid subdural clots.

The current standard of treatment for symptomatic SDH is surgical evacuation. For example, two burr holes are formed to drain the relatively thin cSDH, and craniotomies (e.g., large bone 'windows') are used to drain the viscous fluids and/or clots of an aSDH and acSDH. Surgical evacuation may be initially effective, but have a failure rate of up to about 37%. Even when an initial conventional treatment fails and patients undergo a second surgical treatment, further recurrences are common; recurrence for cSDH can be up to about 46%. Furthermore, open surgical intervention may pose additional risks to a patient including temporary discontinuation of anticoagulation and antiplatelet medications (e.g., thereby increasing the risk of ischemic complications) and the use of general anesthesia that may contribute to morbidity and mortality rates as high as about 25% and about 11%, respectively.

Surgical evacuation is commonly combined with the introduction of drains in the subdural space, which generally remain in place for up to about three days. While drains may reduce the recurrence rate and the 6-month mortality rate by about 50%, they may also result in other complications such as brain injury, hemorrhage from neomembranes, and infection.

Endovascular middle meningeal artery (MMA) embolization is an endovascular procedure used to reduce postoperative recurrence of SDH that includes the injection of embolic agents in the MMA whereby the hematoma is slowly reabsorbed, thus reducing the mass effect on the brain over a period of weeks to months. MMA embolization may be used to treat cSDH and reduce recurrence in high-risk patients with aSDH, saSDH, and acSDH (i.e., coagulopathy or requiring blood thinners).

Surgical evacuation for rapid brain decompression has been used with endovascular MMA as a preoperative or postoperative adjunct to treat SDH. However, such a combination carries their aforementioned risks and requires two separate procedures that may increase hospitalization, recovery time, and healthcare costs. Accordingly, it may be desirable to provide an endovascular procedure to access a subdural space to facilitate evacuation of an SDH and embolization of an artery.

SUMMARY

Described here are systems, devices, and methods useful for minimally invasive surgical procedures. These systems, devices, and methods may, for example, access a subdural space (e.g., intradural cavity) and treat an intracranial hematoma of a subject. For example, drainage of one or more of intracranial extravascular fluid, thrombus, and particulate matter (e.g., subdural hematoma) and embolization of the middle meningeal artery in a single endovascular intervention (e.g., approach) are described herein.

In some embodiments, an apparatus may comprise a shaft configured to be slidably disposed within a lumen of a catheter. The shaft may be configured to be advanced distally from a distal end of the catheter and into a blood vessel of a subject. The shaft may include a perforating tip including an energy element. The energy element may be configured to generate radiofrequency (RF) energy to form an opening through a wall of the blood vessel and dura of the subject and into an extravascular space of the subject. A curved section may be configured to be radially constrained within the lumen of the catheter. The curved section may be configured to curve toward the wall of the blood vessel and the dura upon exiting the lumen of the catheter such that the energy element is positioned to form the opening. A first discontinuity may be disposed between the perforating tip and the curved section. A second discontinuity may be disposed proximal of the curved section. The second discontinuity may be configured to orient the curve to follow a curve of the blood vessel as the shaft is advanced within the lumen of the catheter.

In some embodiments, the first discontinuity includes a bend in the shaft. In some embodiments, the curved section has a first radius of curvature, and the first discontinuity includes a section of the shaft having a second radius of curvature that is smaller than the first radius of curvature. In some embodiments, the curved section may be configured to transition into a curved configuration as the curved section travels through the opening and into the extravascular space.

In some embodiments, the curved section may have a cross-section with a first lateral dimension that is greater than a second lateral dimension. In some embodiments, the second discontinuity may include a bend in the shaft. In some embodiments, the second discontinuity may include a partial helix or a twist in the shaft. In some embodiments, the curved section may have a first curved section that includes a convex curvature, and the shaft further includes a second curved section proximal of the first curved section, the second curved section including a concave curvature. In some embodiments, the shaft includes a wider section having a lateral dimension that is equal to or substantially equal to an inner diameter of the lumen of the catheter to prevent ovalizing of the catheter as the catheter advances through the opening. In some embodiments, the opening has a length that is equal or substantially equal to a length of the energy element.

In some embodiments, a system may comprise a catheter having a proximal end and a distal end and defining a lumen therebetween. The distal end of the catheter may be configured to be disposed within a blood vessel of a subject. A shaft slidably may be disposed within the lumen, the shaft including a perforating tip having an energy element configured to generate RF energy to penetrate through a wall of the blood vessel and dura of the subject. The shaft may further include a curved section configured to transition from a radially constrained configuration to a curved configuration. The shaft may be configured to be advanced along the catheter such that the curved section is oriented to curve along a direction of a curve of the blood vessel and to exit a distal end of the catheter. The curved section may be configured to curve toward the wall of the blood vessel such that the perforating tip is positioned against the wall of the blood vessel and, upon activation of the energy element, can penetrate through the wall of the blood vessel and the dura and into an extravascular space.

In some embodiments, the distal end of the catheter may include a radiopaque element. In some embodiments, the shaft may include a first radiopaque element disposed at the perforating tip, and a second radiopaque element disposed proximal of the curved section. In some embodiments, the catheter may be configured to be advanced into the extravascular space over the shaft. The shaft may further include a wider section disposed proximal of the curved section, the wider section to prevent ovalizing of the catheter as the catheter is advanced into the extravascular space. In some embodiments, the distal end of the catheter may include a first radiopaque element, and the shaft may include a second radiopaque element disposed near the wider section, such that the wider section can be aligned with the distal end of the catheter prior to advancing the catheter into the extravascular space.

In some embodiments, the shaft is a first RF device, the system further includes a second RF device including a linear tip configured to penetrate through a membrane of a subdural hematoma. In some embodiments, the second RF device is configured to deliver RF energy to close a vascular lumen of the blood vessel.

In some embodiments, a method includes positioning a distal end of a catheter disposed within an intracranial vessel of a subject near a target location, advancing a shaft through a lumen of the catheter such that a curved section of the shaft curves in a direction along a curve of the vessel, the curved section being constrained within the lumen of the catheter, extending the curved section of the shaft out of the distal end of the catheter such that the curved section curves toward a wall of the vessel and positions a RF element disposed at a distal end of the shaft against the wall of the vessel, activating the RF element to deliver RF energy to the wall of the vessel to create an opening through the wall of the vessel and dura of the subject and into an extravascular intracranial space, advancing the distal end of the shaft into the extravascular intracranial space until the curved section transitions to an unconstrained configuration within the extravascular intracranial space, and advancing the catheter over shaft and into the extravascular intracranial space.

In some embodiments, the method further includes advancing the distal end of the shaft into a subdural hematoma, advancing the catheter over at least a portion of the shaft and into the subdural hematoma, and applying suction to the lumen of the catheter to remove fluid from the subdural hematoma after the catheter is positioned within the subdural hematoma. In some embodiments, the method further includes retracting the catheter back toward the opening created in the wall of the artery, and delivering, via the lumen of the catheter, a hemostatic element or RF device to close the opening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A and 7C are schematic diagrams of a shaft, according to embodiments. FIGS. 7B, 7D, and 7E are detailed schematic diagrams of the shaft depicted in FIGS. 7A and 7C, respectively.

FIGS. 11A-11L are images of a method of accessing an extravascular intracranial space, according to embodiments.

FIGS. 13A, 13B, 13D, 13E, 13G, and 13I are coronal cross-sectional views of a head of a subject, according to embodiments. FIG. 13C is a schematic axial cross-sectional view of a head of a subject, according to embodiments. FIGS. 13F, 13H, and 13J are lateral views of a head of a subject, according to embodiments.

DETAILED DESCRIPTION

Figure 1:
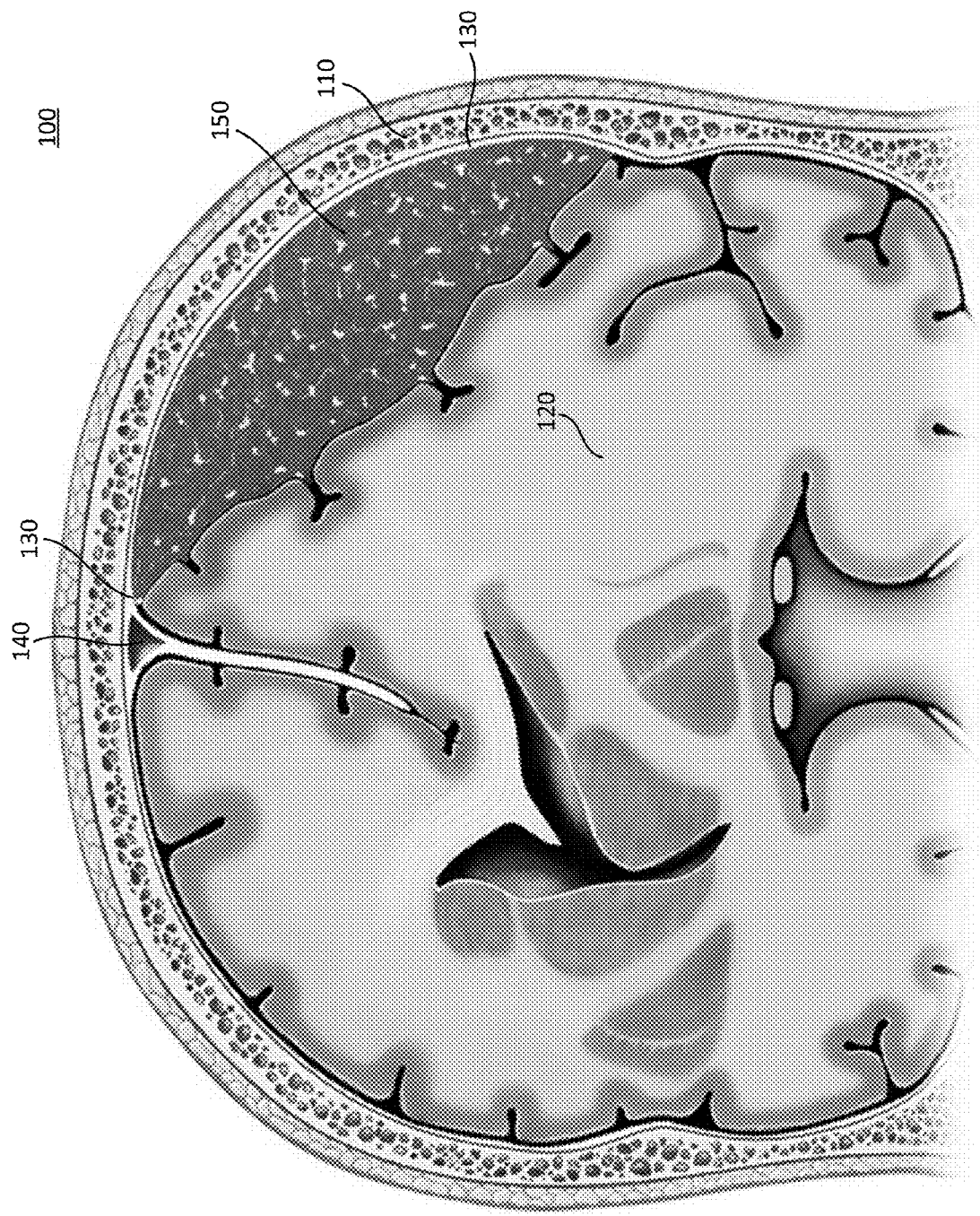
FIG. 1 is a schematic coronal cross-sectional view of a subdural hematoma of a subject, according to embodiments.

Described here are systems, devices, and methods for use in minimally invasive surgical procedures enabling transvascular neurosurgery without opening the skull. For example, the systems, devices, and methods described herein may improve access to an extravascular space (e.g., subdural space, extravascular spinal cord space) of a subject by: being performed under minimal sedation; reducing one or more of procedural complexity, sterile field management, and time; enabling continual use of anticoagulation and antiplatelet medications; providing quicker post-surgical recovery and shortening hospitalization time; and reducing complications when compared to conventional open surgical procedures. For example, access to an extravascular space may include navigation within an body compartment without blood extravasation while the blood vessel is patent or tissue damage (e.g., due to perforation). In some embodiments, access to the subdural space may be used to facilitate drainage of subdural fluid.

While conventional solutions require separate procedures to evacuate a subdural hematoma (SDH) and to embolize an artery, the systems, devices, and methods disclosed herein may be performed within a single endovascular approach. For example, the systems, devices, and methods described herein may facilitate immediate brain decompression through transvascular drainage of a SDH and prevention of hematoma recurrence through embolization of the MMA within the same procedure, thereby obviating the need for a second and separate invasive open surgical procedure.

In some embodiments, systems and devices may comprise a first catheter configured to self-orient within a blood vessel in order to cut through a vessel wall and dura in a push-less and depth-controlled manner without injuring the brain. The first catheter may then be advanced atraumatically through a subdural space and into a SDH for drainage using a second catheter. Once the viscous fluid of the SDH has been evacuated, the second catheter or a third catheter may be used to occlude the arteriotomy formed by the first catheter without bleeding. Some of the surgery systems described herein may be used to perform surgical procedures including one or more of surgical evacuation, embolization, drug delivery, device delivery (e.g., including electrodes), and combinations thereof.

In some embodiments, a method may comprise positioning a distal end of a catheter disposed within an intracranial vessel of a subject near a target location, and advancing a shaft through a lumen of the catheter such that a curved section of the shaft curves in a direction along a curve of the vessel. For example, the curved section may be constrained within the lumen of the catheter. The curved section of the shaft may be extended out of the distal end of the catheter such that the curved section curves toward a wall of the vessel and positions a RF element disposed at a distal end of the shaft against the wall of the vessel. The RF element may be activated to deliver RF energy to the wall of the vessel to create an opening through the wall of the vessel and dura of the subject and into an extravascular intracranial space. The distal end of the shaft may be advanced into the extravascular intracranial space until the curved section transitions to an unconstrained configuration within the extravascular intracranial space. The catheter may be advanced over shaft and into the extravascular intracranial space.

In some embodiments, an apparatus may comprise a shaft configured to be slidably disposed within a lumen of a catheter. The shaft may be configured to be advanced distally from a distal end of the catheter and into a blood vessel of a subject. In some embodiments, the shaft may include a perforating tip including an energy element, the energy element configured to generate RF energy to form an opening through a wall of the blood vessel and dura of the subject and into an extravascular space of the subject. A curved section of the shaft may be configured to be radially constrained within the lumen of the catheter. The curved section may be configured to curve toward the wall of the blood vessel and the dura upon exiting the lumen of the catheter such that the energy element is positioned to form the opening. A first discontinuity may be disposed between the perforating tip and the curved section, and a second discontinuity may be disposed proximal of the curved section. The second discontinuity may be configured to orient the curve to follow a curve of the blood vessel as the shaft is advanced within the lumen of the catheter.

In some embodiments, a system may comprise a catheter having a proximal end and a distal end and defining a lumen therebetween. The distal end of the catheter may be configured to be disposed within a blood vessel of a subject. A shaft may be slidably disposed within the lumen. The shaft may include a perforating tip having an energy element configured to generate RF energy to penetrate through a wall of the blood vessel and dura of the subject. The shaft may further include a curved section configured to transition from a radially constrained configuration to a curved configuration. The shaft may be configured to be advanced along the catheter such that the curved section is oriented to curve along a direction of a curve of the blood vessel and to exit a distal end of the catheter. The curved section may be configured to curve toward the wall of the blood vessel such that the perforating tip is positioned against the wall of the blood vessel and, upon activation of the energy element, can penetrate through the wall of the blood vessel and the dura and into an extravascular space. Other suitable examples of systems, devices, and methods are described in International Application Serial No. PCT/US2021/029276, filed on Apr. 27, 2021, the disclosure of which is hereby incorporated by reference in its entirety.

Systems, devices, and methods described herein can be used to access an extravascular space of a subject, including, for example, intradural extravascular spaces along a spinal cord of a subject or in a brain of a subject. FIG. 1 is a schematic coronal cross-sectional view of a subject 100 including a skull 110 encasing each of a brain 120, a dura mater (dura) 130, a superior sagittal sinus (SSS) 140, and a subdural hematoma (SDH) 150. An SDH is a type of bleeding in which a collection of blood, usually associated with a traumatic brain injury, gathers between the inner layer of the dura mater and the arachnoid mater of the meninges surrounding the brain. It usually results from tears in bridging veins that cross the subdural space. Subdural hematomas may cause an increase in the pressure inside the skull, which in turn can cause compression of and damage to delicate brain tissue. The SDH 150 is depicted in FIG. 1 between the brain 120 and the dura 130 and typically faces the convexity of the cerebral hemisphere. Though not shown in FIG. 1, an SDH may be in proximity to the vascular structures of the dura 130 including a middle meningeal artery (MMA), a superior sagittal sinus (SSS) 140, an inferior sagittal sinus (ISS), a superior petrosal sinus (SPS), and a transverse-sigmoid junction or the transverse sinus (TS).

The SSS 140 is a midline vein without valves that courses along the falx cerebri from the vicinity of the *crista galli* to the confluence of sinuses at the posterior cranium. The SSS 140 faces both cerebral hemispheres and generally has a length of between about 31 cm and about 38 cm, and receives between about 12 and about 20 venous tributaries from the left and right cerebral hemispheres. Generally, the SSS 140 has a triangular shape with a width between about 3 mm and about 18 mm and a height between about 3 mm and about 14 mm. The cross-sectional area of the SSS 140 may be between about 15 mm$^2$ and about 90 mm$^2$, and the angle between the sinus wall and a midline may be between about 25° and about 65°. A typical distance between the SSS 140 and the subdural hematoma 150 is usually less than about 35 mm. The SSS 140 is typically surrounded by dura 130 and separated from the brain 120 by the arachnoid and subarachnoid space filled with cerebrospinal fluid. Brain atrophy may result in widened spaces between the SSS 140 and the brain 120. For example, a space between a surface of the brain 120 and the dura 130 may be between about 1 mm and about 20 mm (e.g., between about 2 mm and about 8 mm) for subjects having chronic SDH.

Figure 2A:
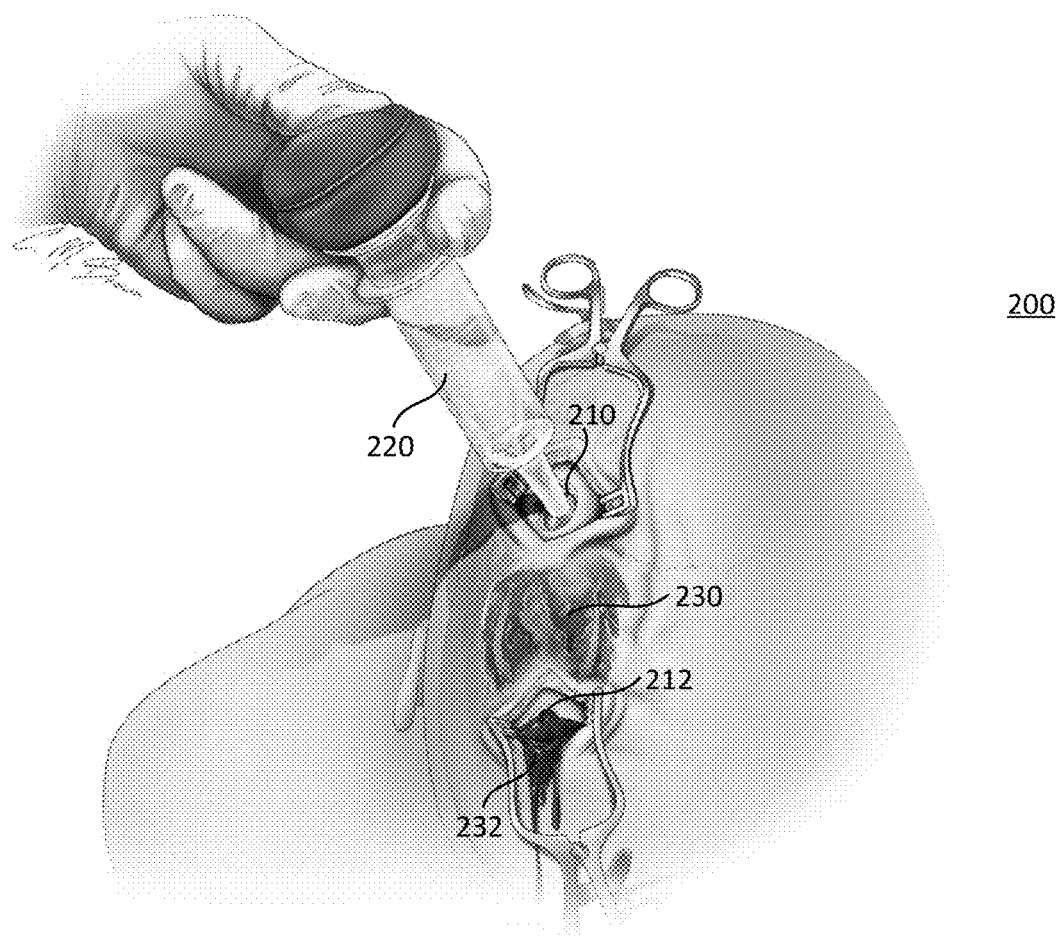
FIGS. 2A and 2B are a respective schematic perspective view and an image of a subject undergoing surgical evacuation, according to embodiments.
Figure 2B:

It may further be helpful to briefly discuss conventional approaches to treatment of subdural hematomas. FIGS. 2A and 2B depict a schematic perspective view 200 and an image 202 respectively, of a subject undergoing surgical evacuation of a hematoma. In particular, a first bore hole 210 and a second bore hole 212 are formed in the subject's skull in proximity to a hematoma 230 shown for the sake of illustration in FIG. 2A without the overlying portion of the skull. Saline solution 220 may be introduced into the first bore hole 210 such that fluid 232 (including hematoma 230) may flow out of the second bore hole 212.

Figure 3A:
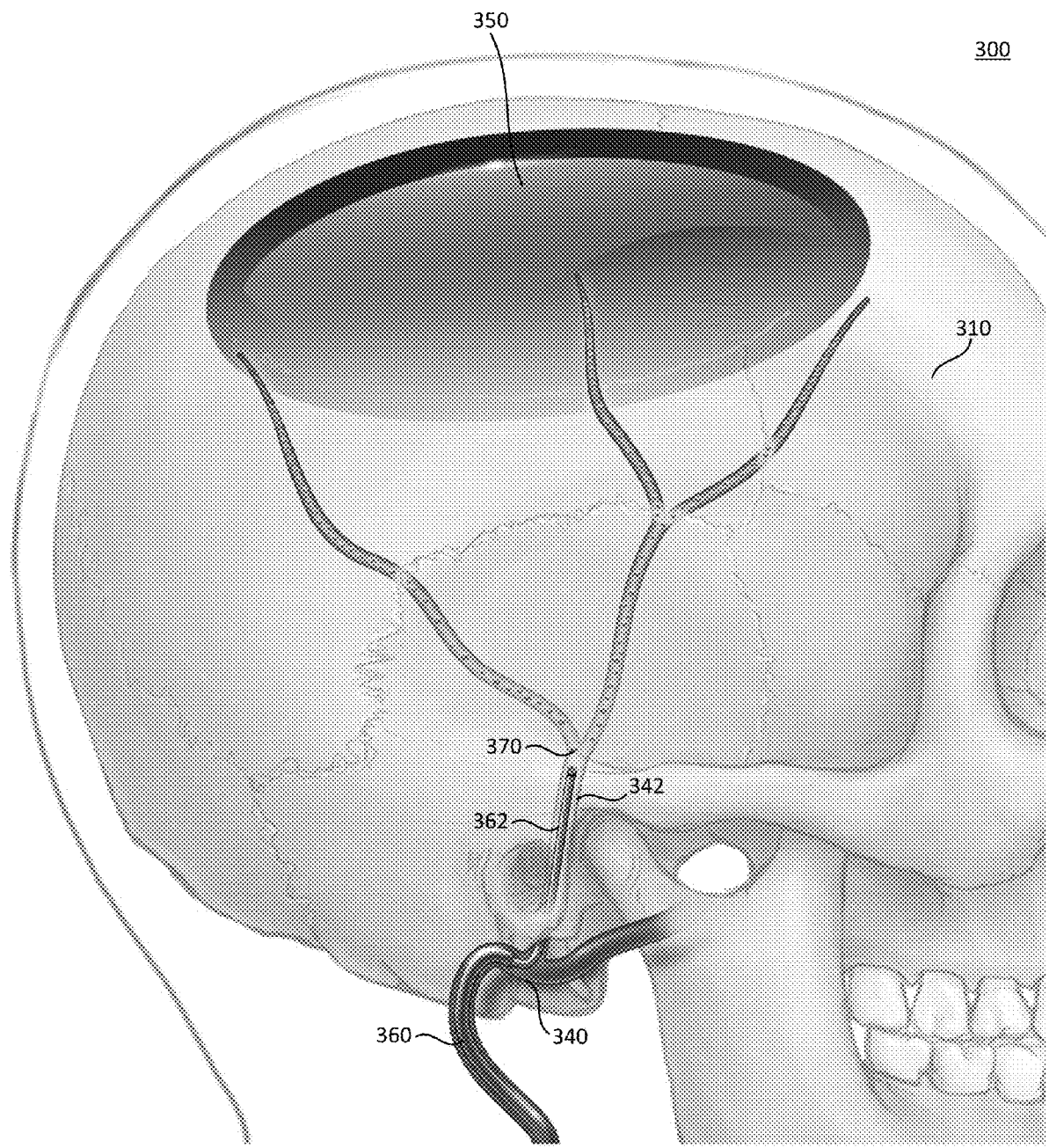
FIG. 3A is a sagittal cross-sectional view of a head of a subject, according to embodiments.

In some embodiments, a single endovascular approach may be performed to access an extravascular space of a subject. For example, FIGS. 3A-3D are lateral views of a head 300, 302, 304, 306 of a subject. The head 300 of FIG. 3A depicts a skull 310, an internal maxillary artery 340 coupled to a middle meningeal artery (MMA) 342, and a subdural hematoma (SDH) 350. In some embodiments, a sheath (e.g., sleeve, delivery catheter) 360 may be advanced through one or more of the internal maxillary artery 340 and MMA 342. A catheter 362 (e.g., embolization catheter) may be advanced from a distal end of the sheath 360 and configured to deliver a hemostatic element 370 (e.g., occlusion element, embolic material, embolic fluid, micro particles, coil) into a set of branches of the MMA 342 for reducing hemorrhage from one or more branch vessels of the MMA 342. In some embodiments, the sheath 360 may be advanced through any suitable vascular access point (e.g., peripheral arterial vasculature) such as the femoral artery (e.g., groin), radial artery (e.g., wrist), brachial artery, carotid artery, and the like.

The MMA 342 is generally the third branch of the first portion of the internal maxillary artery 340. Each side of the head may include an MMA 342 that branches off the internal maxillary artery 340 in the infratemporal fossa, through the *foramen spinosum* and into the intracranial compartment where the MMA 342 deflects anteriorly and laterally at an angle between about 60° and about 120° relative to a longitudinal axis of the *foramen spinosum*.

Figure 3D:
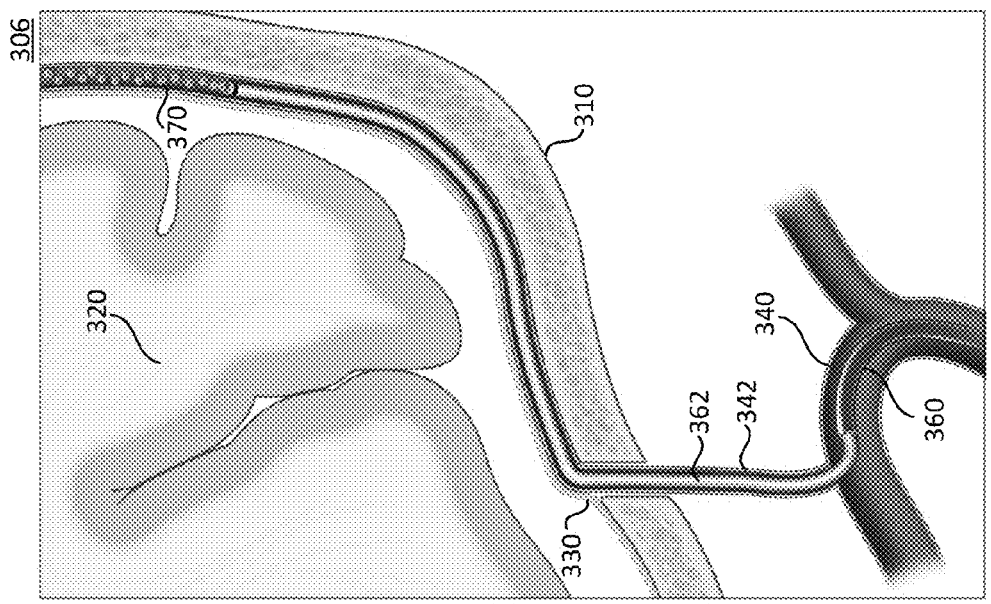
FIGS. 3B-3D are coronal cross-sectional views of a head of a subject, according to embodiments.
Figure 3C:
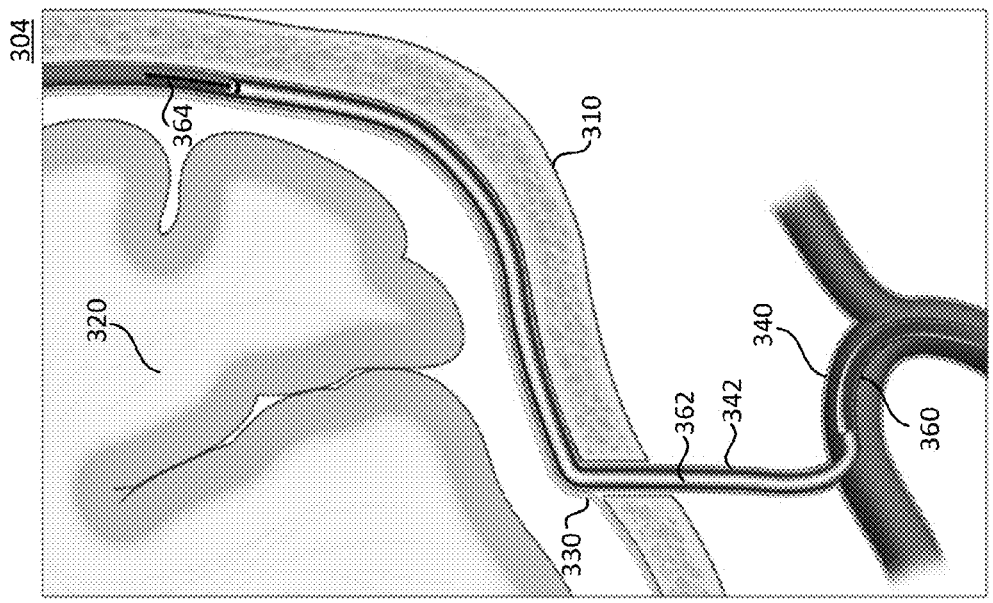
Figure 3B:
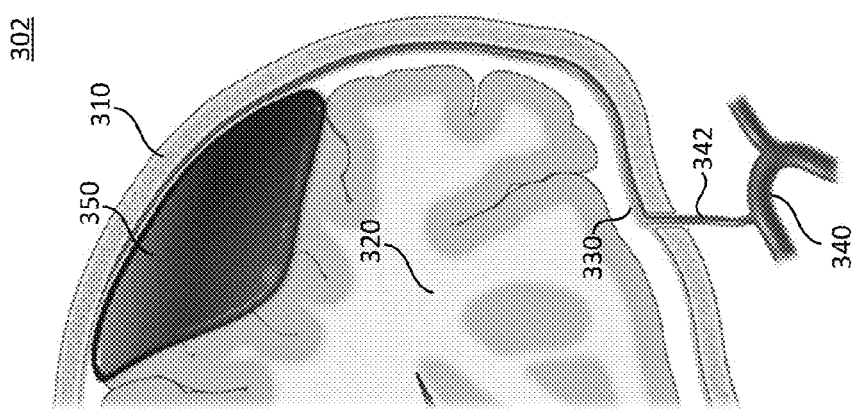

As shown in FIGS. 3B-3D, the MMA 342 is typically located on the epidural side of the dura 330. The MMA 342 generally bifurcates parallel to the dura 330. The MMA 342 may supply blood to the dura 330, the outer meningeal layer, and the calvaria. A main trunk of the MMA 342 may generally be between about 14 mm and about 34 mm. The MMA 342 generally bifurcates into a frontal and a parietal branch (as well as other minor branches). A mean diameter of the main trunk of the MMA 342 may be between about 0.6 mm and about 1.2 mm. However, subjects having cSDH may have a mean diameter of the main trunk of the MMA 342 between about 1 mm and about 2 mm. The MMA 342 may supply blood to pathological membranes that maintain and/or expand the SDH. FIG. 3C depicts a catheter 362 and a shaft 364 advanced into the MMA 342 between the dura 330 and skull 310. The shaft 364 may be configured to be slidably disposed within a lumen of the catheter 362. As described in more detail herein, the shaft 364 may be configured to form an opening through a wall of the blood vessel (e.g., MMA 342) and dura 330 and into an extravascular space of the subject to facilitate access to the intradural space between the dura 330 and brain 320. FIG. 3D depicts delivery of a hemostatic element 370 into the MMA 342 by the catheter 362.

Figure 4A:
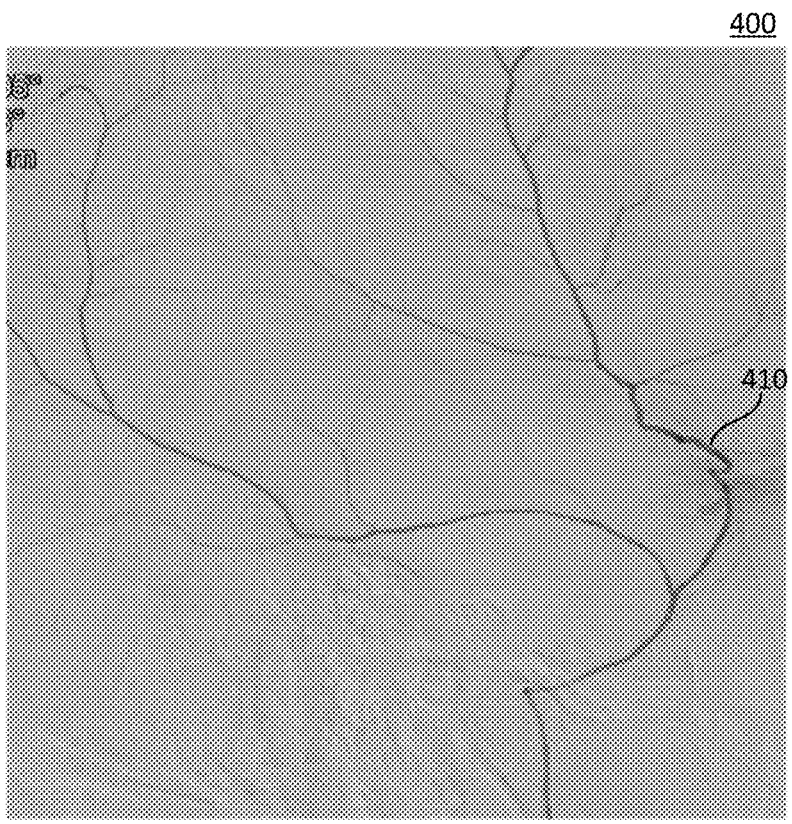
FIGS. 4A and 4B are X-ray images of arterial blood flow in a head of a subject, according to embodiments.
Figure 4B:
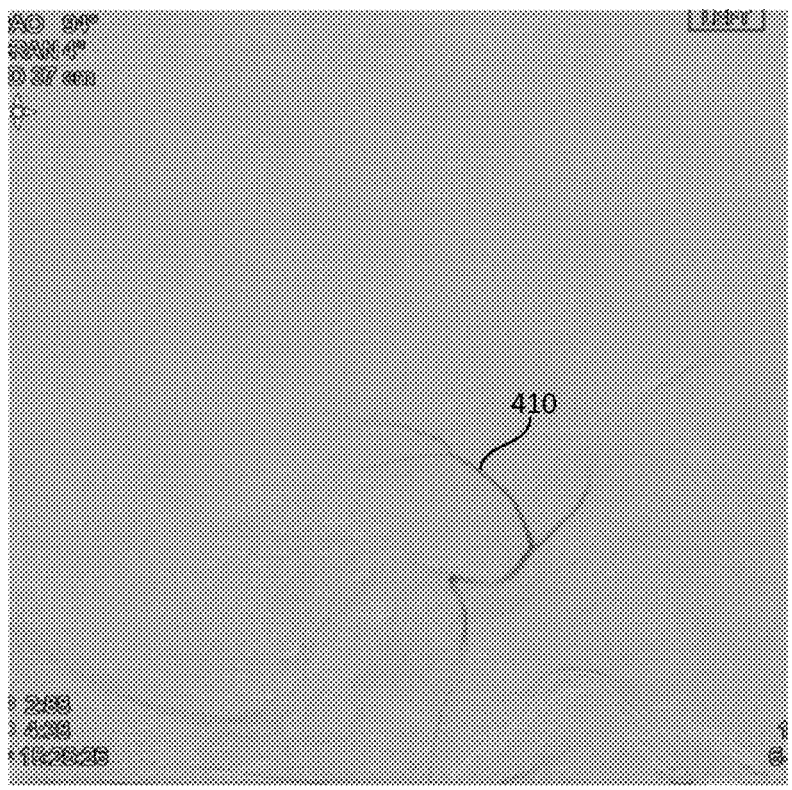
Figure 4C:
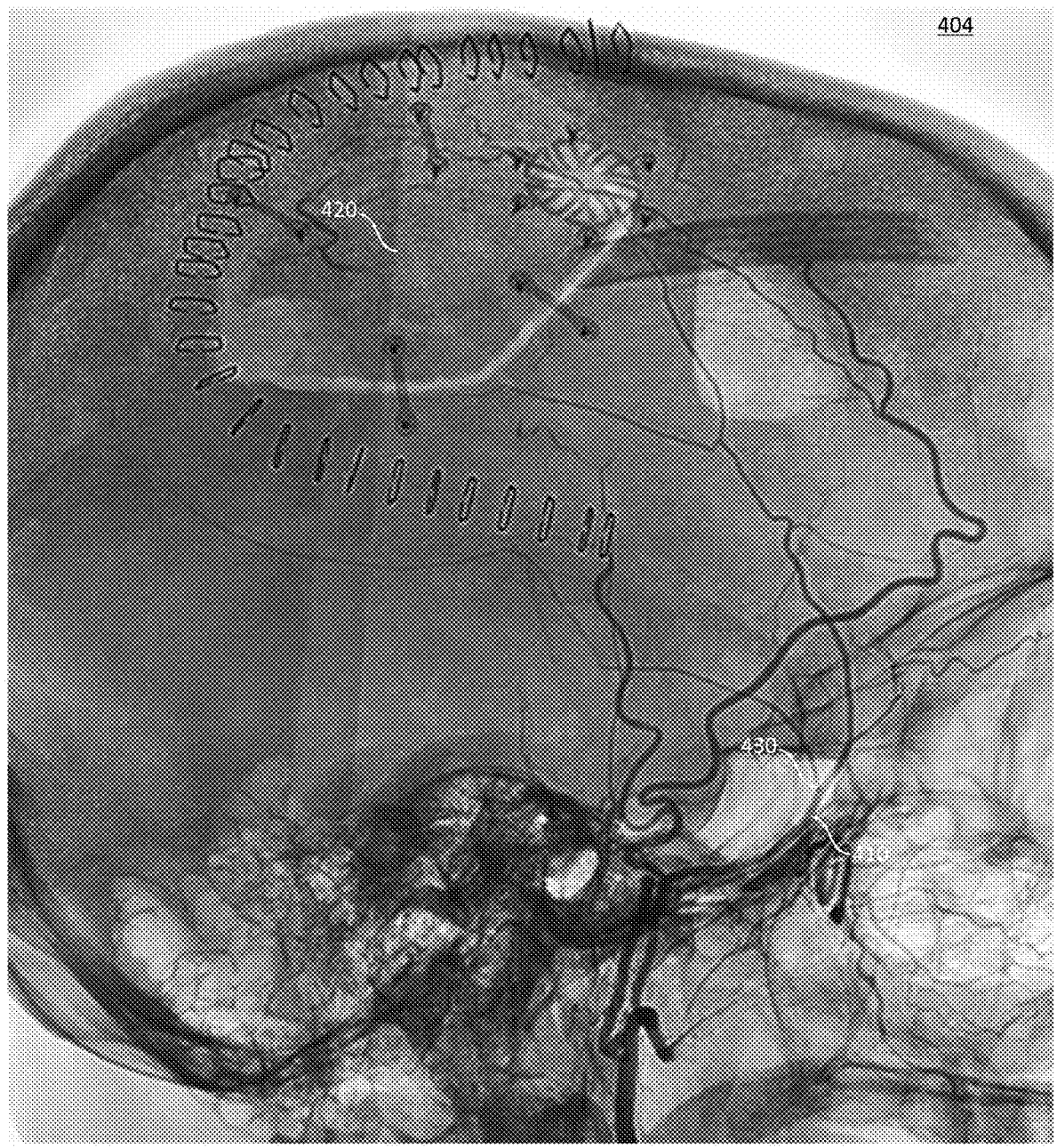
FIG. 4C is an X-ray image of a head of a subject, according to embodiments.

FIGS. 4A and 4B are X-ray images 400, 402 of arterial blood flow in a head of a subject. For example, FIG. 4A shows blood flow through the middle meningeal artery (MMA) 410 and FIG. 4B shows blood flow through the MMA 410 after occlusion of the MMA 410. FIG. 4C is an X-ray image 404 of a head of a subject having two bore holes location 420 connected with a craniotomy and a catheter 430 disposed within the MMA 410.

I. System

Figure 5:
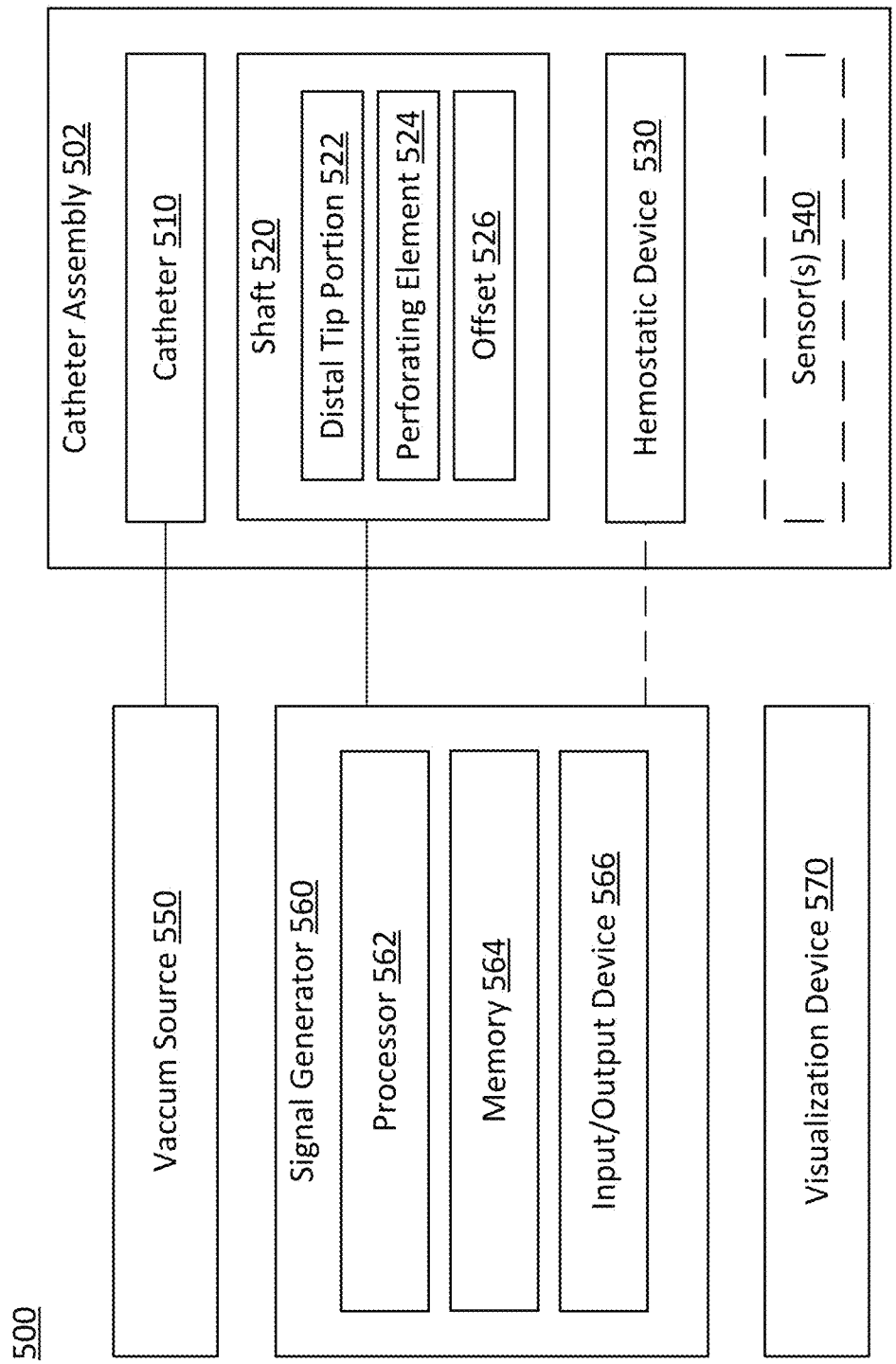
FIG. 5 is a schematic block diagram of a system, according to embodiments.

Systems and devices described herein can be configured to enable transvascular surgery including, but not limited to, improving access to an extravascular space, treatment of a subdural hematoma, delivery of a drug or therapeutic agent, delivery of a device (e.g., sensor, electrode, biopsy device, ablation device, catheter, draining system), implantation of a device, etc. FIG. 5 is a schematic block diagram of a system 500 including a catheter assembly 502, a vacuum source 550, a signal generator 560, and a visualization device 570. The catheter assembly 502 may be configured to form an opening between a blood vessel to an extravascular space of a subject. In some embodiments, the catheter assembly 502 may include a catheter 510, a shaft 520, a hemostatic device 530, one or more optional sensors 540, and an optional sheath (e.g., delivery catheter, guide catheter) (not depicted).

In some embodiments, one or more components of the catheter assembly 502 may include one or more of a hypotube, single solid rod, multiple roads, bundle, tubing (with one or more lumens), shaft strands, cable (two or more wires running side by side, bonded, twisted or braided), coil, braid, combinations thereof, and the like. In some embodiments, one or more components of the catheter assembly 502 may include one or more of stainless steel, nitinol, silver, titanium, copper, cobalt chromium, nickel chromium, platinum iridium, polymer, nylon, polyamides, fluoropolymers, polyolefins, polythetrafluoroethylene, high density polyethyene, polyurethanes and polyimides, ceramic, bioabsorbable or dissolvable material, combinations thereof, and the like.

In some embodiments, one or more components of the catheter assembly 502 may have a tip bending stiffness between about 0.0002 lb/in$^2$ to about 0.15 lb/in$^2$, including all ranges and sub-values in-between. The components of the catheter assembly 502 may have a variable tip bending stiffness along a respective length of each component.

In some embodiments, one or more components of the catheter assembly 502 may include scoring configured to increase flexibility (e.g., to traverse the curves of *foramen spinosum*). The scoring may include, but is not limited to, a spiral scoring pattern (e.g., continuous, interrupted), a radial scoring pattern, a bespoke scoring pattern, a radial ring pattern, a longitudinal scoring, an oblique scoring, a window, a tab, a hole, combinations thereof, and the like.

In some embodiments, one or more components of the catheter assembly 502 may have a cross-sectional shape including, but not limited to, a circle, an oval, a square, a star, a diamond, a rectangle, a flat shape, combinations thereof, and the like.

Catheter

The catheter 510 can be configured to remove fluid from and/or deliver fluids or devices to an extravascular space. In some embodiments, the catheter assembly has to be sufficiently small and flexible to navigate intracranially by crossing multiple complex angles and have high and precise torqueability to direct perforation towards the subdural space from an access site more than 170 cm away. These challenges are exacerbated by subject variations including the degree of aortic and meningo-cervical vascular tortuosity, the location of the arterial perforation point along the squama of the temporal bone, the fluid viscosity, and the presence of thick membranes and septations.

In some embodiments, the catheter 510 may be slidably disposed within a lumen of a sheath. For example, the sheath may include one or more of a guide catheter (e.g., 5F Asahi Fubuki Guide Catheter), intermediate delivery catheter (e.g., DAC 044, Stryker), and a microcatheter (e.g., 0.027" Phenom 27 Microcatheter, Medtronic).

The catheter 510 can be designed to have high flexibility. In some embodiments, the catheter 510 has sufficient flexibility so as to take the shape of a shaft 520 slidably disposed therein. However, the shape of the catheter 510 and shaft 520 may be constrained by the shape of the lumen or body cavity (e.g., artery, subdural space) in which the catheter is disposed.

The catheter assembly may be configured to prevent catheter herniation during advancement, catheter ovalization, and catching of the catheter against the opening. Furthermore, the catheter may be configured to remain patent with no kinks when a shaft is withdrawn without collapsing when negative suction is applied through a lumen of the catheter.

In some embodiments, the catheter 510 may have a distal outer diameter of up to about 0.40 inches and a distal inner diameter of greater than about 0.020 inches, a working length of at least about 150 cm. In some embodiments, the catheter 510 may be configured to advance through a minimal curve angle of 70° without kinking to facilitate advancement into the intracranial compartment through the *foramen spinosum*.

In some embodiments, the catheter 510 has sufficient column strength to generate greater than about 1 N forward load without kinking, ovalizing, or herniating into a vessel (e.g., branching artery) to perforate the MMA and dura, as well as receive a negative pressure of greater than about 29 inHg without collapsing for fluid removal.

In some embodiments, an inner diameter of the catheter 510 may be tapered. For example, an inner diameter at a distal end of the catheter 510 may be smaller than an inner diameter at a proximal end of the catheter 510, e.g., to facilitate increased fluid flow (e.g., during suction).

In some embodiments, a distal end of the catheter 510 may include a radiopaque element. The radiopaque element can be configured to facilitate alignment between the distal end of the catheter 510 and a feature of the shaft, such as, for example, a wider or larger area of the shaft for preventing ovalization, as further described below.

In some embodiments, the catheter may include a plurality of lumens and one or more distal openings. In some embodiments, one or more of the lumens may be configured for suction and/or fluid injection. For example, the catheter may be configured to inject non-ionic dextrose during RF energy delivery to reduce current leaks in order to increase vaporization efficiency of a target tissue.

In some embodiments, the catheter may be configured to minimize, prevent, and/or treat catheter occlusion including slidable elements and deployable elements. For example, the catheter may include two telescoping hypotubes. An outer catheter (e.g., proximal hypotube) may have an inner diameter sufficient to accommodate an inner catheter (e.g., distal hypotube) advanced using, for example, a push wire. These inner and outer hypotubes may include one or more tapers to progressively decrease the gap between the inner hypotube outer diameter and the outer hypotube inner diameter until there is no significant clearance left for a predetermined section of the catheter. The predetermined section may be configured to form a seal that maximizes the cross-section as well as suction force and flow. In addition, a dual-hypotube catheter may have the advantage of obtaining flow arrest in an intraosseous or extracranial MMA with the catheter while providing a lumen for distal instrumentation in the MMA and through a transvascular passageway.

Shaft

The shafts described herein may be configured to fulfill a complex set of requirements. In some embodiments, the catheter assembly may be navigated intracranially through the MMA and have a shaft configured to self-orient within the MMA for forming an opening in the MMA and dura in the correct direction (e.g., away from the skull), as well as indicate to the operator that the shaft has completed self-orientation. For example, for middle meningeal artery transvascular access, the combination of opposing curves (e.g., proximal curve, distal curve) along different segments of the shaft may be configured to induce shaft rotation (e.g., self-orientation) to align the proximal curve of the shaft to the curvature of the *foramen spinosum* and middle cranial fossa (e.g., lateral concavity) and the distal curve of the shaft to the curve of the cranial fossa and cranial vault (e.g., medial concavity).

The shaft may be configured to form a transvascular opening having a length, width, and/or diameter sufficient for passage of a catheter such as, for example, the catheter 510 described above (e.g., aspiration catheter, 0.027" microcatheter). The opening can be circular oval or longitudinal (e.g., slit).

In some embodiments, the shaft 520 may be coupled to the signal generator 560. As described in more detail herein, the shaft 520 may include a distal tip portion 522 having a perforating element 524 configured to create (e.g., form) an opening in a wall of a blood vessel and a dura of the subject. For example, the shaft may be configured to form a transvascular passageway into a subdural space using electrocautery. In some embodiments, the shaft 520 may further include an offset 526 (e.g., discontinuity, bend) configured to orient a predetermined portion of the shaft 520 in a predetermined orientation as the shaft 520 is advanced within the lumen of the catheter 510 and a blood vessel. The shaft 520 may comprise a plurality of portions having one or more different diameters, shapes, durometers, and the like. For example, a multidurometer shaft 520 may be formed by combining a proximal stainless steel core wire having a first stiffness with a distal nitinol wire having a second stiffness less than the first stiffness. Additionally or alternatively, the nitinol wire may be tapered in order to provide proximal stiffness with progressively decreasing distal stiffness.

In some embodiments, the shaft may be configured to prevent ovalization of the catheter so as to prevent catching of the catheter against an opening formed by the shaft. For example, the space (e.g., difference, shelf) between the inner diameter of the catheter and an outer diameter of the shaft may lead to the catheter compressing to an oval-like shape that may increase the likelihood of the catheter catching against an edge of the tissue opening (e.g., slit), thus preventing the catheter from advancing out of the MMA and into the subdural space. In some embodiments, the shaft may be configured such that a predetermined portion of the shaft may have an outer diameter similar to (e.g., substantially equal to) an inner diameter of a predetermined portion of the catheter so as to render the shelf between the shaft and catheter negligible such that the catheter may maintain a circular (e.g., non-oval) cross-section shape along a predetermined length to facilitate passage through the formed tissue opening. For example, an outer diameter or maximum lateral dimension of the shaft may be increased at a location of a fiducial or radiopaque marker. The radiopaque marker on the shaft can be aligned with a radiopaque marker on a distal end of the catheter, as described above, before advancing the catheter together with the shaft through an opening in a vessel wall or dura. The larger dimension of the shaft at this location can prevent the catheter from ovalizing as it is being advanced through the opening, while minimally impacting the overall increase in friction that would result from a negligible shelf between the shaft and catheter along longer segments. A relatively high overall friction between the shaft and catheter may prevent the rotation (e.g., self-orientation) of the shaft as described herein for directional perforation to the subdural space.

In some embodiments, the shaft 520 may have a predetermined shape at a predetermined portion (e.g., at a focal point along its length) configured to steer the advancing catheter away from a dural edge at an arteriotomy/durotomy site. In some embodiments, the predetermined shape may include one or more of a J-shape, U-shape, C-shape, V-shape, an M-shape, an S-shape, a helix, and combinations thereof. For example, the shape may form a mountain-like shape configured to force an edge away or lift the dura.

In some embodiments, the shaft 520 may include shape memory material (e.g., nitinol) wire having a polymer jacket. As described in more detail herein (e.g., FIGS. 6, 8), the shaft may include a flattened (e.g., pinched) portion configured to self-orient in an intracranial MMA. As described in more detail herein, the different shapes and configurations of the shaft (e.g., J-shaped curve, curve and contra curve, bends, offset, diameter changes) may improve flexibility, pushability, and support.

In some embodiments, the shaft may be formed having a set of constant diameter distal segments and proximal segments having different diameters between about 0.014 inches and 0.025 inches, including all ranges and sub-values in-between.

In some embodiments, the shape memory material of the shaft may have a proximal diameter of about 0.016 inches and about 0.021 inches, including all ranges and sub-values in-between. In some embodiments, the shape memory material of the shaft may have a tapered distal diameter of about 0.060 inches and about 0.014 inches, including all ranges and sub-values in-between.

In some embodiments, the distal segment of the shape memory material may be flattened to a width of about 0.008 inches and about 0.018 inches, including all ranges and sub-values in-between. In some embodiments, the distal segment of the shape memory material may have a thickness of about 0.003 inches and about 0.008 inches, including all ranges and sub-values in-between.

In some embodiments, a shaft may be configured to be slidably disposed within a lumen of a catheter. The shaft may be configured to be advanced distally from a distal end of the catheter and into a blood vessel (e.g., MMA) of a subject. The shaft may include a perforating tip including an energy element. The energy element may be configured to generate RF energy to form an opening through a wall of the blood vessel and dura of the subject and into an extravascular space of the subject. A curved section may be configured to be radially constrained within the lumen of the catheter. The curved section may be configured to curve toward the wall of the blood vessel and the dura upon exiting the lumen of the catheter such that the energy element is positioned to form the opening. A first discontinuity may be disposed between the perforating tip and the curved section. A second discontinuity may be disposed proximal of the curved section. The second discontinuity may be configured to orient the curve to follow a curve of the blood vessel as the shaft is advanced within the lumen of the catheter.

In some embodiments, the first discontinuity may include a bend in the shaft. In some embodiments, the curved section may have a first radius of curvature, and the first discontinuity includes a section of the shaft having a second radius of curvature that is smaller than the first radius of curvature. In some embodiments, the curved section may be configured to transition into a curved configuration as the curved section travels through the opening and into the extravascular space.

In some embodiments, the curved section may have a cross-section with a first lateral dimension that is greater than a second lateral dimension. In some embodiments, the second discontinuity may include a bend in the shaft. In some embodiments, the second discontinuity may include a partial helix or a twist in the shaft. In some embodiments, the curved section may have a first curved section that includes a convex curvature, and the shaft may further include a second curved section proximal of the first curved section. The second curved section may include a concave curvature. In some embodiments, the shaft may include a wider section having a lateral dimension that is equal to or substantially equal to an inner diameter of the lumen of the catheter to prevent ovalizing of the catheter as the catheter advances through the opening. In some embodiments, the opening has a length that is equal or substantially equal to a length of the energy element.

In some embodiments, the shaft may include a first radiopaque element disposed at the perforating tip, and a second radiopaque element disposed proximal of the curved section. The shaft may further include a wider section disposed proximal of the curved section. For example, as described above, the wider section may be configured to prevent ovalizing of the catheter as the catheter is advanced into the extravascular space. The distal end of the catheter may include a first radiopaque element, and the shaft may include a second radiopaque element disposed near the wider section, such that the wider section can be aligned with the distal end of the catheter prior to advancing the catheter into the extravascular space.

In some embodiments, the shaft may include one or more lumens with one or more openings. The one or more lumens may be configured for one or more of fluid injection and aspiration (e.g., for coupling). For example, injection of a non-ionic dextrose through a first lumen during RF energy delivery may reduce or eliminate alternative current paths and results in more efficient vaporization of a target tissue. A second lumen may be configured to provide aspiration (e.g., suction) to improve wall apposition to the RF electrode and/or collapse an arterial vessel during RF mediated arterial occlusion. In some embodiments, a proximal end of the shaft may be coupled to a signal generator (e.g., RF generator) via a pushbutton electrosurgical pencil.

Distal Tip Portion

In some embodiments, a perforating element 524 of a shaft 520 may include an electrode (e.g., RF ablation tip). Delivery of RF energy using an electrode may rapidly increase tissue temperature to convert fluid to steam (e.g., vaporization), resulting in focal tissue disruption and void. Vaporization may result in a fenestration from the vascular lumen (and through the dura) to the intradural compartment.

In some embodiments, penetration of the dura presents is achieved with mechanical (e.g., cutting) elements. A needle penetration force of between 0.29 to 1.29 N (0.68±0.24 N) may be required to penetrate the dura such that dura is a very resistant tissue requiring both high sharpness and strong penetrating forces. However, sharp needle tips may result in catheter skiving or scratching along curvatures and unintended brain perforation. Furthermore, high penetration forces require high catheter column strength and pushability, which are obtained by using stiff materials and construction that oppose the strength and pushability requirements for navigating a catheter through tortuous vascular geometry.

RF tissue ablation without mechanical cutting may allow the shaft 520 to have reduced column strength compared to mechanical cutters such as needles that require high pushability. Furthermore, an atraumatic perforating element may be less likely to damage a catheter 510 relative to a shaft having a needle tip. Ablation resulting in voided tissue may also reduce edge catching as a catheter 510 is advanced through the tissue opening.

In some embodiments, RF energy may be used to facilitate ingress into a hematoma through one or more of the surrounding membranes, perforation of septations associated with mixed-aged SDH and chronic SDH, and unclogging of a catheter. Furthermore, RF energy may be used to coagulate tissue to facilitate one or more of tissue opening formation and closure.

In some embodiment, the perforating element 524 may include two or more electrodes. For example, the perforating element 524 may include two or more tubular elements. In some embodiments, a plurality of electrodes may be connected individually in parallel to a signal generator 560 in a monopolar configuration and share the same grounding pad. In another embodiment, a first electrode may be connected to the signal generator 560 and a second electrode may be connected to ground in a bipolar configuration. In a bipolar configuration, the current may be concentrated between the first and second electrode.

In some embodiments, the perforating element 524 may include a first electrode and the catheter 510 may include a second electrode in a bipolar configuration. In this configuration, the perforating element 524 and the catheter 510 may be advanced concurrently to maintain the current delivered to tissue, or the perforating element 524 may be advanced relative to the catheter 510 to reduce current delivery as tissue is disrupted and decrease the likelihood of brain injury.

In some embodiments, the perforating element 524 may include platinum iridium, stainless steel, copper, titanium, and nickel-titanium alloys and be configured as a fluoroscopic marker and RF electrode. The perforating element 524 may have an atraumatic shape (e.g., tubular, blunt, rounded distal end). For example, the perforating element 524 may have a shape including one or more of a bullet, a cone, a truncated cone, a cylinder, a sphere, a dome, a ring, a semi-annular shape, an ellipse, a bevel, and an arrowhead. In some embodiments, an electrode of the perforating element 524 may be uninsulated or partially insulated and may be made of and/or coated with a conductive and a biocompatible material with high radiopacity such as stainless steel, silver, gold, platinum, combinations thereof, and the like. In such embodiments, the shaft may be covered with an insulating material along its length, with the electrode at its distal end being uninsulated or covered in a conductive material. In some embodiments, an uninsulated portion of the perforating element 524 may have an area of less than about 16 $mm^2$. In some embodiments, the perforating element 524 may have a length of between about 1.3 mm and about 1.7 mm, including all ranges and sub-values in-between. In some embodiments, a distal end of the perforating element 524 may be open or closed. In some embodiments, the perforating element may be tapered.

Hemostatic Device

In some embodiments, the hemostatic device 530 include a hemostatic element or an RF device configured to close an opening formed by the perforating element 524 of the shaft 520. The hemostatic device 530 may be optionally coupled to the signal generator 560. In some embodiments, the catheter 510 may be configured to deliver the hemostatic device 530 to the location of an opening through a vessel wall and/or dura, (e.g., to seal the opening).

Linear RF Device

In some embodiments, the catheter 510 may be configured to deliver a linear RF device to an opening in a vessel wall and/or dura, as well as to a subdural hematoma. For example, a catheter assembly may include a second RF device including a linear tip configured to penetrate through a membrane of a subdural hematoma. This may facilitate ingress and egress of a catheter (e.g., aspiration catheter) into a SDH. For example, the linear tip may include an RF electrode configured to operate in a monopolar configuration. In some embodiments, the second RF device may be configured to deliver RF energy to close a vascular lumen of the blood vessel. For example, when the catheter has been withdrawn from an extravascular space and into a blood vessel (e.g., MMA), the second RF device may be used to seal the opening formed in the MMA. As such, this second RF device can function as a hemostatic device.

In some embodiments, the linear RF device may be configured in a monopolar or bipolar configuration, single or a plurality of bipolar configuration. In some embodiments, the linear RF device may have a shape corresponding to a ring or a coiled configuration for circumferential thermal ablation. In some embodiments, the coiled configuration may be disposed at a distal end of the linear RF device and have a length of between about 3 mm and about 30 mm, and a diameter of between about 0.02 inches and about 0.03 inches, including all ranges and sub-values in-between. In some embodiments, the diameter may be continuous or tapered.

In some embodiments, the linear RF device may include a temperature sensor such as a thermistor and a thermocouple. In some embodiments, the temperature sensor may be thermally isolated from the RF electrode.

Sensors

In some embodiments, one or more sensors 540 may be coupled to one or more of the catheter 510, shaft 520, and hemostatic device 530. Sensors 540 may be configured to measure one or more parameters including, but not limited to, pressure and impedance. The sensor measurements may be used by one or more of an operator and signal generator during a procedure. For example, pressure measurements may indicate to the operator the location and/or orientation of a shaft 520 of the catheter assembly 502 while RF energy may be delivered to a perforating element 524 only when a measured impedance is within a predetermined range so as to prevent damage to brain tissue.

In some embodiments, a pressure sensor may comprise one or more of a potentiometric pressure sensor, an inductive pressure sensor, a capacitive pressure sensor, a strain gauge pressure sensor, a fiber optic pressure sensor, a variable reluctance pressure sensor, a micro-electromechanical system pressure sensor, and a piezoelectric pressure sensor. For example, a piezoelectric pressure sensor may include a piezoelectric film disposed along an outer diameter of a perforating element in proximity to the distal end. The measured signal may include a peak pressure value associated with penetration through the MMA wall followed by a pressure drop associated with access to the subdural space. In some embodiments, a pressure sensor may be configured to measure a pressure waveform (e.g., arterial, intracranial, or venous perforation waveforms) upon penetration from the vascular lumen into the intracranial compartment. In some embodiments, tissue spectroscopy values may be measured to monitor perforation and access into the subdural space.

In some embodiments, a first pressure sensor may be disposed at or adjacent a distal end of the perforating element and configured to measure pressure against tissue and/or fluid. A second pressure sensor may be disposed proximal to the first pressure sensor (e.g., about 0.2 mm and about 2 mm from the first pressure sensor). First and second pressure sensor measurements when the perforating element is advanced through a blood vessel correspond to the nominal blood pressure. When the perforating element contacts a wall of a blood vessel, the first pressure sensor measurement corresponding to the vessel wall may be higher than the second pressure measurement corresponding to the blood pressure. During tissue perforation, the first pressure sensor measurement may be lower than the second pressure measurement. After formation of an opening in the vessel wall, the first and second pressure measurements may correspond to the fluid pressure of the subdural space.

In some embodiments, an impedance sensor may be configured to measure impedance, permittivity, and/or conductivity) of tissue and fluid to monitor perforation and access into the subdural space. Changes in impedance (or other dielectric property) between an artery, dura, fluid (e.g., contrast fluid, cerebrospinal fluid, subdural hematoma), intradural space, and the brain may indicate the location and of the perforating element throughout a procedure. Impedance measurements may be used to control energy delivery by the signal generator. For example, energy delivery may be modified to optimize a cut and be stopped based on the measured impedance.

In some embodiments, a temperature sensor may be configured to measure a temperature of tissue and fluid. For example, the temperature sensor may include a thermocouple disposed at or adjacent a distal end of the perforating element. The measured temperature may be used to control waveform delivery (e.g., impedance, voltage, duty cycle, pulse width) by the signal generator. For example, energy delivery may be modified to optimize and cut and stopped if the measured temperature exceeds a predetermined threshold in order to prevent unintended tissue damage.

In some embodiments, the perforating element 524 (e.g., electrode) may be configured to measure an electroencephalographic (EEG) signal disposed within about 20 mm from a distal end of the perforating element 524. The perforating element 524 may be configured to alternately deliver RF energy and measure an EEG signal, impedance signa, and the like.

In some embodiments, a force sensor disposed on or adjacent a perforating element may be configured to measure a force associated with penetration of the shaft through the MMA and dura. For example, pressure may be measured using a pressure transducer disposed outside the subject.

Vacuum Source

In some embodiments, the vacuum source 550 may be coupled to the catheter 510. The vacuum source 550 may be configured to provide negative pressure (e.g., suction) to a lumen of the catheter 510. The suction generated by the vacuum source 550 may be configured to remove fluid and matter (e.g., from a subdural hematoma) through the lumen of the catheter 510. In some embodiments, the vacuum source may include one or more of a pump and syringe. The vacuum source 550 may be configured to operate in one or more modes including continuous, dynamic, cyclical, pulsatile, low frequency, high frequency, combinations thereof, and the like.

Signal Generator

Generally, the signal generators described here may be configured to provide energy (e.g., energy waveforms) to a perforating element to form an opening in tissue. In some embodiments, the signal generator 560 may be coupled to one or more of the shaft 520 and the hemostatic device 530. In particular, the signal generator 560 may be configured to generate energy for delivery using the perforating element 524 of the distal tip portion 522. The signal generator 560 may include a processor 562, a memory 564, and an input/output device 566 configured to control the signal generator 560 and provide appropriate energy waveforms for tissue ablation and to ensure patient safety. In some embodiments, the signal generator may be configured to control waveform generation and delivery in response to received sensor data. For example, energy delivery may be inhibited unless an impedance sensor measurement confirms a tissue type to be ablated.

The signal generator may generate and deliver several types of signals including, but not limited to, RF, pulsed field ablation, microwave, diathermy, laser, and electrocautery. For example, diathermy, laser and electrocautery waveforms may be used to cut and or coagulate the membranes surrounding the subdural hematoma, the septations inside the hematoma, or any bleeding source. Diathermy, laser and electrocautery waveforms may also be used to close the transvascular passageway and a vascular lumen such as the MMA. In some embodiments, a monopolar or bipolar cautery may be separate from or integrated with the catheter and/or shaft. In some embodiments, one or more of the shaft and catheter may be coupled with thermoablation. For example, the signal generator may generate monophasic (DC) pulses and biphasic (DC and AC) pulses. The signal generator may comprise a processor, memory, energy source, and user interface. The processor may incorporate data received from one or more of memory, energy source, user interface, and catheter assembly. The memory may further store instructions to cause the processor to execute modules, processes and/or functions associated with the system, such as waveform generation and delivery. For example, the memory may be configured to store patient data, clinical data, procedure data, and the like. In some embodiments, the signal generator may be configured to generate a waveform in a range between about 250 kHz and about 750 kHz, and about 120 V and about 400 V, including all ranges and sub-values in-between. In some embodiments, the signal generator may be configured to generate an ablation waveform (e.g., cutting waveform) in a range between about 1 W and about 300 W, including all ranges and sub-values in-between. For example, a transvascular opening between a lumen of an MMA and a subdural space may be formed by the signal generator generating an ablation waveform including a power of between about 15 W and about 60 W, a duty cycle of at least about 300 ms, and for a duration of less than about 5 seconds, including all ranges and sub-values in-between. For example, the ablation waveform may be generated for less than about 2 seconds.

Generally, the processor (e.g., CPU) described here may process data and/or other signals to control one or more components of the system. The processor may be configured to receive, process, compile, compute, store, access, read, write, and/or transmit data and/or other signals. In some embodiments, the processor may be configured to access or receive data and/or other signals from one or more of a sensor (e.g., impedance sensor, pressure sensor) and a storage medium (e.g., memory, flash drive, memory card). In some embodiments, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the ablation device described here may comprise a memory configured to store data and/or information. In some embodiments, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory may store instructions to cause the processor to execute modules, processes, and/or functions such as signal waveform generation, system control, data and/or signal transmission, data and/or signal reception, and/or communication. Some embodiments described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some embodiments, the system may further comprise a communication device configured to permit an operator to control the system. The communication device may comprise a network interface configured to connect the system to another system (e.g., Internet, remote server, database) by wired or wireless connection. In some embodiments, the system may be in communication with other devices (e.g., cell phone, tablet, computer, smart watch, and the like) via one or more wired and/or wireless networks. In some embodiments, the network interface may comprise one or more of a RF receiver/transmitter, an optical (e.g., infrared) receiver/transmitter, and the like, configured to communicate with one or more devices and/or networks. The network interface may communicate by wires and/or wirelessly with one or more of the system, network, database, and server.

The network interface may comprise RF circuitry configured to receive and/or transmit RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some embodiments, the devices herein may directly communicate with each other without transmitting data through a network (e.g., through NFC, Bluetooth, WiFi, RFID, and the like).

In some embodiments, the input device (e.g., keyboard, buttons, touch screen) and output device (e.g., display device) may be configured to receive input data from one or more of the system, network, database, and server. For example, operator control of an input device (e.g., keyboard, buttons, touch screen) may be received by the input/output device and may then be processed by processor and memory for the user interface to output a control signal to the system. Some embodiments of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In embodiments of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio data and recognize an operator voice as a control signal.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). As another example, haptic feedback may notify that operator input is overridden by the system.

Visualization Device

In some embodiments, the visualization device 570 may be configured to visualize (e.g., generate one or more images) corresponding to one or more components of the catheter assembly 502 (e.g., catheter 510, shaft 520, hemostatic device 530) disposed within the subject. As described in more detail herein, the visualization device 570 may facilitate positioning of the catheter assembly 502 within the intravascular and extravascular spaces of the subject (e.g., orientation and placement of the distal tip portion 522 and perforating element 524 relative to the blood vessel).

In some embodiments described herein, one or more elements of the catheter assembly 502 (e.g., catheter 510, shaft 520, hemostatic device 530) may include a set of fiducials (e.g., radiopaque elements) spaced along a length of the catheter assembly 502 (e.g., catheter 510, shaft 520) and configured to be imaged by the visualization device. For example, the set of fiducials may include radiopaque fluoroscopic markers (FM).

In some embodiments, a radiopaque element may include one or more of gold, platinum, platinum iridium, tantalum, bismuth, tungsten-filled polymers, combinations thereof, and the like. In some embodiments, a fiducial may be disposed at proximal end of a perforating element 524 to indicate a relative location of a distal end of the perforating element 524. In some embodiments, a fiducial may be configured to indicate rotational orientation.

For example, visualization may include one or more of optical coherence tomography (OCT) and intravascular ultrasound (IVUS) tomography. With respect to IVUS, dura, dural appendages, cerebrospinal fluid, brain superficial pia mater, cortical gray matter, and white matter are hyperechoic. The subarachnoid space contains numerous vessels visible on a Doppler mode of ultrasound. The subdural collection may have hyperechoic membranes, and may be hyperechoic, hypoechoic, or a combination thereof.

In some embodiments, visualization may include a combination of invasive (e.g., US, CTO, angioscopy) and non-invasive (fluoroscopy, US, CT, MR) imaging modalities. In some embodiments, the catheter 510 may include an optical sensor (e.g., camera) and/or light source for endoscopic visualization of one or more of catheter advancement in a subdural or epidural space, and transvascular drainage of subdural collection. In some embodiments, the optical sensor may include one or more of an optical fiber, a complementary-symmetry metal-oxide-semiconductor, a scanning fiber endoscope, combinations thereof, and the like.

Example Embodiments

Figure 6:
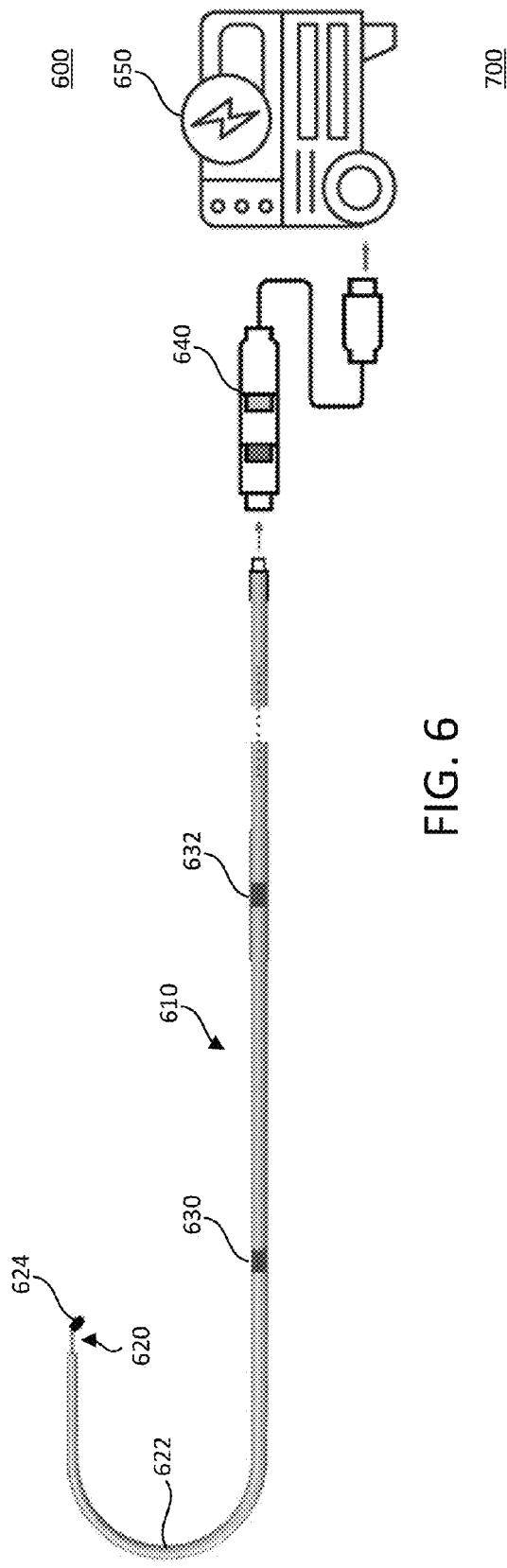
FIG. 6 is a schematic diagram of a system, according to embodiments.

FIG. 6 is a schematic diagram of a system 600 including a catheter 610, shaft 620, connector 640, and a signal generator 650. The catheter 610 and shaft 620 may include components that are structurally and/or functionally similar to the catheter 510 and shaft 520, respectively, as described above with reference to FIG. 5. The system 600 may be configured to form an opening between a blood vessel to an extravascular space of a subject and/or deliver a hemostatic element or an RF device to close an opening formed by the shaft 620. In some embodiments, the catheter 610 may be slidably disposed within a lumen of a sheath.

In some embodiments, the shaft 620 may be coupled to the signal generator 650. The shaft 620 may include a distal tip portion 622 having a perforating element 624 configured to create (e.g., form) an opening in a wall of a blood vessel and a dura of the subject. In some embodiments, the distal tip portion 622 may have a predetermined shape, such as, for example, a J-shaped curve, as further described below. Alternatively, in some embodiments, the distal tip portion 622 can have a different predetermined or preset shape, e.g., a U-shape, a C-shape, or other atraumatic shape. In some embodiments, the shaft 620 (e.g., distal tip portion 622) may further include an offset (not shown) configured to orient the shaft 620 in a predetermined orientation when the shaft 620 is advanced within the lumen of the catheter 610 and a blood vessel. For example, the offset may be configured to rotate (e.g., self-orient) the distal tip portion 622 about a longitudinal axis of the shaft 620 such that the perforating element is directed toward the dura and brain while a proximal portion of the J-shaped distal tip portion faces the skull, thereby ensuring that the opening created by the perforating element 630 is formed within an arc that faces the subdural space and not the skull.

As described in more detail herein, the shaft 620 may generally have a rounder cross-sectional shape (e.g., circular or oval) while the offset may have a relatively flatter ovoid cross-sectional shape configured to rotate or twist the distal tip portion 622 to a desired orientation (e.g., facing away from the skull and towards the dura) when advanced through tortuous vasculature. The J-shaped curve of the distal tip portion 622 may be advantageous in facilitating atraumatic advancement of the shaft 620 through a subdural space. The J-shaped curve may be constrained as the shaft is advanced through vasculature, but may naturally form within a subdural space after the shaft 620 creates an opening through a blood vessel and dura. A distal end of the distal tip portion 622 may include a perforating element 630 such as an electrode configured to deliver RF energy. In some embodiments, the perforating element 630 may be angled relative to the distal tip portion 622.

In some embodiments, the connector 640 may be configured to couple the catheter 610 and shaft 620 to the signal generator 650 and a vacuum source (not shown). In some embodiments, the signal generator 650 may be coupled to the shaft 620. In particular, the signal generator 650 may be configured to generate energy (e.g., RF energy) for delivery using the perforating element 624 of the distal tip portion 622.

In some embodiments, the catheter 610 and/or shaft 620 may include a set of fiducials including a first fiducial 630 and a second fiducial 632 configured to by imaged and facilitate positioning of the system 600 within the intravascular and extravascular spaces of the subject.

Figure 7A:
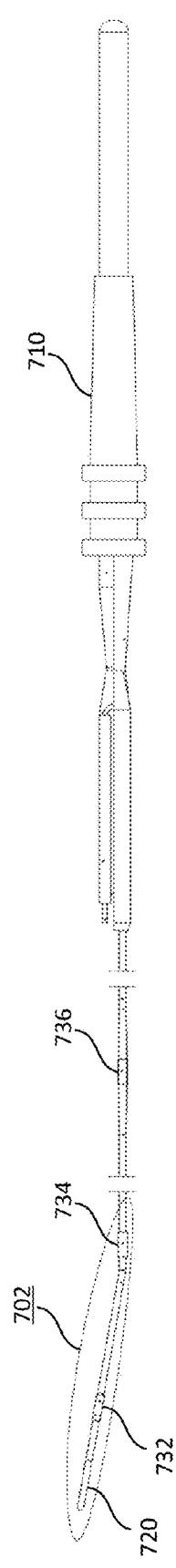
Figure 7B:
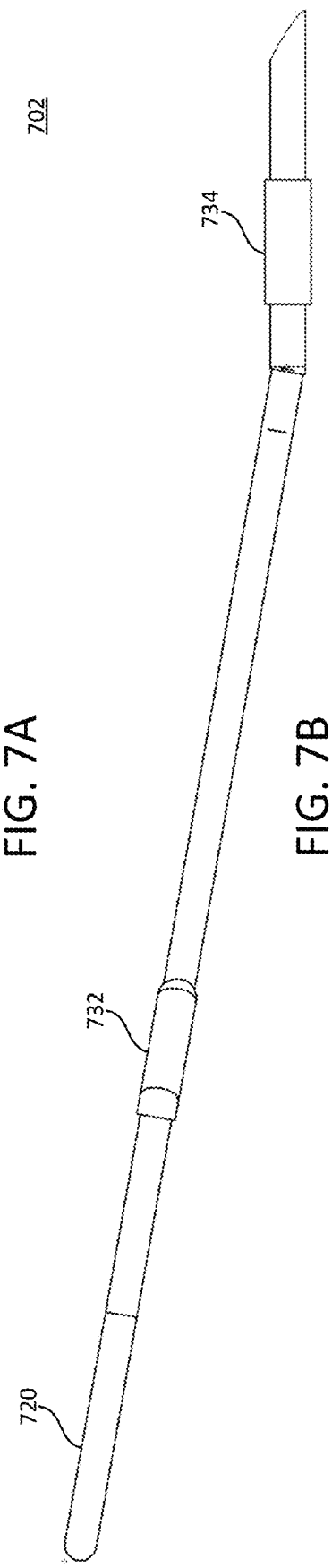

FIGS. 7A and 7C are schematic diagrams of a shaft assembly 700, 704 and FIGS. 7B, 7D, and 7E are detailed schematic diagrams of the shaft assembly 702, 706, 708 depicted in FIGS. 7A and 7C, respectively. The shaft assembly 700-708 may include components that are structurally and/or functionally similar to the shaft 520, 620 respectively.

The shaft assembly 700, 702 shown in FIGS. 7A and 7B may include a handle 710, a perforating element 720, a first fiducial 732, a second fiducial 734, and a third fiducial 736.

In some embodiments, the first fiducial 732 corresponds to a location of the perforating element 720, the second fiducial 734 facilitates confirmation of shaft self-orientation, and the third fiducial 736 corresponds to the location of the largest outer diameter of the shaft. In some embodiments, the perforating element 720 and first fiducial 732 may form an angle with respect to the second fiducial 734 of between about 5° and about 15°, including all ranges and sub-values in-between. In some embodiments, the bent portion of the shaft assembly formed by the perforating element 720 and first fiducial 732, as shown in FIG. 7B, may have a length extending along a longitudinal axis of the shaft assembly 700 between about 2.3 cm and about 2.7 cm, including all ranges and sub-values in-between.

The shaft assembly 704, 706 shown in FIGS. 7C and 7D further depict a distal tip portion 740 of the shaft. The distal tip portion 740 may have a perforating element 720 configured to create (e.g., form) an opening in a wall of a blood vessel and a dura of the subject. In some embodiments, the distal tip portion 740 may have a predetermined shape such as a J-shaped curve. A distal end of the distal tip portion 740 may include the perforating element 720 such as an electrode configured to deliver RF energy. In some embodiments, as shown in FIGS. 7C and 7D, the perforating element 720 may be angled relative to the distal tip portion 740. While disposed within a vessel (e.g., MMA), the shape of the distal tip portion 740 may be constrained by the vessel such that the J-shape is not formed within the vessel. Once the distal tip portion 740 is advanced out of an opening in the vessel and dura, the unconstrained shape of the distal tip portion 740 may be formed. In some embodiments, the set of fiducials 732, 734, 736 may be configured to be imaged (e.g., visualized) to facilitate positioning of the shaft assembly 700-708 within the intravascular and extravascular spaces of the subject.

In some embodiments, the shaft may have a length of at least about 170 cm from a femoral or a radial access point. The shaft may be shorter when using a cervical access point. In some embodiments, the perforating element 720 may be angled towards the shaft to concentrate energy delivery by the perforating element 720 to tissue at a contact point in order to vaporize tissue and minimize heat generation and tissue shrinkage. Additionally or alternatively, higher energy levels that vaporize (e.g., ablate) more tissue may be used to create a transvascular passageway (e.g., when the perforating element 720 does not include a contact point that focuses energy delivery). In some embodiments, as shown in FIGS. 7C and 7D, the perforating element 720 may form an angle with respect to a distal end of the distal tip portion 740 of between about 25° and about 35°, including all ranges and sub-values in-between.

In some embodiments, a height of the curved portion of the distal tip portion may be between about 0.6 cm and about 0.8 cm, including all ranges and sub-values in-between. In some embodiments where the shaft forms a J-shape such as in FIGS. 7C and 7D.

The perforating element 720 may have an angle and length configured to provide depth-controlled perforation of an MMA and dura but not the brain. In some embodiments, a distance between a distal end of the perforating element 730 and a distal end of the shaft (e.g., defined by the curved portion of distal tip portion 740) may be between about 1 cm and about 1.4 cm, including all ranges and sub-values in-between.

In some embodiments, an outer diameter of the shaft may vary along its length in a predetermined manner. For example, the shaft may have a first outer diameter 733 and a second outer diameter 735 larger than the first outer diameter 735. In some embodiments, a first outer diameter 733 of the shaft may generally be between about 0.020 inches and about 0.027 inches, including all ranges and sub-values in-between. A second outer diameter 735 of the shaft may generally be between about 0.0255 inches and about 0.0270 inches, including all ranges and sub-values in-between. The outer diameter of the shaft may taper from the first outer diameter 733 to the second outer diameter 735 and back to the first outer diameter 733, as shown in FIG. 7E, for a length of between about 4 mm and about 6 mm, including all ranges and sub-values in-between. In some embodiments, a first fiducial 732 (e.g., distal most fiducial) may have the second outer diameter 735 while the rest of the shaft has the first outer diameter 733.

In some embodiments, the second outer diameter may substantially match (e.g., within 0.002 inches) an inner diameter of a corresponding catheter so as to reduce and/or restrict longitudinal advancement of the shaft relative to the catheter. This may aid parallel advancement of the shaft and catheter through a subdural space where the shaft and catheter are fixed relative to each other.

Figure 8A:
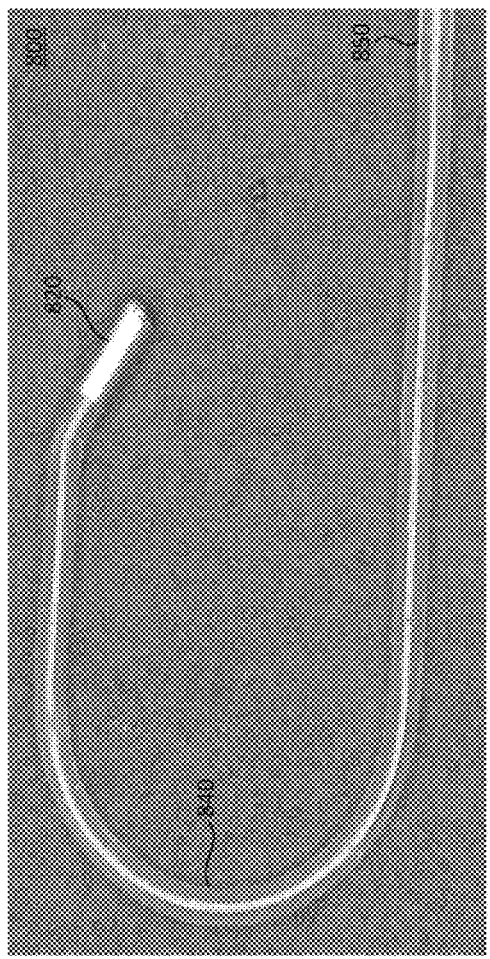
FIGS. 8A-8C are images of a shaft, according to embodiments.
Figure 8B:
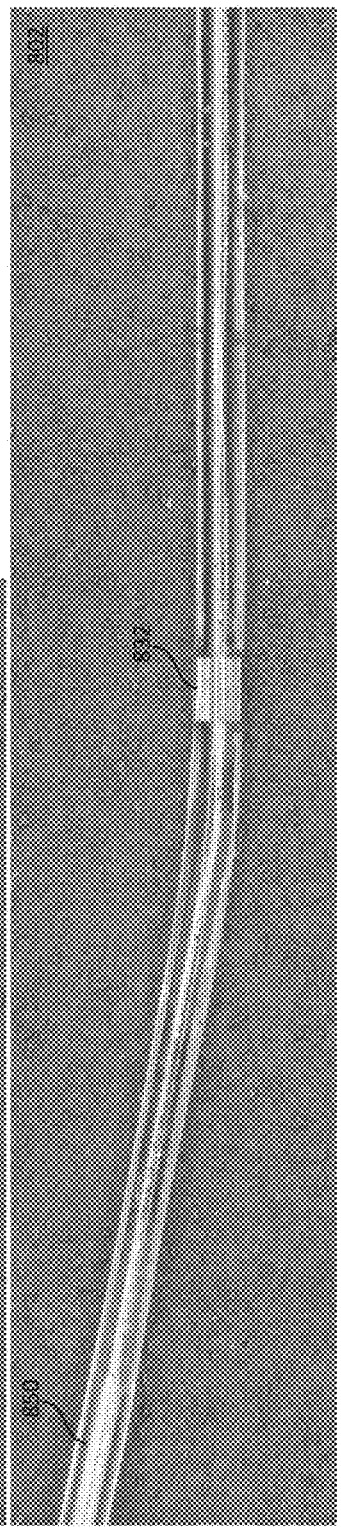
Figure 8C:
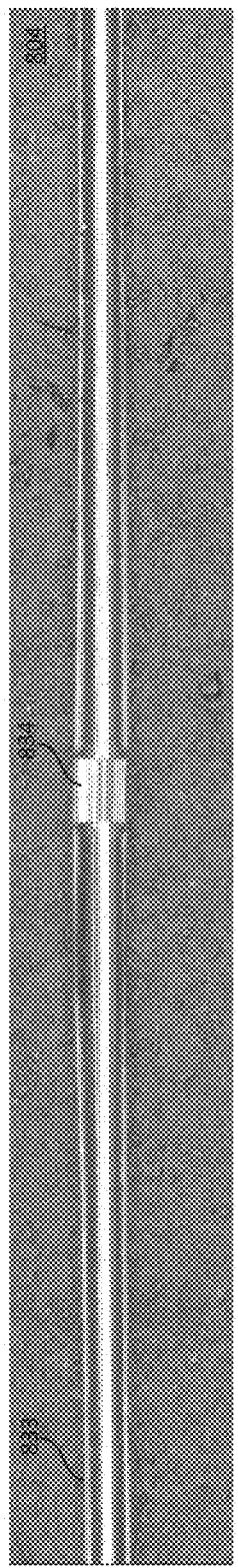

FIGS. 8A-8C are images of different portions of a shaft 800, 802, 804. The shaft 800-804 may include components that are structurally and/or functionally similar to the shaft 520, 620, 700-708 described herein. The shaft 800 shown in FIG. 8A may include a distal tip portion 840 and perforating element 820 attached to a distal end thereof. In some embodiments, the perforating element 820 may form an angle with respect to the distal tip portion 840 as described herein. The perforating element 820 may include an electrode configured to deliver RF energy. As shown in FIG. 8A, the distal tip portion 840 may generally have a J-shaped curve.

The shaft 802 shown in FIG. 8B illustrates a portion of the shaft between a distal end of the shaft 800 and a proximal portion of the shaft 804. The shaft 802 may include a first fiducial 832 and an offset 850 configured to orient at least the distal tip portion 840 of the shaft in a predetermined orientation when the shaft is advanced within a blood vessel. For example, the offset 850 may have a relatively flatter ovoid cross-sectional shape relative to the rest of the shaft where the offset 850 may be configured to rotate or twist the distal tip portion 840 and perforating electrode 820 when advanced through angled vasculature. The flatter shape of the offset 850 may be configured to bends in one plane over another.

In some embodiments, the first fiducial 832 may be located at a predetermined distance from a distal end of the shaft 804 corresponding to a minimum length needed by the shaft 804 to advance past the *foramen spinous* for the offset 850 to self-orient by rotating about a longitudinal axis of the shaft 804. The location of the first fiducial 832 may be determined empirically and/or based on a subject's anatomy (e.g., CT scan data of bony MMA groove). Additionally or alternatively, the shape of the distal tip portion 840 may be modified based on the subject's anatomy. FIG. 8C depicts a proximal portion 804 of the shaft including a second fiducial 834 having a second outer diameter larger than a first outer diameter 833 of the shaft.

Figure 9:
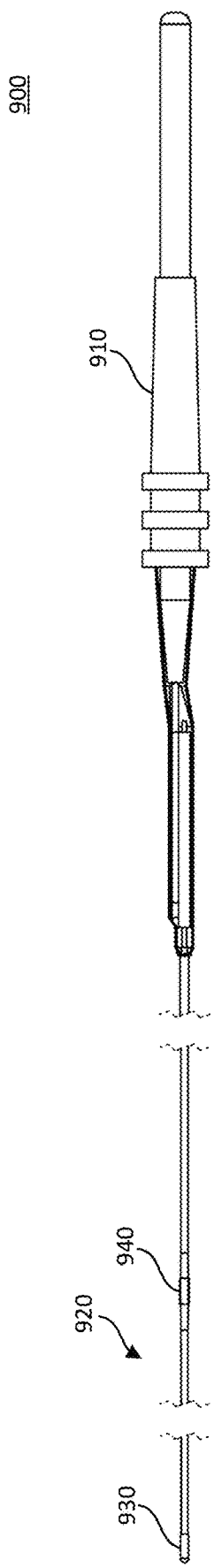
FIG. 9 is a schematic diagram of a shaft, according to embodiments.

FIG. 9 is a schematic diagram of a shaft assembly 900. The shaft assembly 900 may include components that are structurally and/or functionally similar to the shaft 520, 620, 700-708, 800-804 described herein. The shaft assembly 900 may include a handle 910 and a shaft 920. The shaft 920 may include a perforating element 930 and a fiducial 940. The perforating element 930 may be configured to create (e.g., form) an opening in a wall of a blood vessel and a dura of the subject. The shaft 920 is shown in FIG. 9 having a straight configuration. The fiducial 920 may be configured to be imaged (e.g., visualized) to facilitate positioning of the shaft assembly 900 the intravascular and extravascular spaces of the subject.

II. Methods

Also described here are methods for accessing an extravascular intracranial space to enable transvascular surgery without opening the skull using the systems and devices described herein. In particular, the systems and devices described herein can be configured to facilitate removal of fluid (e.g., SDH). Methods of using such systems and devices can include, for example, positioning a catheter disposed within an intracranial vessel of a subject, advancing a shaft through a lumen of the catheter such that a curved section of the shaft curves in a direction along a curve of the vessel, extending the curved section of the shaft out of the catheter such that the curved section curves toward a wall of the vessel, activating a RF element to deliver RF energy to the wall of the vessel to create an opening through the wall of the vessel and dura of the subject and into an extravascular intracranial space, and advancing the shaft and catheter into the extravascular intracranial space. In some embodiments, suction may be applied to the lumen of the catheter to remove fluid from a subdural hematoma. The catheter may be retracted back toward the opening in the artery, and a hemostatic element or an RF device may be delivered to close the opening.

Figure 18:
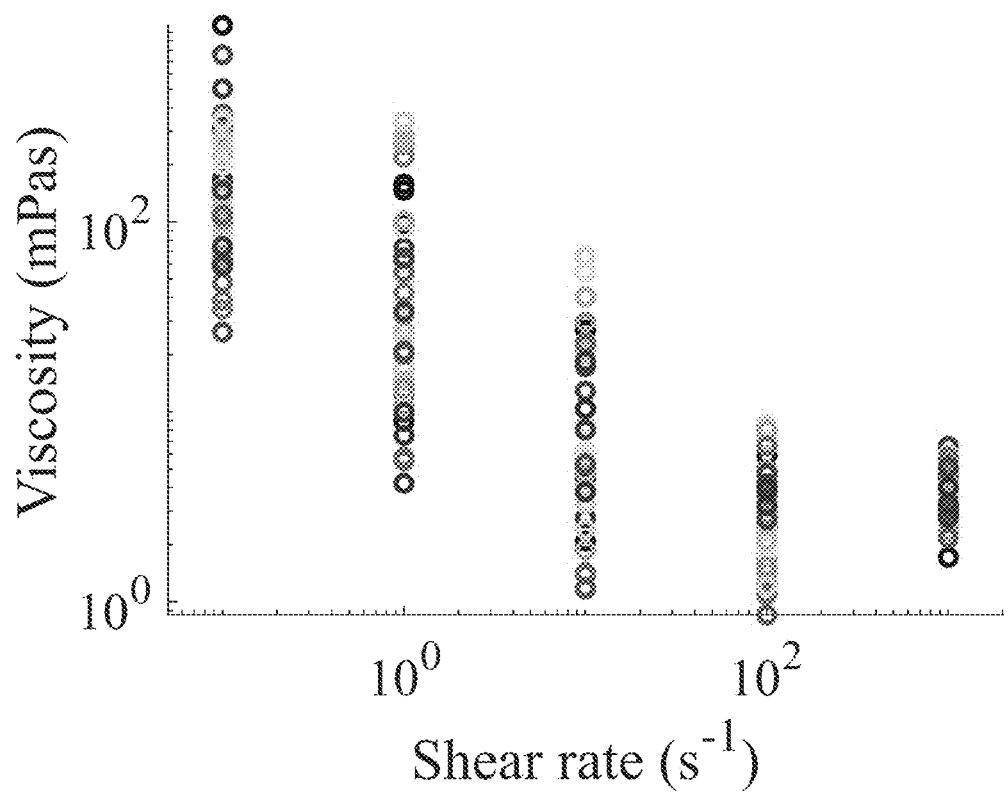
FIG. 18 is a plot of fluid shear rate and blood viscosity, according to embodiments.

The viscosity of SDH fluid is conventionally considered too thick for suction through a catheter having the small diameter necessary to navigate the MMA. However, rheologic analysis of a cohort of cSDH samples empirically demonstrates that the catheters described herein can consistently drain cSDH fluid, as depicted in the plot of FIG. 18 showing fluid shear rate against blood viscosity. In particular, a set of 43 SDH samples from 35 subjects undergoing burr hole surgical drainage was obtained. Viscosity was measured at variable shear rates of about $0.1~s^{-1}$, about $1.0~s^{-1}$, about $10.0~s^{-1}$, about $100.0~s^{-1}$ and about $1000.0~s^{-1}$. Variable shear rate was used as the samples are non-Newtonian fluids where viscosity is shear rate dependent. The empiric flow rate of each sample was measured through a 0.027 inch inner diameter catheter as it can be consistently advanced into the intracranial MMA trunk.

Figure 19A:
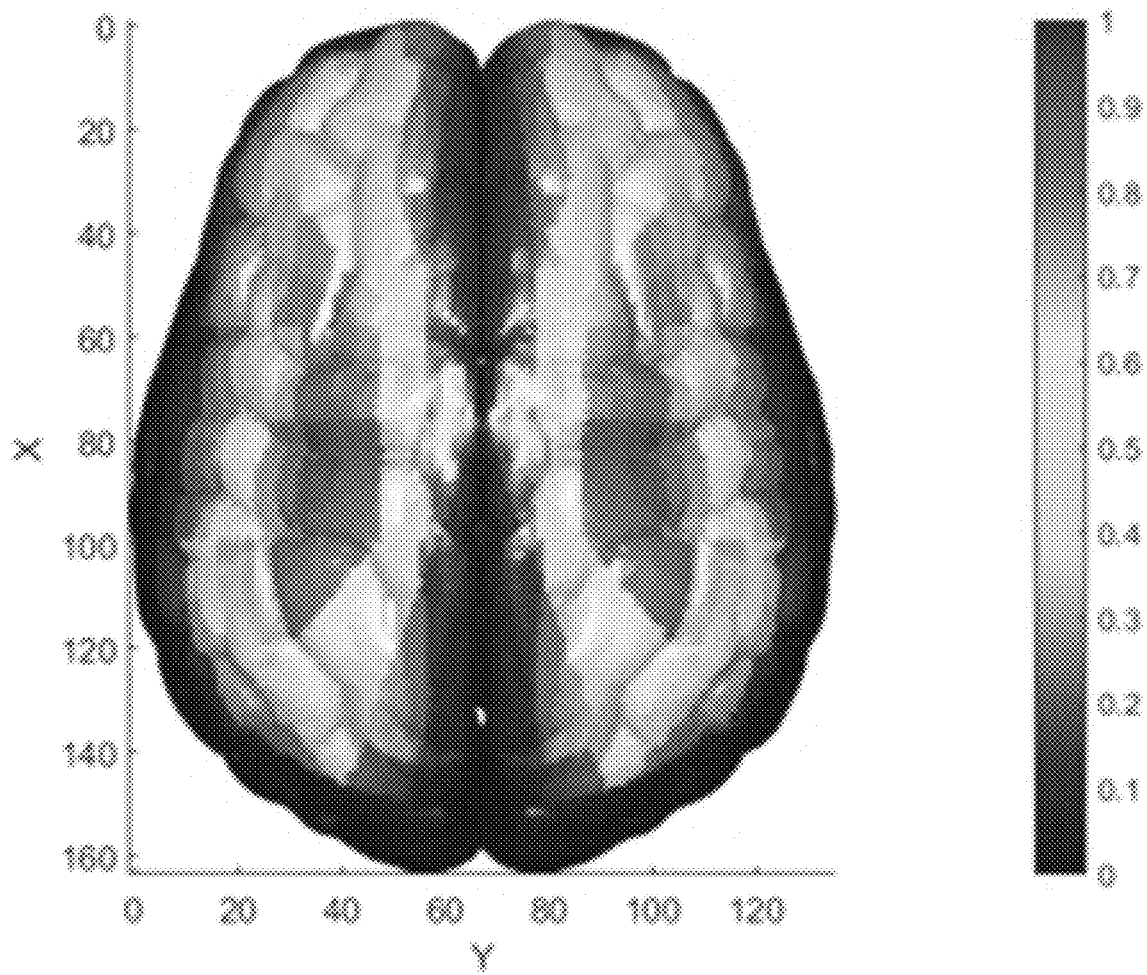
FIG. 19A is a superior view of a hematoma heat map.
Figure 19B:
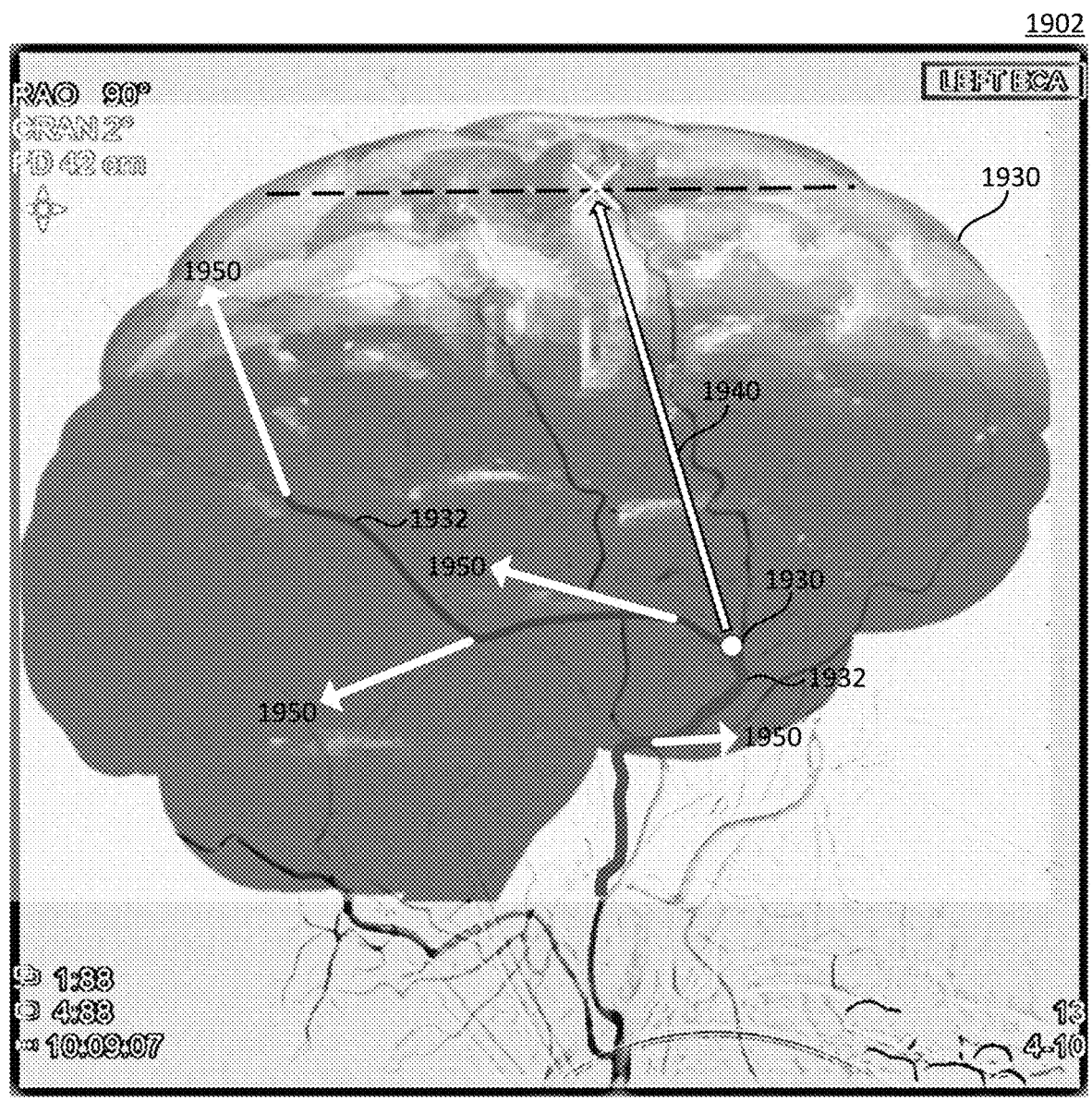
FIG. 19B is an overlay of a hematoma heat map and a set of arterial perforation trajectories, according to embodiments.
Figure 19C:
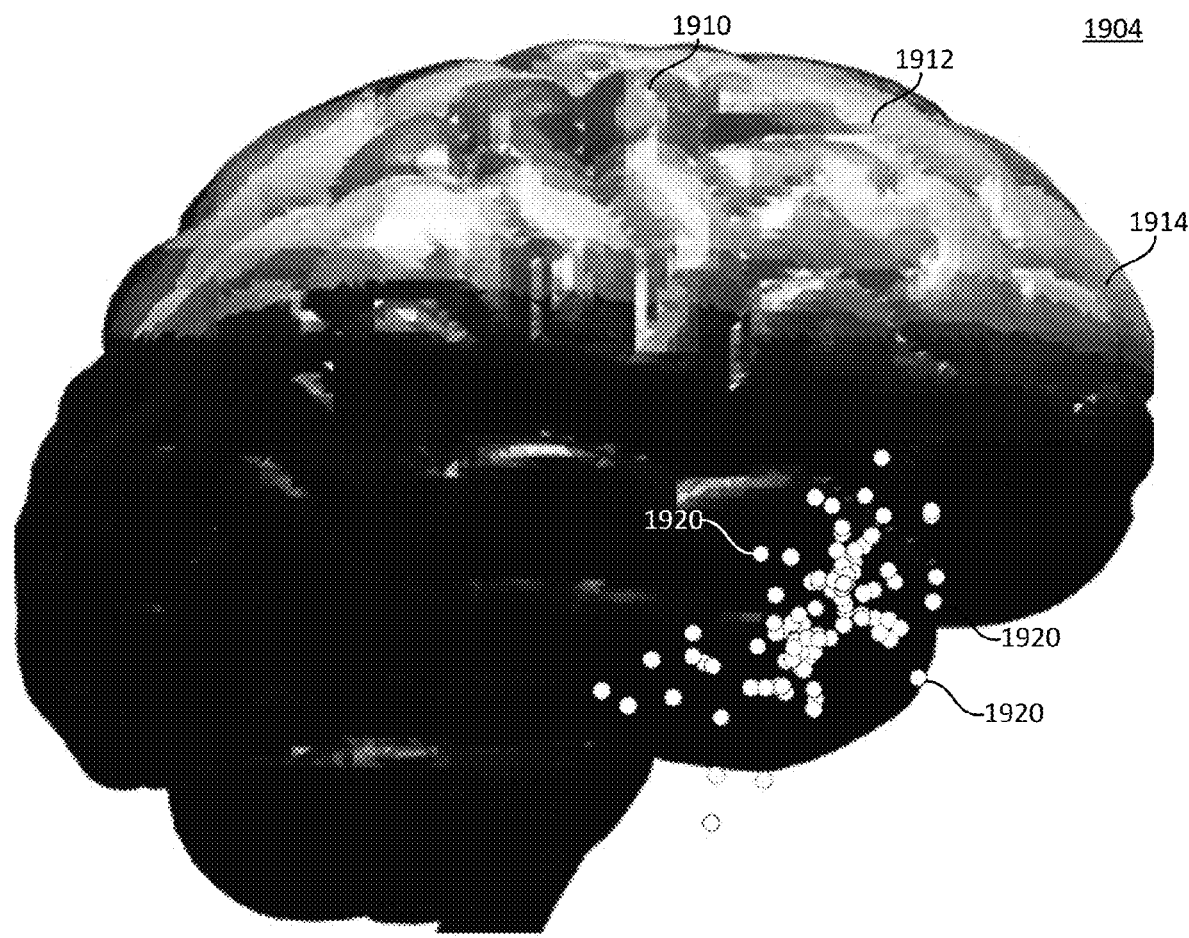
FIG. 19C is an overlay of a hematoma heat map and a set of arterial perforation locations, according to embodiments.

FIGS. 19A-19C depict views of a topographic heat map representing the probability of a hematoma located over the brain surface based on non-contrast head CTs of a cohort of 71 subjects with cSDH. FIG. 19A is a superior view of a hematoma heat map 1900. The legend denotes the probability on a scale from 0 to 1 increments of 0.1, and units of millimeters for x and y. FIG. 19B is an overlay of a hematoma heat map 1902 and a set of arterial perforation trajectories 1940, 1950.

Figure 15B:
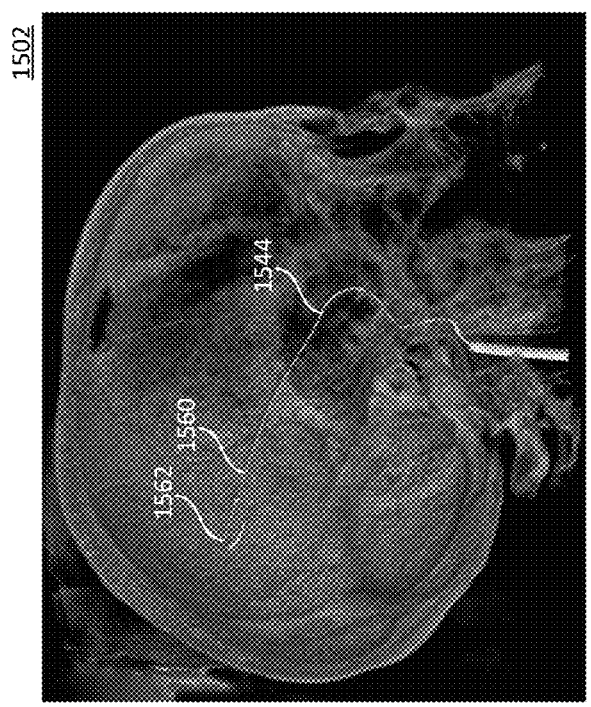
FIG. 15B is a lateral view of a 3D computer tomography scan a head of a subject, according to embodiments.
Figure 15A:
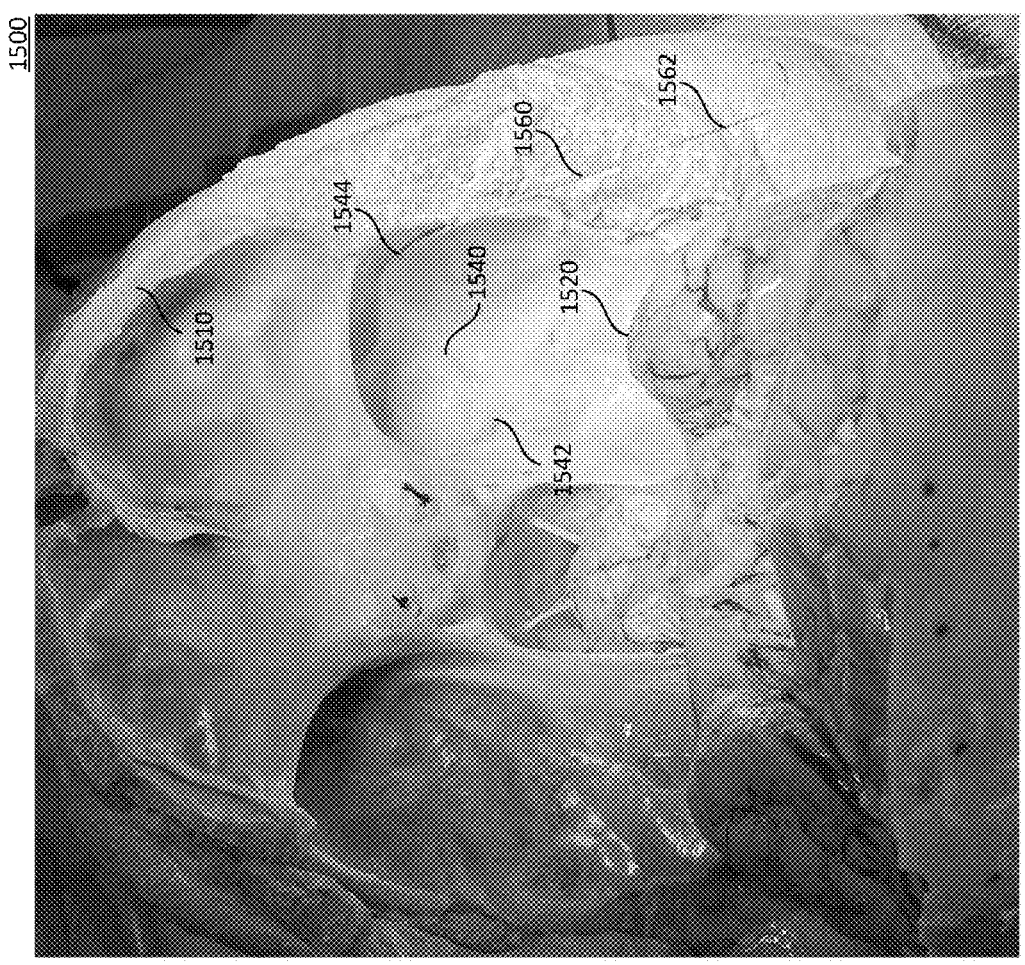
FIG. 15A is an image of a dissected cadaver head, according to embodiments.

Through modeling and testing, the location and orientation of a perforation in the MMA was found to correspond to a trajectory 1940, 1950 of a catheter and shaft advanced through an extravascular space. For example, FIG. 15A is a superior cross-sectional image of a dissected cadaver head where a catheter 1560 and shaft 1562 were advanced out of a perforation 1544 in the MMA 1540. As shown in FIG. 15A, the catheter 1560 and shaft 1562 advance linearly from the perforation 1544 such that a perforation location may be selected to aim the catheter 1560 and shaft 1562 towards areas of high probability SDH occurrence (e.g., towards the top of a patients head). FIG. 15B is a lateral view of the 3D rendering of a computer tomography scan of a subject having a catheter 1560 advanced along a linear trajectory from a perforation 1544 in an MMA.

Figure 19D:
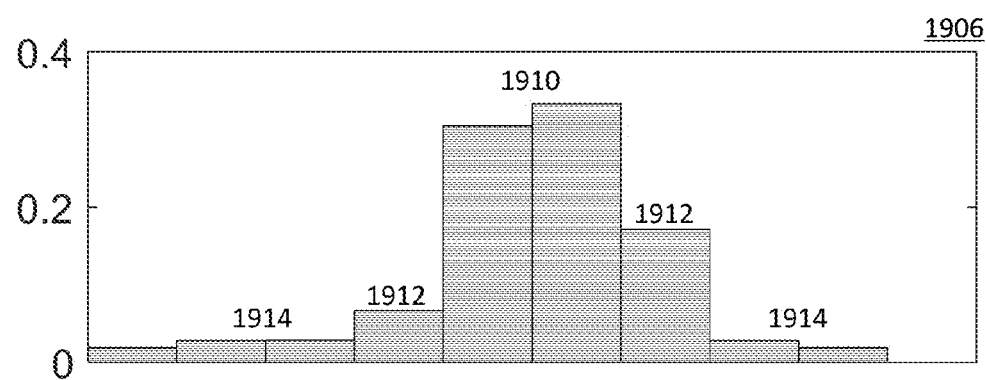
FIG. 19D is a plot of the probability of the set of arterial perforation trajectories intersecting the set of arterial perforation locations, according to embodiments.

FIG. 19B depicts a set of catheter and shaft trajectories from perforations in the posterior branches of the MMA 1932 including hematoma trajectories 1940 that facilitate access to high probability SDH areas (e.g., along dashed horizontal line) and non-hematoma trajectories 1950 that lead to low probability SDH areas. FIG. 19C is an overlay of a hematoma heat map 1904 and a set of arterial perforation locations 1920 (e.g., perforation map) corresponding to the hematoma trajectories 1940 in FIG. 19A. FIG. 19D is a plot of the probability of the set of arterial perforation trajectories intersecting different SDH areas. For example, high probability SDH areas 1910 comprise a significantly higher percentage of the set of arterial perforation trajectories 1920 than medium probability SDH areas 1912 and lower probability SHD areas 1914. Therefore, perforating the MMA within the set of arterial perforation locations 1920 leads to a high probability that a catheter and shaft will advance to a high probability SDH area of the subject. For example, of the 107 cases studied, the devices described herein were estimated to be able to reach an SDH for 105 cases by selecting an appropriate perforating point and advancing within the subdural space of up to about 5 cm. In the majority cases (92/105), a distal end of the catheter reached a region where SDH presence is highly probable (e.g., greater than about 80%).

Morphometric analysis of the MMA subjects that underwent MMAe found that the MMA angle at the *foramen spinous* is 100°±14°, and the MMA groove along the concave middle cranial fossa follows an angle of 160°±5.8°. A catheter having a distal outer diameter of 0.93 mm (0.036 inches) may be sufficient to navigate in a trunk of the MMA in at least 84% of subjects. The anterior division of the MMA was not deemed to provide a suitable trans-arterial pathway given the high prevalence of bony tunnels (up to 75%) which would preclude perforation, and due to the medially projected path along the sphenoid ridge that would direct the emerging shaft towards the brain.

A method of accessing an extravascular space may include navigating a catheter assembly to a predetermined location (e.g., perforation point), creating a transvascular passageway to an extravascular space from an intravascular compartment, advancing the catheter assembly to perform a procedure. For example, the catheter assembly may be advanced to penetrate the membranes and septations of a subdural hematoma to then apply suction to drain the subdural hematoma. The methods using the systems and devices described herein may reduce blood extravasation while the passageway is patent, enable navigation within the intracranial compartment without brain perforation or damage, allow drainage of subdural collections, and facilitate arteriotomy (e.g., perforation of the arterial wall and/or dura) closure and artery occlusion upon the removal of the catheter system.

Figure 10:
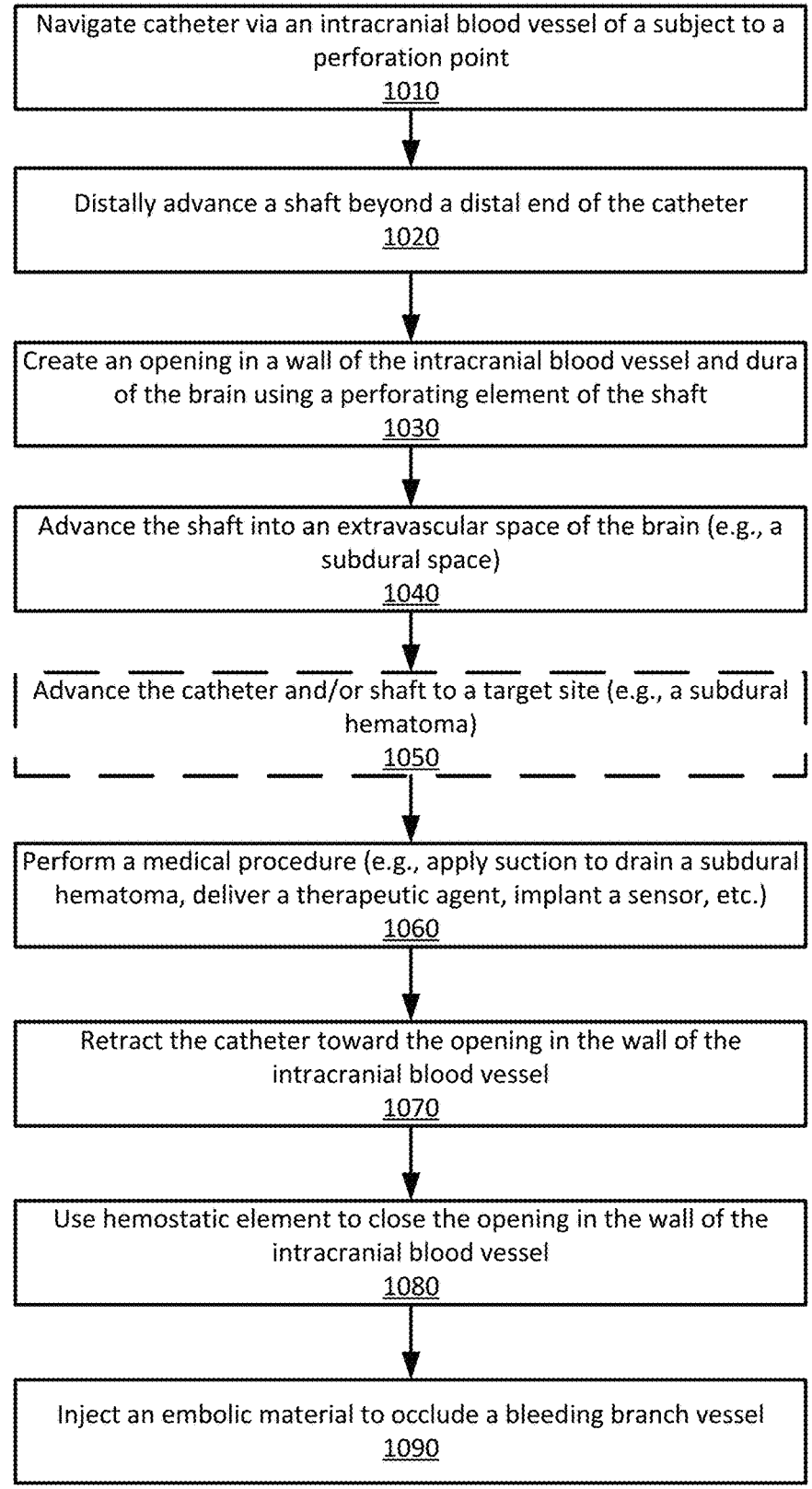
FIG. 10 is a flow diagram of a method of accessing an extravascular space, according to embodiments.

FIG. 10 is a flow chart of a method 100 for performing a medical procedure (e.g., draining a subdural hematoma, delivering a therapeutic agent, implanting a device) within an extravascular space (e.g., intracranial space, extravascular spaces along a spinal cord of a subject). The method 1000 may include navigating a catheter via an intracranial blood vessel of a subject to a perforation point, at 1010. For example, a distal end of a catheter disposed within an intracranial vessel of a subject may be positioned near a target location.

At 1020, a shaft may be advanced distally beyond a distal end of the catheter or flush to the end of the catheter and the latter pulled back unsheathing the shaft. For example, a shaft may be advanced through a lumen of the catheter such that a curved section of the shaft curves in a direction along a curve of the vessel. The curved section may be constrained within the lumen of the catheter within the vessel. The curved section of the shaft may be extended out of the distal end of the catheter such that the curved section curves toward a wall of the vessel and positions a RF element disposed at a distal end of the shaft against the wall of the vessel.

At 1030, an opening in a wall of the intracranial blood vessel and dura may be created using a perforating element of the shaft. For example, a RF element may be activated to deliver RF energy to the wall of the vessel to create an opening through the wall of the vessel and dura of the subject and into an extravascular intracranial space. Optionally, fluid (e.g., contrast fluid, saline) may be injected adjacent the opening to confirm the opening, cool tissue, and/or increase lubricity and width of the opening.

At 1040, a shaft may be advanced into an extravascular space (e.g., extravascular intracranial space, extravascular spinal intradural space). For example, the shaft may be advanced into a subdural space. For example, the distal end of the shaft may be advanced into the extravascular intracranial space until the curved section transitions to an unconstrained configuration within the extravascular intracranial space. In some embodiments, the catheter may be advanced over the shaft and into the extravascular intracranial space.

At 1050, one or more of the catheter and shaft may be optionally advanced to a target site. For example, the catheter and/or shaft may be advanced to a subdural hematoma.

At 1060, a medical procedure may be performed. For example, suction may be applied to drain a subdural hematoma, deliver a therapeutic agent, implant a sensor or electrode, delivery a biopsy needle, and the like. In some embodiments, the distal end of the shaft may be advanced into a subdural hematoma. The catheter may be advanced over at least a portion of the shaft and into the subdural hematoma. Suction may be applied to the lumen of the catheter to remove fluid from the subdural hematoma after the catheter is positioned within the subdural hematoma.

At 1070, the catheter may be retracted toward the opening in the wall of the intracranial blood vessel. For example, the catheter may be retracted back toward the opening created in the wall of the artery (e.g., MMA).

At 1080, a hemostatic element may be used to close the opening in the wall of the intracranial blood vessel. For example, a hemostatic element or RF device may be delivered via the lumen of the catheter to close the opening.

At 1090, an embolic material may be injected to occlude a bleeding branch vessel. In some embodiments, embolic material may be injected prior to creating an opening in the wall of the intracranial blood vessel and dura of the brain (e.g., before step 1030).

The steps in method 1000 are described and depicted in more detail with respect to FIGS. 11A-11L, 12A-12B, 13A-13J, 14A-14F, 15A-15B, 16, and 17A-17D. The catheter assembly described in these figures may include components that are structurally and/or functionally similar to the catheter assembly components described with respect to FIGS. 5, 6, 7A-7D, 8A-8C, and 9.

FIGS. 11A-11L are X-ray images and photographs of a method of accessing an extravascular intracranial space using the MMA 1120 corresponding to the steps of method 1000. The anatomy depicted in FIGS. 11A-11L includes the MMA 1120 (e.g., middle cranial fossa), foramen spinous 1122, frontal branch of the MMA 1124, parietal branch of the MMA 1126, bone 1150 (e.g., skull), and subdural space 1160. As shown in image 1100 of FIG. 11A, a distal end of a catheter may be disposed within an intracranial vessel of a subject near a target location. In particular, a catheter may be navigated via the MMA 1120 distal to the foramen spinous (having a sharp bend). The catheter may be imaged via first catheter fiducial 1130 disposed at a distal end of the catheter and a second catheter fiducial 1132 disposed proximal to the first catheter fiducial 1130. The second catheter fiducial 1132 is disposed just proximal to the foramen spinous 1122 in FIG. 11A.

A shaft may be disposed within a lumen of the catheter. The shaft may include a perforating element (e.g., electrode, perforating tip) 1142, a first discontinuity between the perforating element and a curved section (e.g., distal tip portion) of the shaft, a second discontinuity disposed proximal of the curved section, a first shaft fiducial 1144, and a second shaft fiducial 1146. The second discontinuity may located at or proximal to the first shaft fiducial 1144. The second discontinuity may include an offset (e.g., partial helix, twist) configured to orient the curved section to follow a curve of the blood vessel (which follows the curve of the skull base and cranial vault with a medial concavity) as the shaft is advanced within the lumen of the catheter.

Figure 11A:
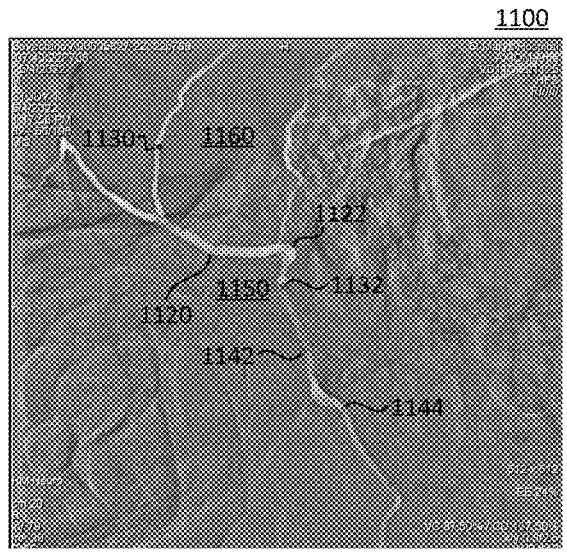
Figure 11B:
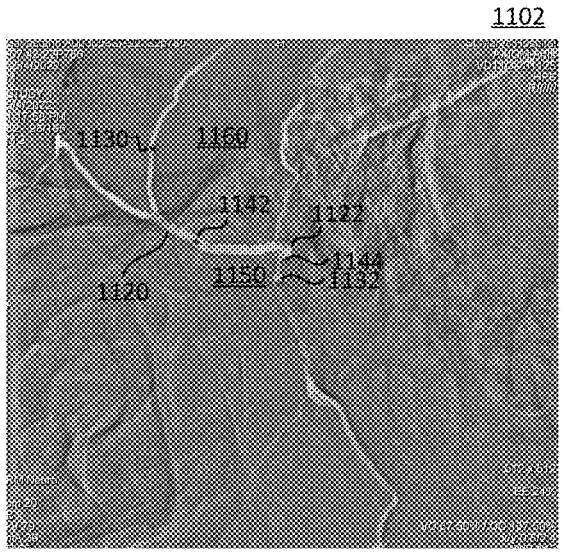

In FIG. 11B, the perforating element 1142 is advanced past the sharp bend of the foramen spinous and into the middle cranial fossa where the first shaft fiducial 1144 is not advanced past the foramen spinous 1122. In some embodiments, the first shaft fiducial 1144 does not self-orient (e.g., rotate) the distal end of the shaft until the first shaft fiducial 1144 is advanced past the foramen spinous 1122. As shown in the image 1102 of FIG. 11B, the perforating element 1142 has a slight bias towards the bone 1150 such that the perforating element 1142 faces more towards the bone 1150 than the subdural space 1160. If RF energy were applied to the electrode positioned as in FIG. 11B, an opening in the MMA 1120 would form facing the bone 1150 rather than the subdural space 1160. Therefore, perforating the MMA at this location would not consistently form a clinically relevant passageway to the intracranial extravascular space.

Figure 11C:
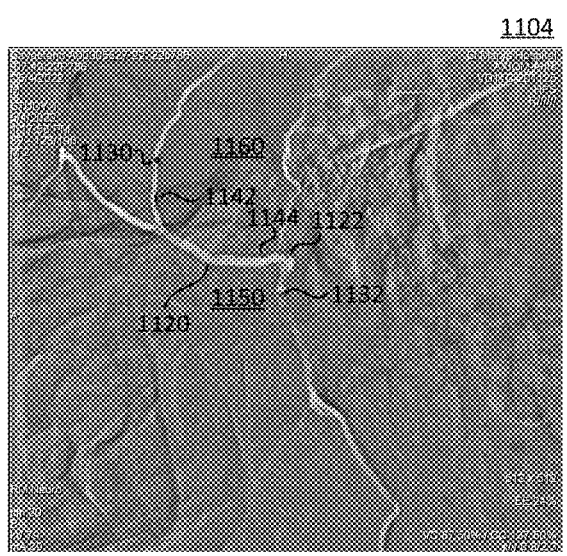

Further advancement of the shaft in FIG. 11C advances the perforating element 1142 closer to the first catheter fiducial 1130 and the first shaft fiducial 1144 distal to the foramen spinous 1122. In this configuration, the potential energy stored in the second discontinuity is released to rotate a distal end of the shaft and electrode 1142 to orient the shaft towards a wall of the MMA facing the subdural space 1160. As shown in the image 1104 of FIG. 11C, the electrode 1142 is biased towards the subdural space 1160 such that the electrode 1142 naturally contacts a wall of the MMA that faces the dura and subdural space 1160. In this manner, visualization of the location of the first shaft fiducial 1144 relative to the foramen spinous 1122 may be used to determine that the shaft has rotated properly into a desired orientation (e.g., perforating element curves toward a wall of the MMA 1120 facing the subdural space 1160).

Figure 11D:
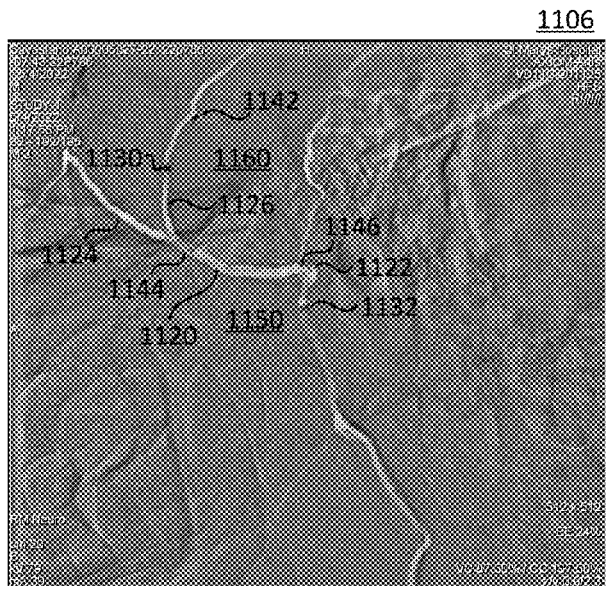
Figure 11E:
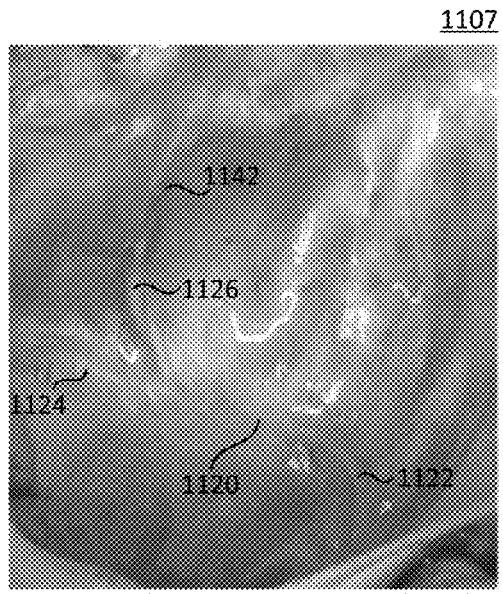

As shown in the image 1106 of FIG. 11D, a distal tip of the perforation element 1142 is advanced past the first catheter fiducial 1130 where the second shaft fiducial 1146 has advanced past the foramen spinous 1122. Accordingly, the shaft is advanced past a distal end of the catheter. Again, due to the rotation provided by the second discontinuity, the shaft in image 1106 has self-oriented to curve toward the wall of the MMA 1120 and the subdural space 1160 (e.g., dura). Other than longitudinal advancement of the shaft, the operator need not rotate the shaft to properly orient the perforating element 1142 to form a transvascular passageway as the rotation is induced by the tendency of the discontinuity (e.g., offset, hyperelastic material in a core of the shaft) to accommodate to (e.g., follow) the geometry that most closely resembles its resting state. In some embodiments, the second shaft fiducial 1146 located just distal to the foramen spinous 1122 may indicate to the operator that the perforating element 1142 is disposed at a predetermined perforating location. FIG. 11E is an image 1107 of brain tissue having a catheter assembly disposed therein corresponding to the image 1106 of FIG. 11D. The catheter and electrode 1142 of the shaft are disposed within a parietal branch 1126 of the MMA 1120.

Figure 11F:
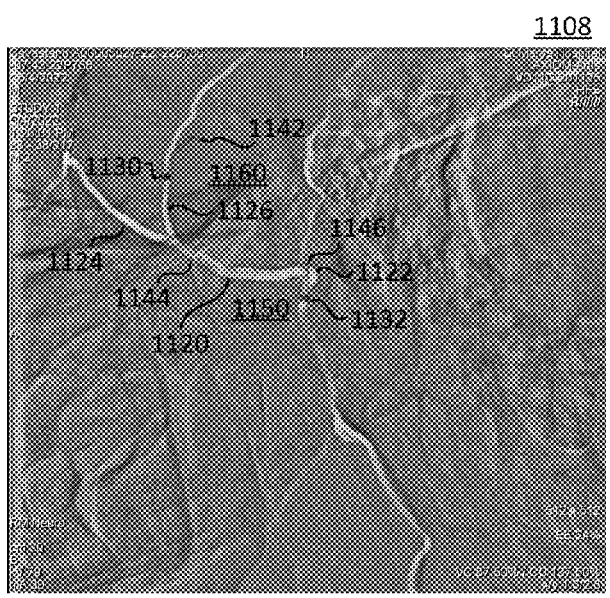

FIG. 11F is an image 1108 showing the location of the perforating element 1142 during RF tissue ablation where the perforating element 1142 has created an opening through the MMA 1120 and into the subdural space 1160. The operator need not apply a force (e.g., push) to the shaft in order to create the opening. Instead, the RF energy applied to tissue by the perforating element 1142 and the predetermined bias of a distal tip portion (e.g., curved section) naturally pushes a tip of the perforating element 1142 into the subdural space 1160. As energy is applied and the opening is formed, a slit may be created as the perforating element 1142 biases into its unconstrained curved shape.

Figure 11G:
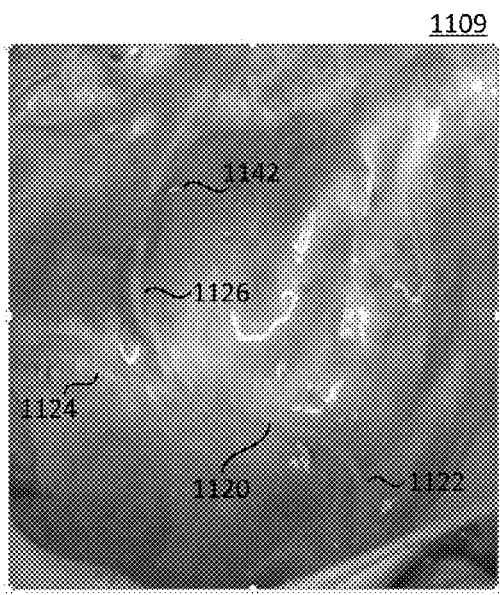

FIG. 11G is an image 1109 of the middle cranial fossa (right side) corresponding to the image 1108 of FIG. 11F where the perforating element 1142 has formed an opening through the MMA 1120 and dura. A tip of perforating element 1142 is exposed in FIG. 11G. The curved section of the shaft is further configured to reduce injury to brain tissue as it naturally curves back toward the dura and away from the brain.

FIG. 11H is an image 1110 showing the perforating element 1142 disposed within the subdural space as tissue ablation is completed. In some embodiments, the distal tip portion of the shaft may form a J-shape (e.g., knuckle shape) when unconstrained. Due to the curved shape of the shaft and the curve of the MMA along the concavity of the lateral middle cranial fossa, the slit can only occur towards the subdural space (self-directional). The configuration (e.g., length) of the perforating element 1142 may provide depth-controlled perforation such that the slit is not deeper than the dura (e.g., does not contact brain tissue). Therefore, the curved section of the shaft may ensure that the perforating element 1142 does not contact and injure brain tissue.

FIG. 11I is an image 1111 of the middle cranial fossa (right side) corresponding to image 1110 of FIG. 11H where a distal tip portion (e.g., curved section) 1140 and perforating element 1142 are advanced out of the opening 1127 and into a subdural space. As shown in FIG. 11I, a first discontinuity (e.g., bend) between the perforating element 1142 and the distal tip portion 1140 may provide an inward tilt of the perforating element 1142 to improve point contact between the perforating element 1140 and the vessel wall to concentrate RF energy to vaporize tissue with minimal heat generation and tissue shrinkage. In some embodiments, the opening has a length that is equal or substantially equal to a length of the perforating element 1142.

FIG. 11J is an image 1112 showing the shaft advanced from the opening between the MMA 1120 and subdural space 1160 along a predetermined trajectory (e.g., linear trajectory within the 2D plane of image 1112). The first shaft fiducial 1144 may be advanced to be aligned with the first catheter fiducial 1130. In some embodiments, the first shaft fiducial 1144 may have an outer diameter substantially equal to an inner diameter of the catheter at the first catheter fiducial 1130 to prevent ovalization of the catheter as described herein. Accordingly, the catheter and shaft may be advanced out of the slit opening 1127 together without an edge of the catheter catching against tissue.

Figure 11K:
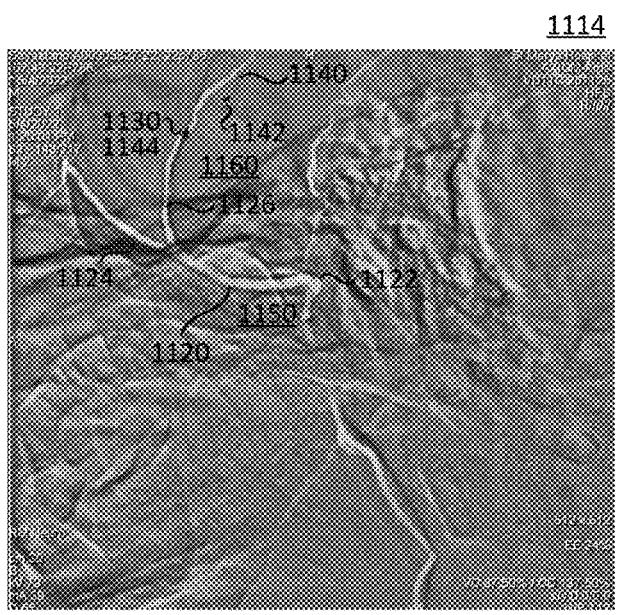

FIG. 11K is an image 1114 showing the first catheter fiducial 1130, distal tip portion 1140, and perforating element 1142 advanced into the subdural space from the opening 1127. The distal tip portion 1140 is fully unconstrained and forms an atraumatic shape (e.g., J-shape, knuckle) that may prevent tissue damage as the shaft is advanced through the extravascular space.

Figure 11L:
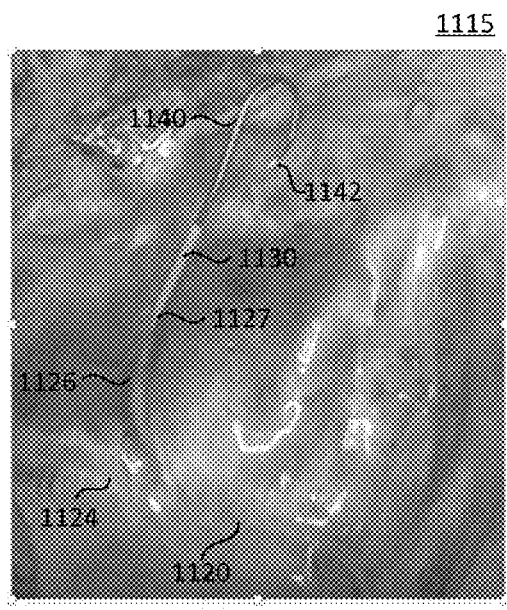

FIG. 11L is an image 1115 of the middle cranial fossa (right side) corresponding to image 1114 of FIG. 11K showing the catheter and shaft advanced out of the opening 1127 and into the subdural space. The catheter and shaft follow a linear trajectory from the opening 1127.

Figure 13D:
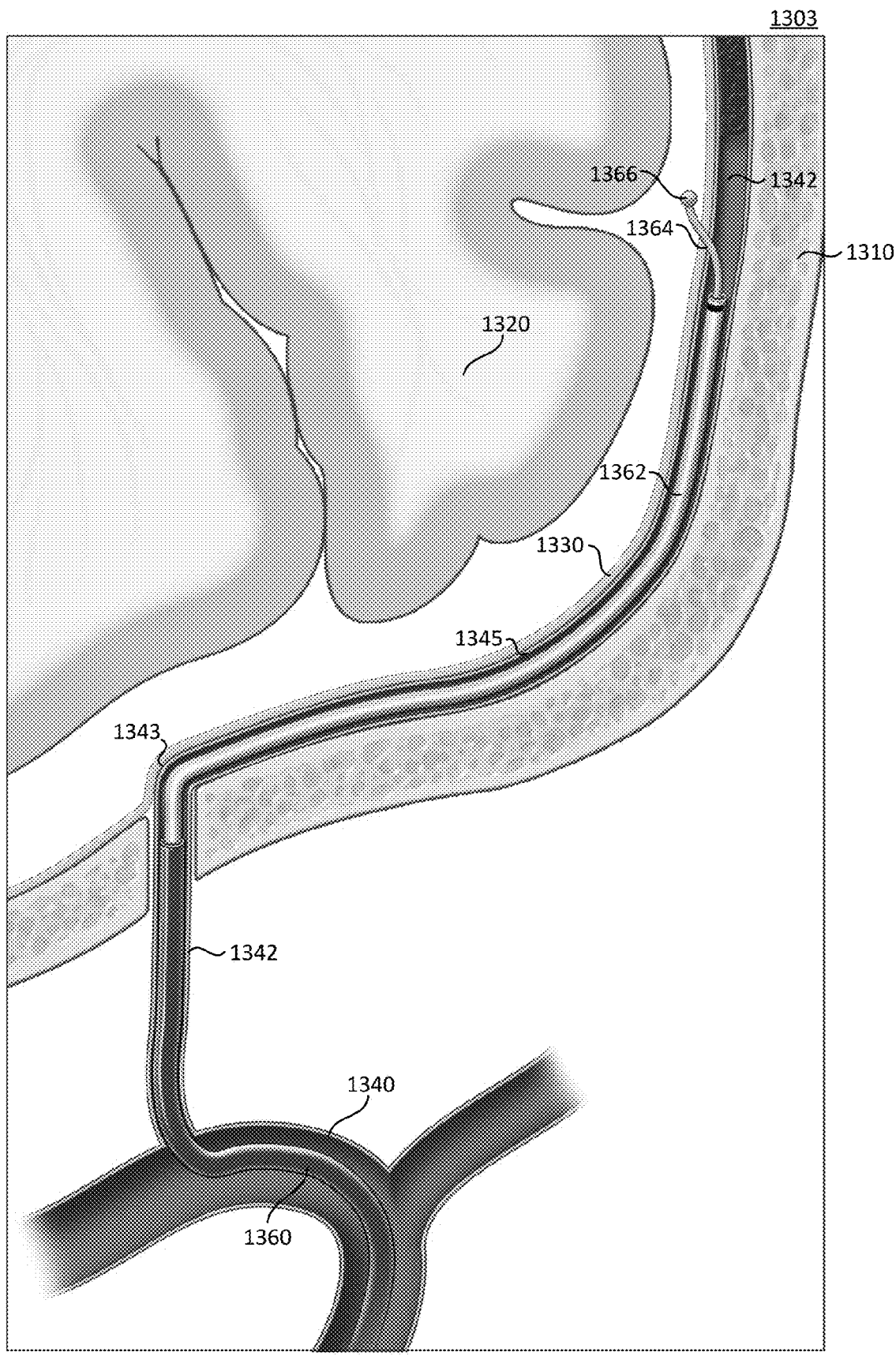
Figure 13F:
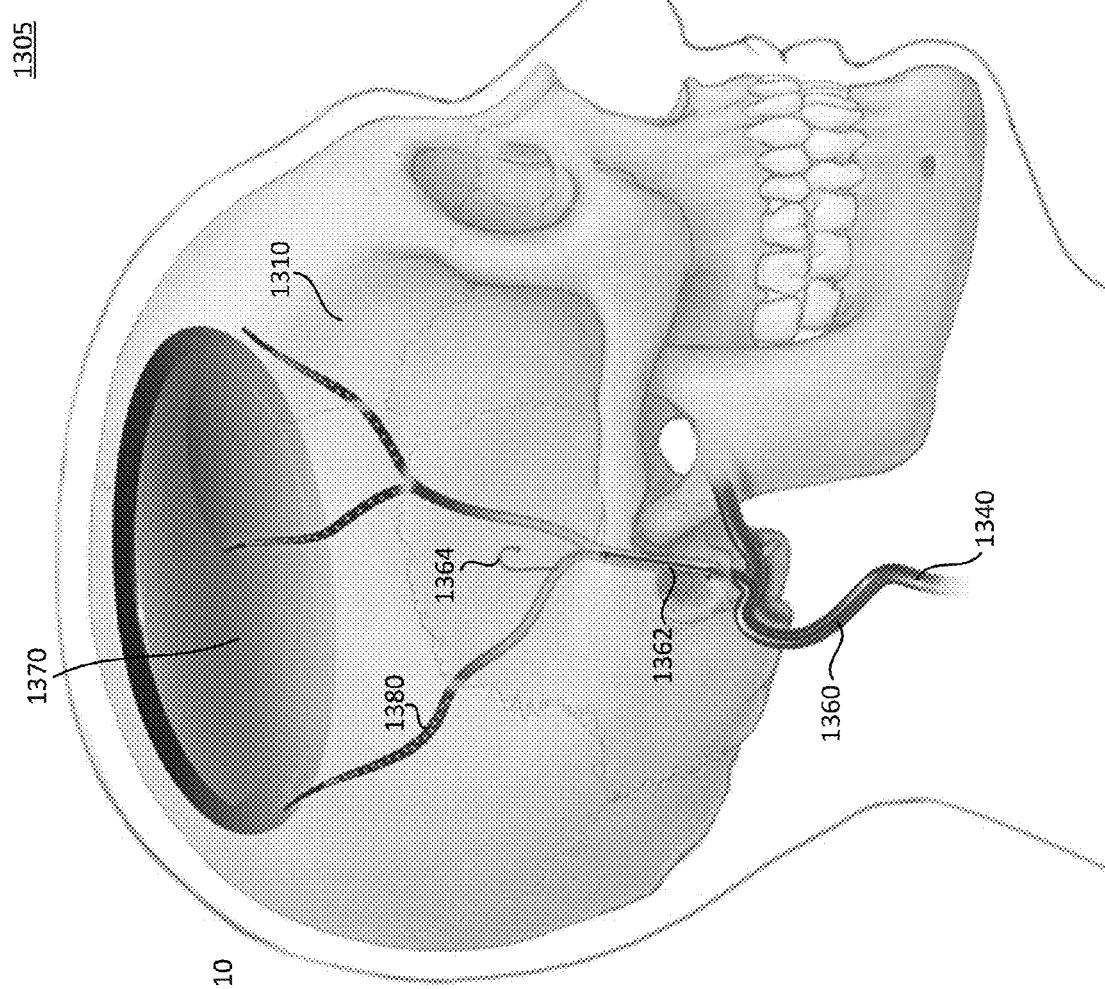
Figure 13E:
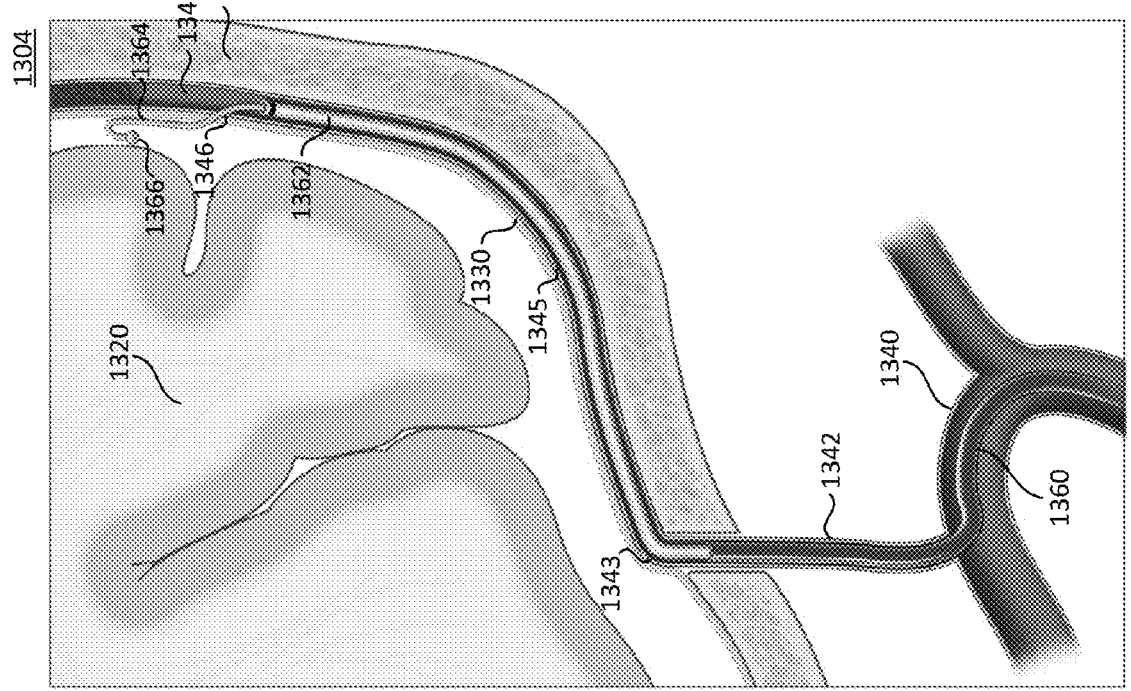
Figures 13G, 13H:
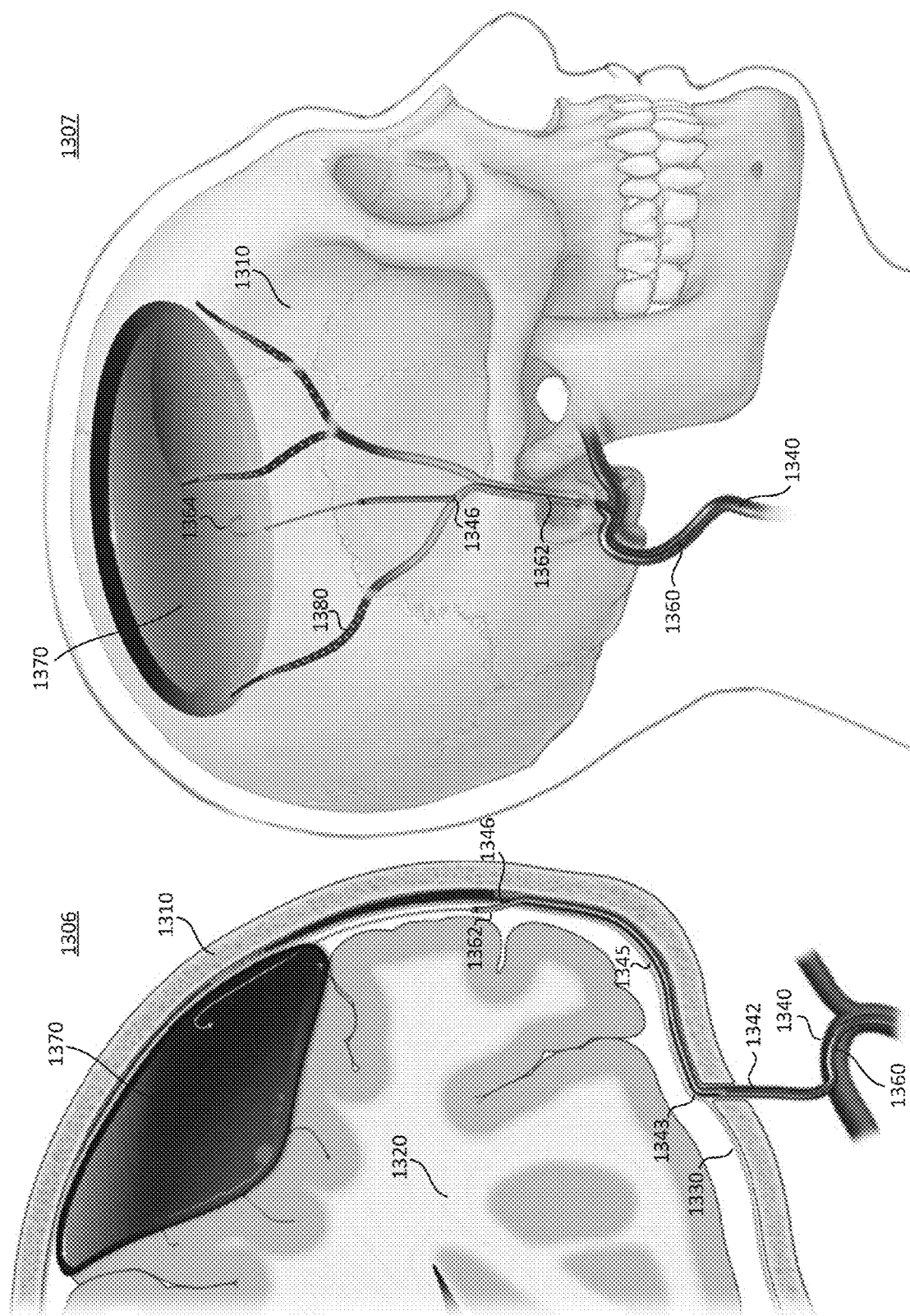

FIGS. 13A-13J are schematic cross-sectional views of a head of subject corresponding to the steps of method 1000 and devices described herein. FIGS. 13A, 13B, 13D, 13E, 13G, and 13I are coronal cross-sectional views of a head of a subject. FIG. 13C is a schematic axial cross-sectional view of a head of a subject. FIGS. 13F, 13H, and 13J are lateral views of a head of a subject.

FIG. 13A is a coronal cross-sectional view 1300 of a head including bone (e.g., skull) 1310, brain 1320, dura 1330, internal maxillary artery 1340, middle meningeal artery (MMA) 1342, and intradural space 1350. FIG. 13B is a detailed cross-sectional view 1301 of FIG. 13A. The MMA 1342 may include the foramen spinous 1343 and middle cranial fossa 1345. As shown in FIG. 13A, a delivery catheter (e.g., sheath) 1360 may be disposed within the internal maxillary artery and a proximal portion of the MMA. A catheter 1362 (e.g., suction catheter, occlusion catheter) may be slidably disposed within a lumen of the delivery catheter 1360. The catheter 1362 may be advanced from a distal end of the delivery catheter 1360 and past the foramen spinous 1343 and into the middle cranial fossa 1345. As shown in FIG. 13B, a shaft 1364 may be slidably disposed within a lumen of the catheter 1362. The shaft 1364 may be advanced from a distal end of the catheter 1362. The shaft 1364 may include a perforating element 1366 and a curved section configured to self-orient after being advanced past the foramen spinous 1343 such that the perforating element 1366 biases toward a wall of the MMA 1342 facing the dura 1330 and subdural space 1350.

FIG. 13C is a schematic axial diagram 1302 of the head including the bone 1310, brain 1320, dura 1330, and MMA 1342. In order to from a transvascular passageway from a blood vessel to the extravascular space, an opening must be formed between the brain and MMA 1342 through the dura 1330. For example, the perforating element 1366 may be directed along an arc (e.g., less than 180°) as shown in FIG. 13C. However, an opening formed in the MMA 1342 facing the bone 1310 will not provide access to the subdural space, let alone a hematoma. Thus, proper positioning and orientation of the perforating element 1366 ensures successful access to the extravascular space.

Energy may be applied to the perforating element 1366 only to form the opening to prevent ablation of brain tissue 1320. The perforating element 1366 may have an atraumatic shape (e.g., blunt, rounded distal end) such that contact between the perforating element 1366 and the brain will not damage brain tissue.

Figures 12A, 12B:
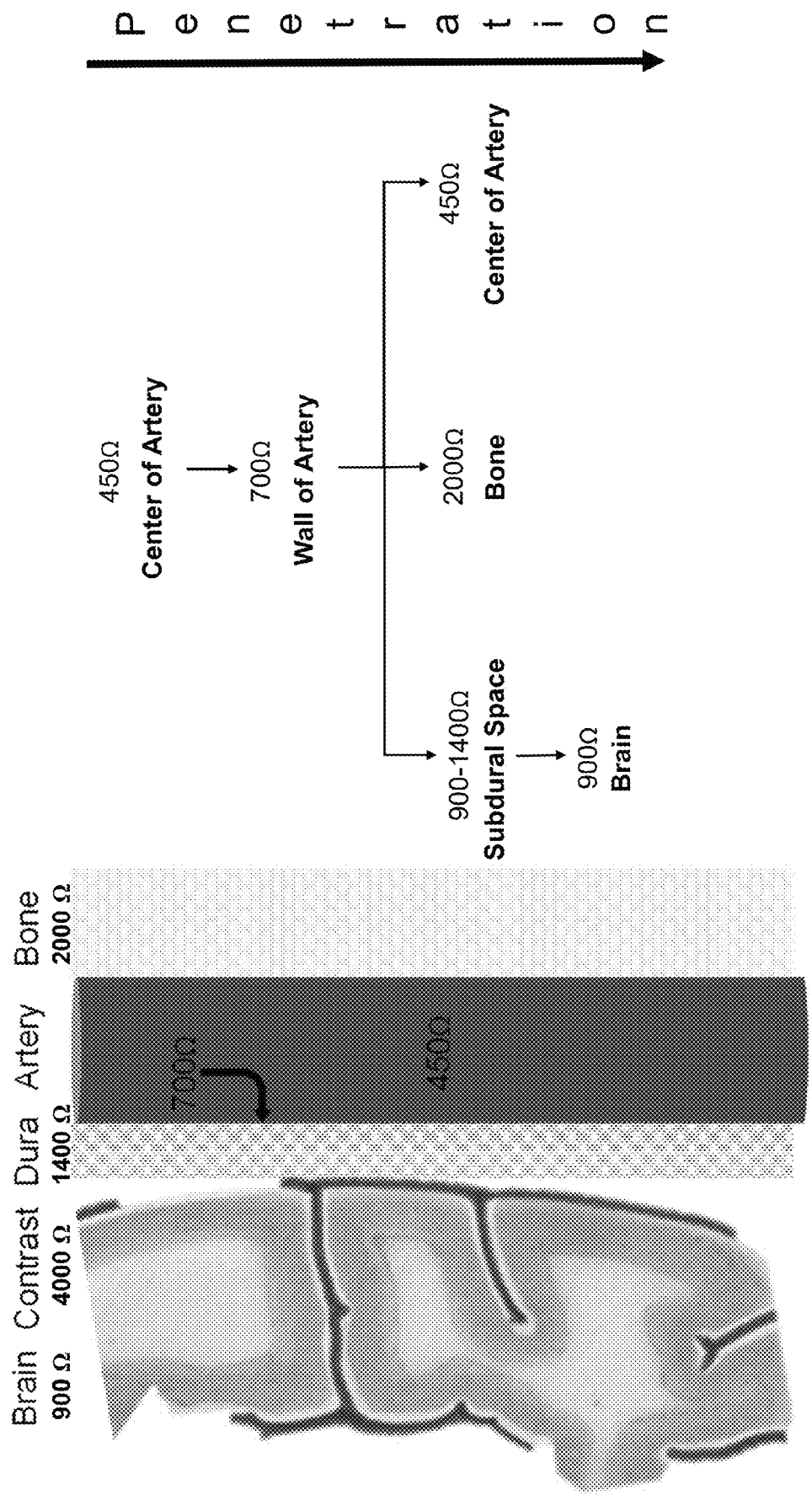
FIGS. 12A and 12B are schematic diagrams of tissue impedance, according to embodiments.

FIGS. 12A and 12B are schematic diagrams of tissue impedance. For example, the impedance differences between the brain, subdural space, dura, contrast fluid, blood vessel, and bone are such that impedance measurement may be used to determine a location of a device (e.g., shaft, catheter) within the subject. For example, an impedance measurement of about 700Ω may correspond to a perforating element 1366 self-oriented against a wall of the blood vessel while an impedance measurement of about 450Ω may indicate that the shaft has yet to self-orient and has poor point contact against the vessel wall. As shown in FIG. 12B, an opening created through a wall of the artery and a subdural space may correspond to an increase in impedance from about 700Ω to between about 900Ω and about 1400Ω. Energy delivery may be reduced and/or stopped when impedance corresponding to the subdural space is measured. In some embodiments, a signal generator may be configured to stop energy delivery when impedance measurements fall outside this range. For example, an opening created through a wall of the artery and into bone may correspond to an increase in impedance from about 700Ω to about 2000Ω. Energy delivery may be stopped when an impedance of about 2000Ω is measured, and a notification (e.g., audible warning, visual indicator) may be output by an input/output device to an operator. In some embodiments, impedance may be measured throughout a procedure. For example, after aspiration of a SDH, the catheter and shaft may be withdrawn back into a blood vessel, which may be confirmed by one or more of fluoroscopic visualization and impedance measurement (e.g., about 400Ω). In some embodiments, impedance or/and other dielectric properties of tissue may be measured and used to control delivery of RF energy before, during and after one or more of creation of a transvascular passageway, extravascular navigation, and arterial occlusion.

FIG. 13D is a coronal cross-sectional view 1303 of a head where the perforating element 1366 has formed an opening (e.g., slit) through a wall of the MMA 1342 and dura 1330 in a push-less manner such that the perforating element 1366 and a distal tip portion of the shaft 1364 are disposed within a subdural space 1350. FIG. 13E is a coronal cross-sectional view 1304 of a head where the shaft 1364 is further advanced out of the opening 1346 into the subdural space 1350 such that a distal tip portion of the shaft 1364 transitions from a radially constrained configuration (e.g., following the shape of the MMA 1342) to a curved configuration (e.g., forming a J-shape or knuckle shape). FIG. 13F is a lateral view 1305 of a head where the shaft 1364 extends into the subdural space from the MMA 1342. The trajectory of the shaft 1364 from the opening in the artery intersects the SDH 1370. For an SDH 1370 having a large volume, the shaft 1364 may directly enter the SDH 1370 after emerging from an arterial lumen and dura. The curved configuration of the shaft 1364 may be parallel to a surface of the brain (as opposed to towards the brain) during advancement in the subdural space. In some embodiments, saline irrigation can be infused in the subdural space to facilitate one or more of advancement of the catheter assembly (e.g., to increase lubricity of the surfaces and create a volume of the subdural space) and direct visualization using an optical sensor (e.g., camera). FIG. 13F further illustrates embolic material 1380 (e.g., 150 μm to 250 μm PVA particles) adjacent to the SDH 1370 previously delivered to the arterial vessels.

FIG. 13G is a coronal cross-sectional view 1306 and FIG. 13H is a lateral view 1307 of a head where the shaft 1364 and catheter 1362 are advanced into the subdural space towards the SDH. In particular, the shaft 1364 has advanced atraumatically through the subdural space into the SDH 1370 and the shaft 1364 has traversed a capsule of the SDH 1370.

Figure 14B:
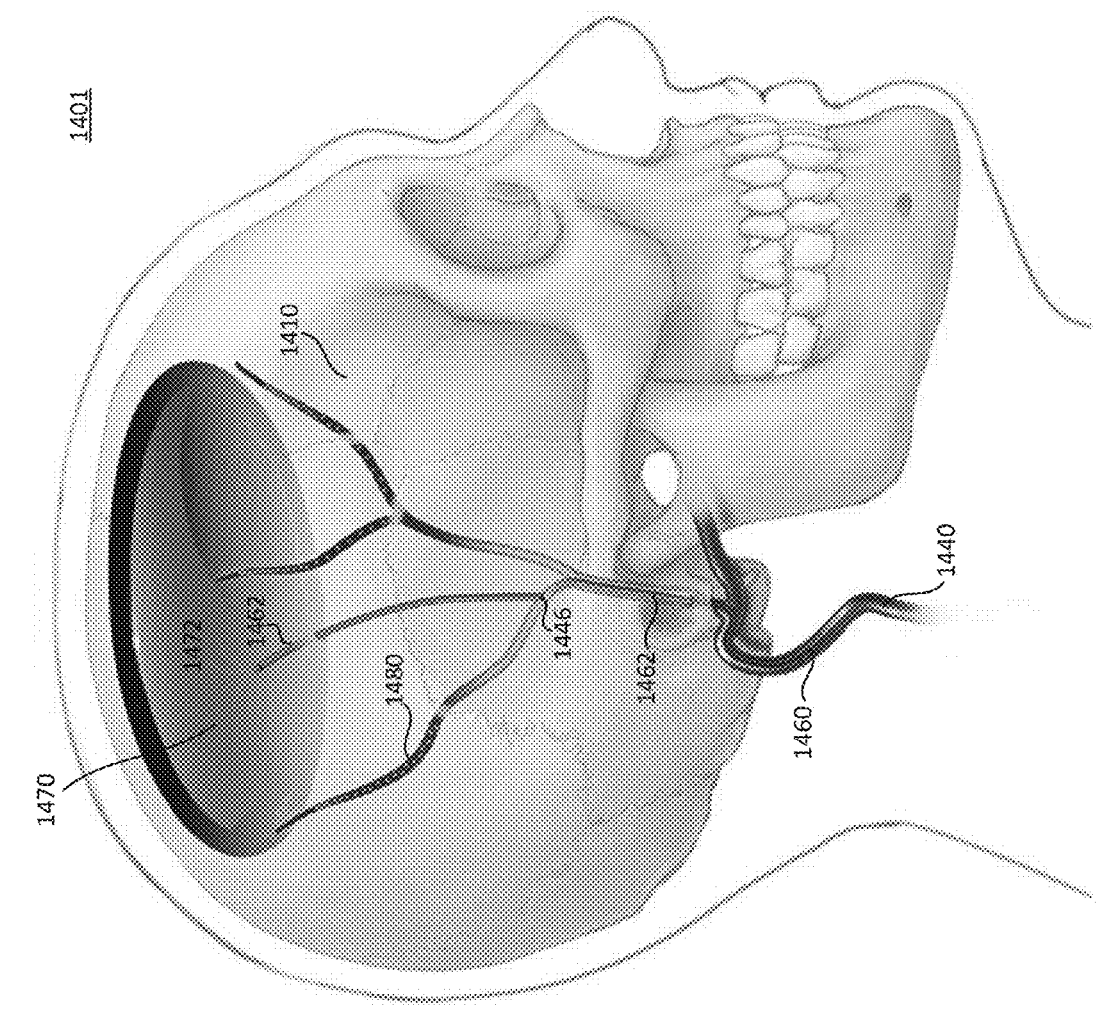
FIGS. 14B, 14D, and 14F are lateral views of a head of a subject, according to embodiments.
Figure 14A:
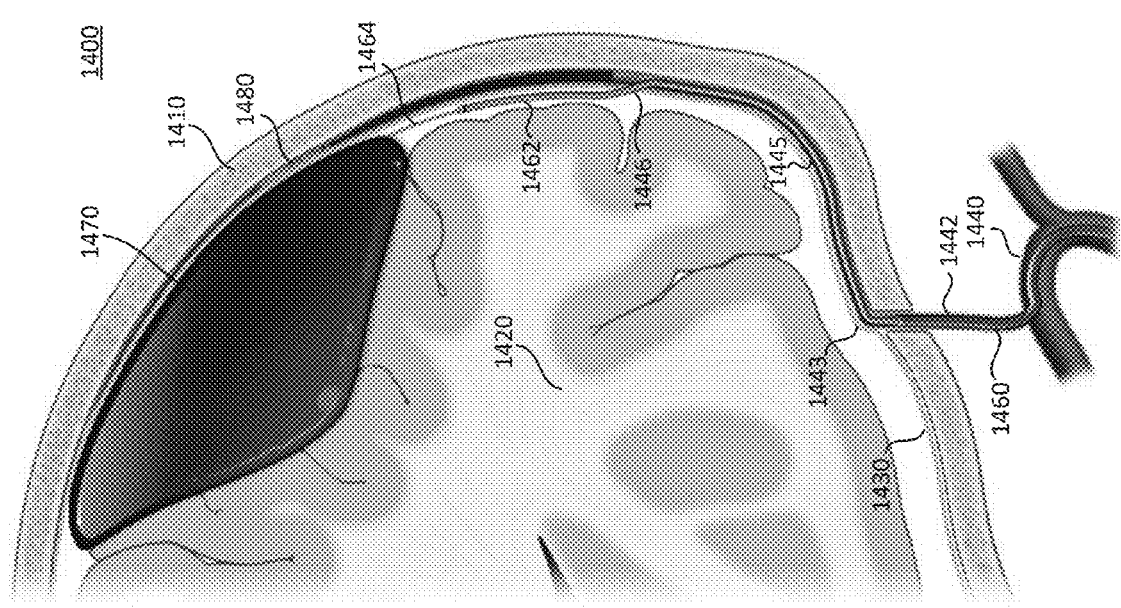
FIGS. 14A, 14C, and 14E are coronal cross-sectional views of a head of a subject, according to embodiments.
Figure 14C:
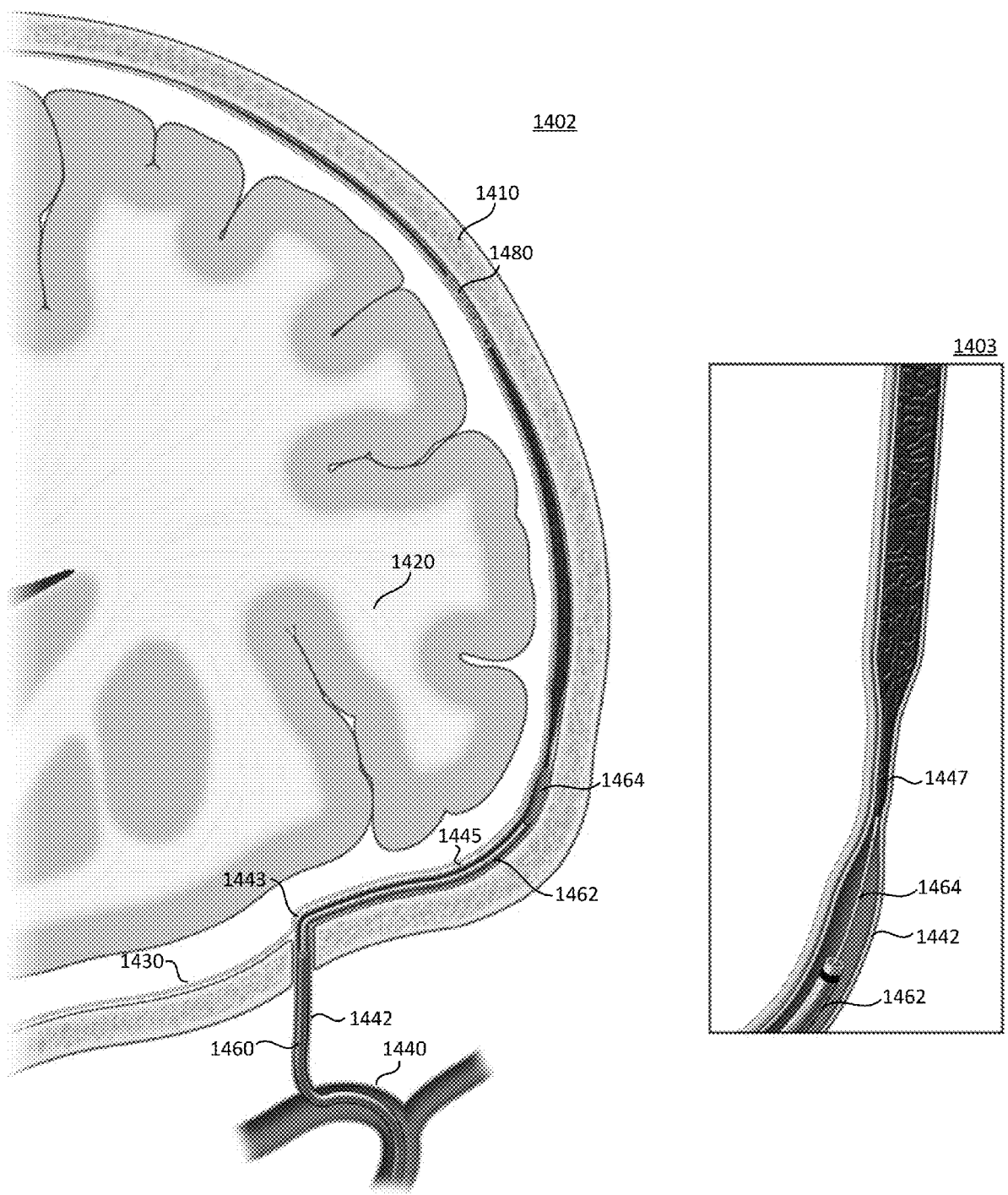
Figure 14D:
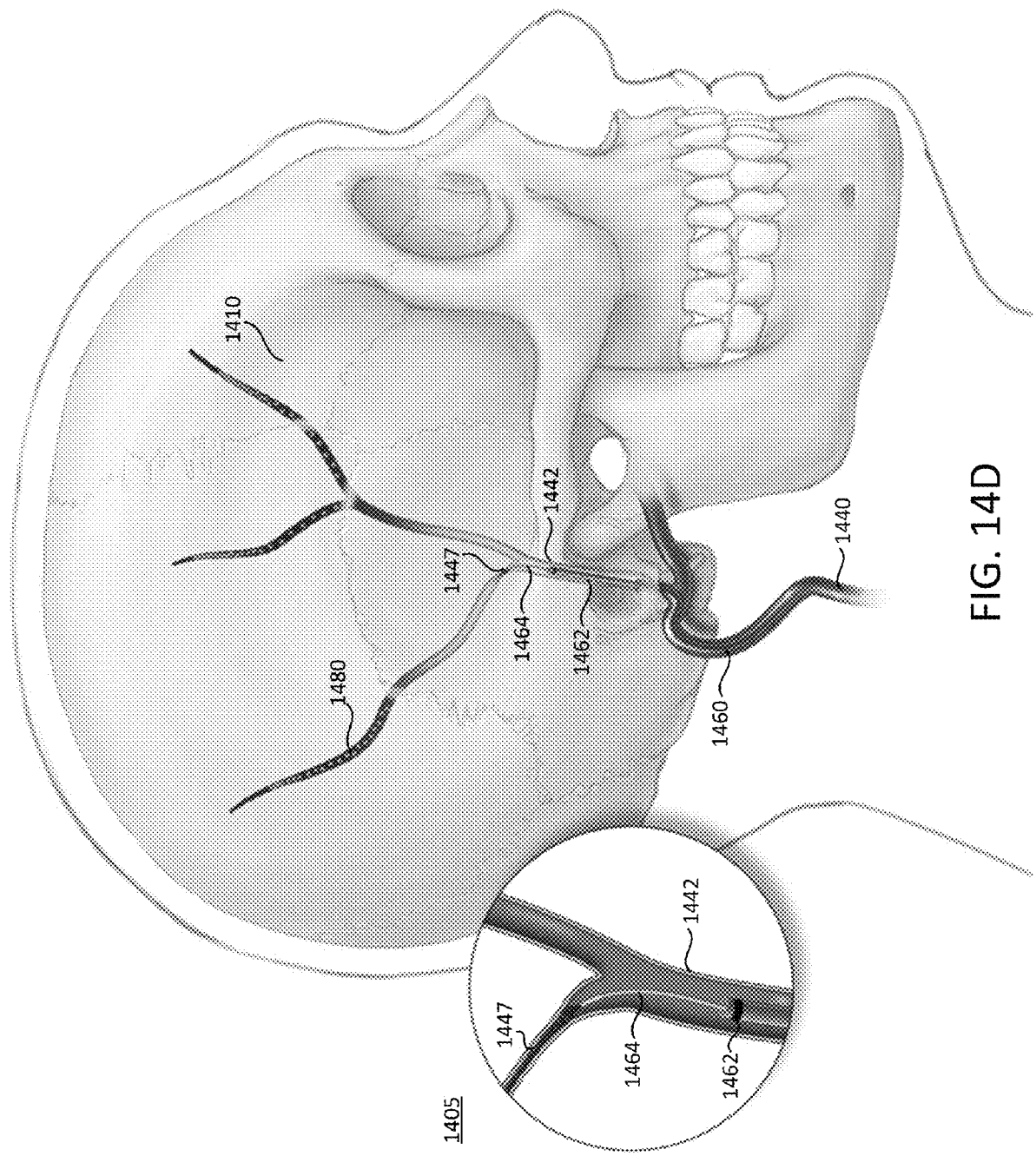
Figure 14E:
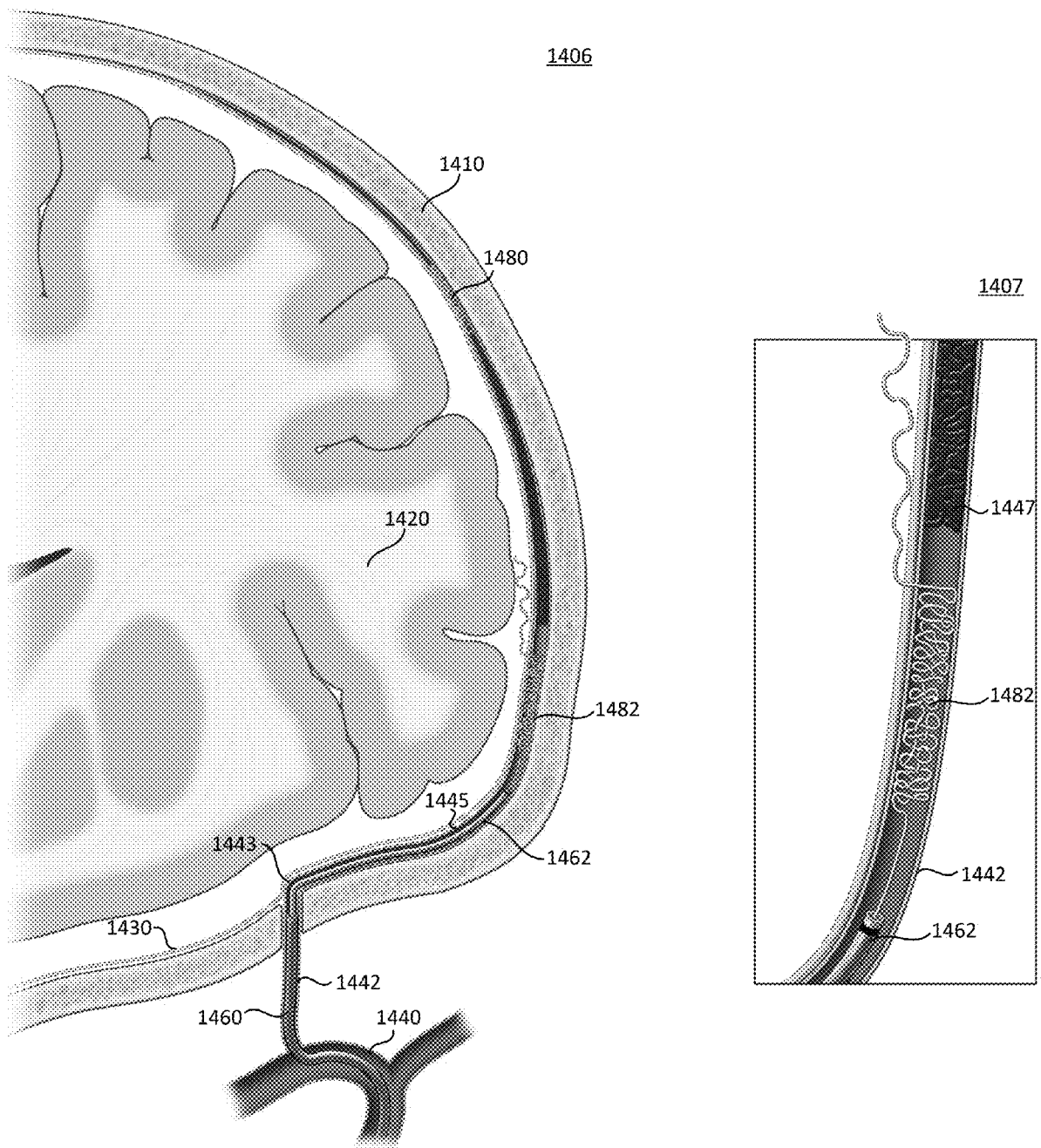
Figure 14F:
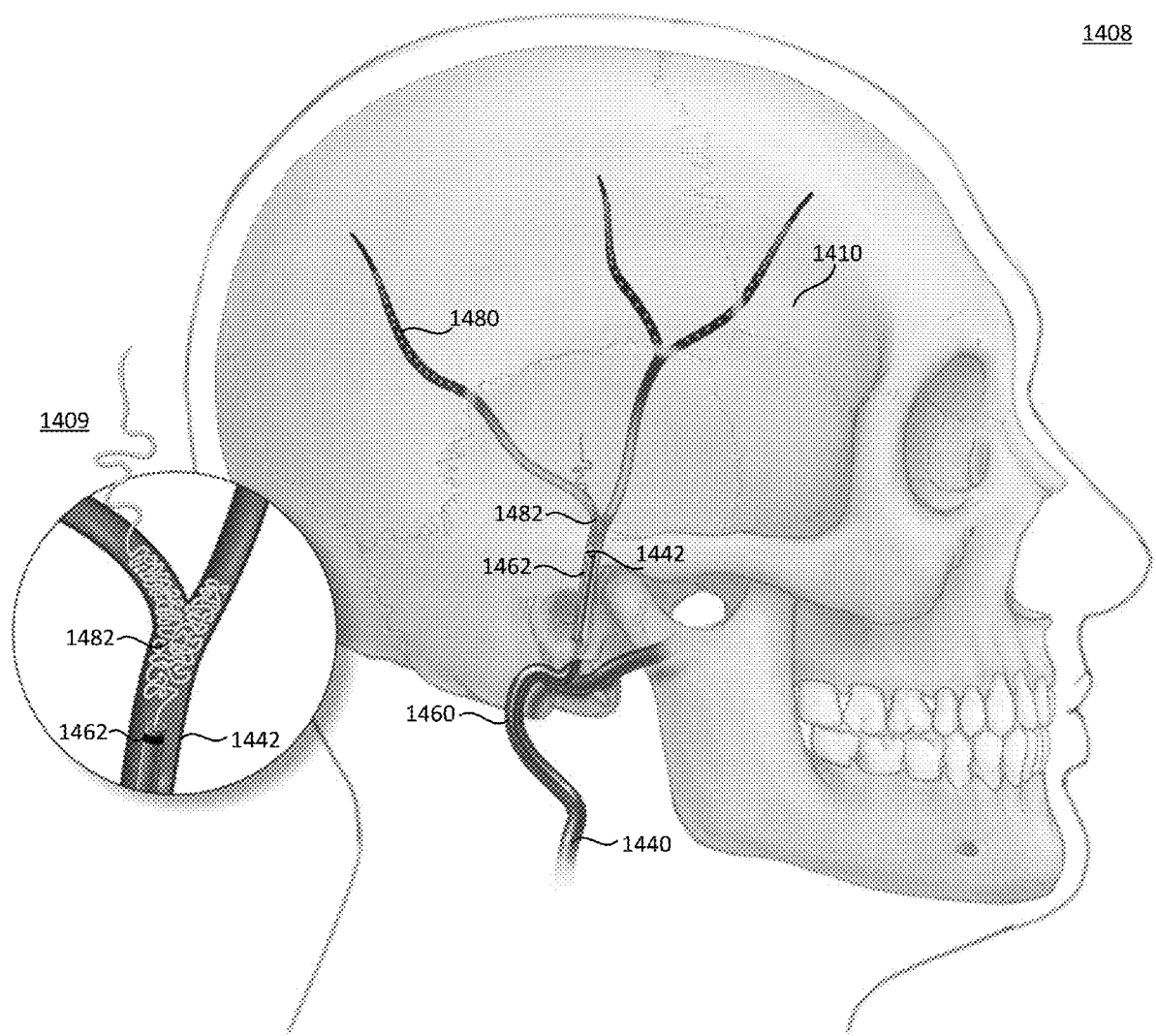

FIG. 13I is a coronal cross-sectional view 1308 and FIG. 13H is a lateral view 1309 of a head where the catheter 1362 has been advanced into the SDH 1370 and the shaft 1364 has been withdrawn through a lumen of the catheter 1362. FIGS. 13I and 13H depict suction (e.g., aspiration, drainage) of the SDH 1370 through a lumen of the catheter 1362. In some embodiments, the suction may be one or more of continuous, dynamic, cyclical, and pulsatile. Pulsatile pressure may induce clot fatigue and fracture facilitating aspiration removal Other embodiments of SDH drainage and arterial embolization are shown and described with respect to FIGS. 14A-14F. FIGS. 14A-14F are schematic cross-sectional views of a head of subject corresponding to the steps of method 1000 and devices described herein. FIGS. 14A, 14C, and 14E are coronal cross-sectional views of a head of a subject. FIGS. 14B, 14D, and 14F are lateral views of a head of a subject.

FIG. 14A is a coronal cross-sectional view 1400 of a head including bone (e.g., skull) 1410, brain 1420, dura 1430, carotid artery 1440, middle meningeal artery (MMA) 1442, and intradural space 1450. The MMA 1442 may include the foramen spinous 1443 and middle cranial fossa 1445. As shown in FIG. 14A, a delivery catheter (e.g., sheath) 1460 may be disposed within the internal maxillary artery and a proximal portion of the MMA. A catheter 1462 (e.g., suction catheter, occlusion catheter) may be slidably disposed within a lumen of the delivery catheter 1460. The catheter 1462 may be advanced into the subdural space. In some embodiments, the shaft 1364 depicted in FIGS. 13A-13J may be withdrawn from the catheter to allow a second shaft 1464 (e.g., second RF device having a second electrode) including a linear tip configured to penetrate through a membrane of a subdural hematoma 1470. The second shaft 1464 may be slidably disposed within a lumen of the catheter 1462. The second shaft 1464 may be advanced from a distal end of the catheter 1462 to contact an outer layer (e.g., capsule, membrane) of the SDH 1470. Energy (e.g., RF energy) may be applied by the second shaft 1464 to perforate the membrane of the SDH 1470 and facilitate ingress of the second shaft 1464 and catheter 1462 into the SDH 1470. In some embodiments, the second shaft 1464 may have a linear distal end configured to deliver RF energy to form an opening in the SDH 1470. FIG. 14A further depicts embolic material 1480 previously delivered to blood vessels adjacent the SDH.

FIG. 14B is a lateral view 1401 of FIG. 14A where the catheter 1462 has been advanced into the SDH 1470 and the second shaft 1464 has been withdrawn. In FIG. 14B, suction 1472 is applied to remove the blood and fluid of the SDH 1470 through the lumen of the catheter 1462. Once the SDH 1470 has been drained (e.g., evacuated), the catheter 1462 may be withdrawn from the subdural space and into the MMA 1442.

In some embodiments, the opening formed in the MMA by a first shaft may be closed using a second shaft as the catheter and second shaft are withdrawn from the subdural space. FIG. 14C depicts coronal cross-sectional views 1402, 1403 of a head and a blood vessel, respectively. FIG. 14D depicts lateral views 1404, 1405 of a head and a blood vessel, respectively. In FIGS. 14C and 14D, the distal ends of each of the catheter 1462 and the second shaft 1464 are disposed within the MMA 1442. The second shaft 1464 may be extend out of the catheter 1462 at or proximal to the opening formed in the MMA 1442. In some embodiments, the second shaft 1464 may be configured to deliver RF energy to thermally coagulate (e.g., clot) the MMA in order to close the opening.

In some embodiments, the opening formed in the MMA by a shaft may be closed delivering embolic material using a catheter as the catheter is withdrawn from the subdural space. FIG. 14E depicts coronal cross-sectional views 1406, 1407 of a head and a blood vessel, respectively. FIG. 14F depicts lateral views 1408, 1409 of a head and a blood vessel, respectively. In FIGS. 14E and 14F, the catheter 1462 is disposed within the MMA 1442 and used to deliver embolic material (e.g., coil) 1482 into the MMA 1442 in order to close the opening formed in the wall of the MMA 1442 and/or occlude branch vessels of the MMA 1442. The catheter assembly (e.g., catheter 1462, delivery catheter 1460) may then be withdrawn from the subject.

In some embodiments, the embolic material may include one or more of a balloon, gel foam, collagen, thrombin, particles (e.g., polyvinyl alcohol, embospheres), coils (e.g., pushable, injectables, detachable), liquid agents (e.g., glue, ethylene vinyl alcohol), sclerosant agents (e.g., sodium teradecyl sulfate, alcohol, algel), plugs (e.g., including self-expandable cylindrical or hourglass shape), stitches, electrocoagulation, combinations thereof, and the like. In some embodiments, the embolic material may be configured to prevent accidental retreat during device retrieval such as a focal enlargement on the distal segment of the gel foam, collagen pledget, and flowering elements that radially expand after being unsheathed, hydrated, in contact with ions, and the like. In some embodiments, embolic material such as a coil may be transected at a predetermined length by one or more chemical, mechanical, and electrical mechanisms.

Figure 16:
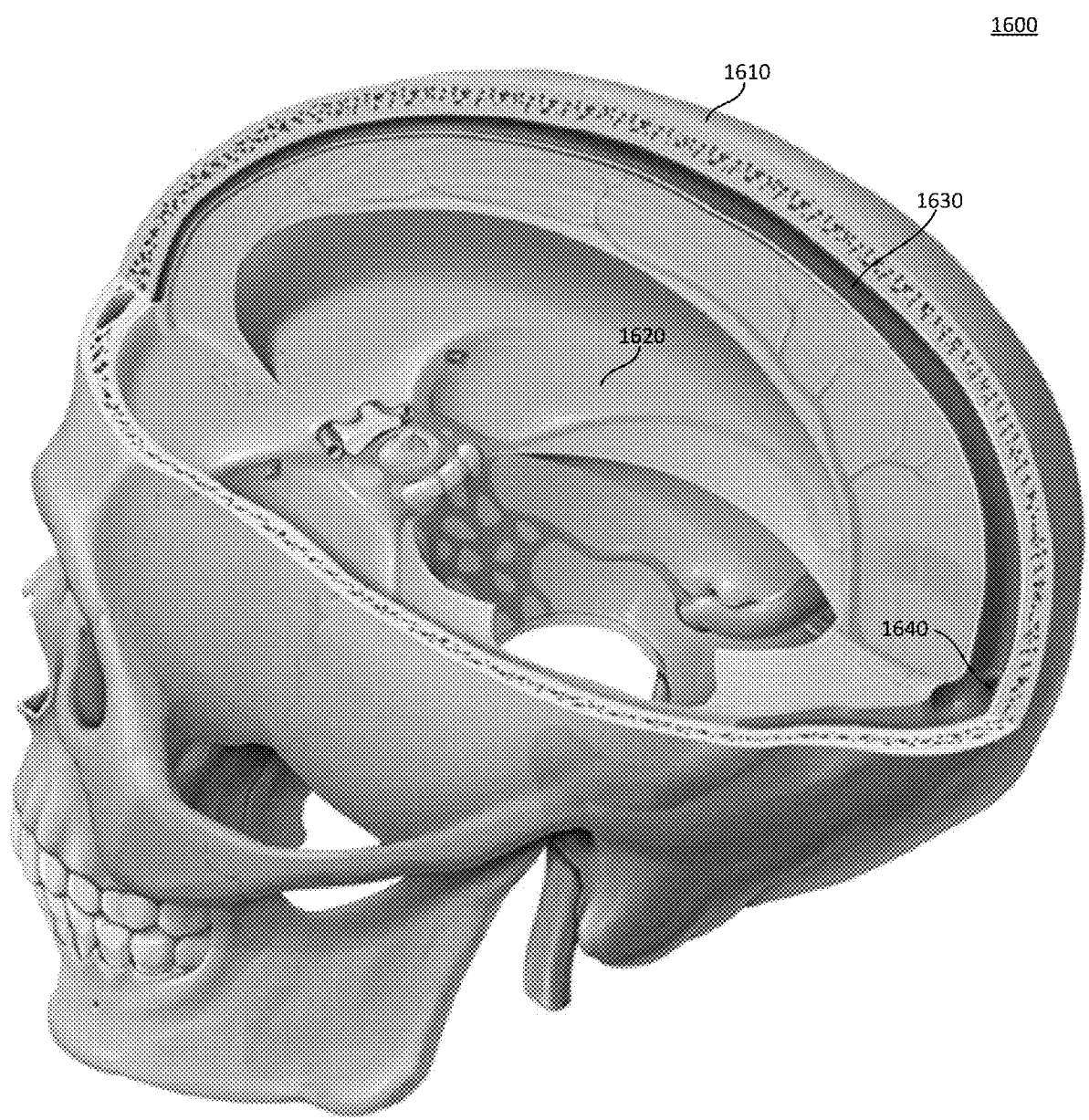
FIG. 16 is a perspective cut-away view of a head of a subject, according to embodiments.
Figures 17A, 17B, 17C:
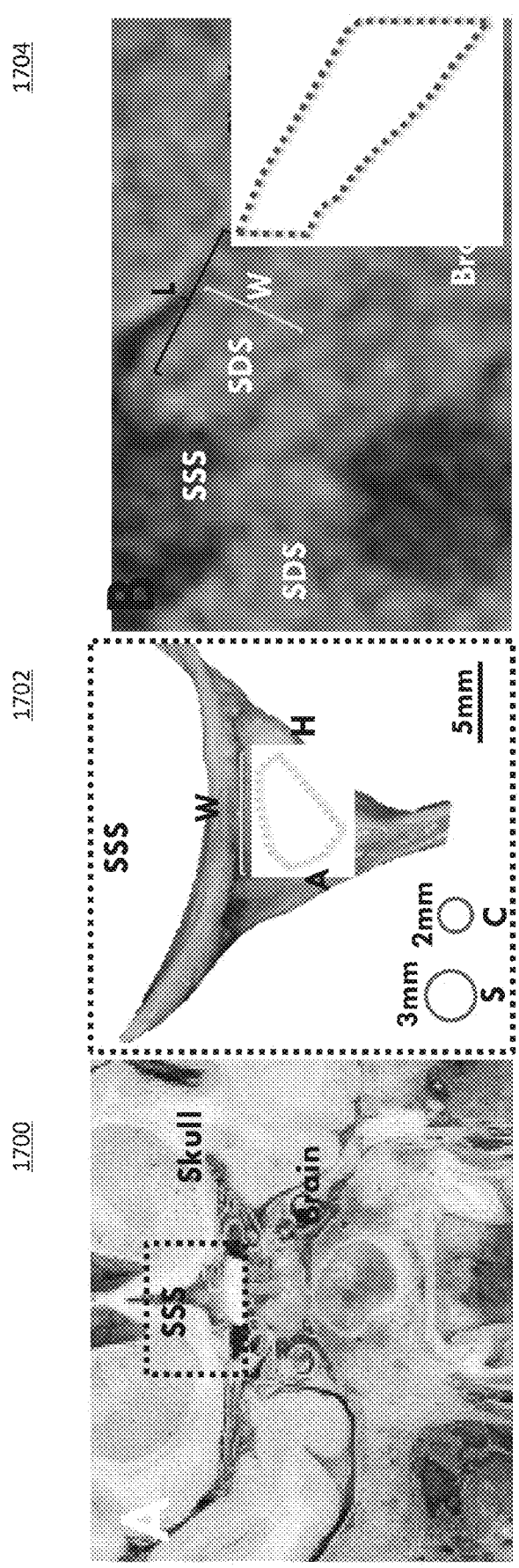
FIG. 17A is a cross-sectional image of a cadaveric head of a subject, according to embodiments.
FIG. 17B is an image of a superior sagittal sinus, according to embodiments.
FIG. 17C is an image of vascular anatomy, according to embodiments.
Figure 17D:
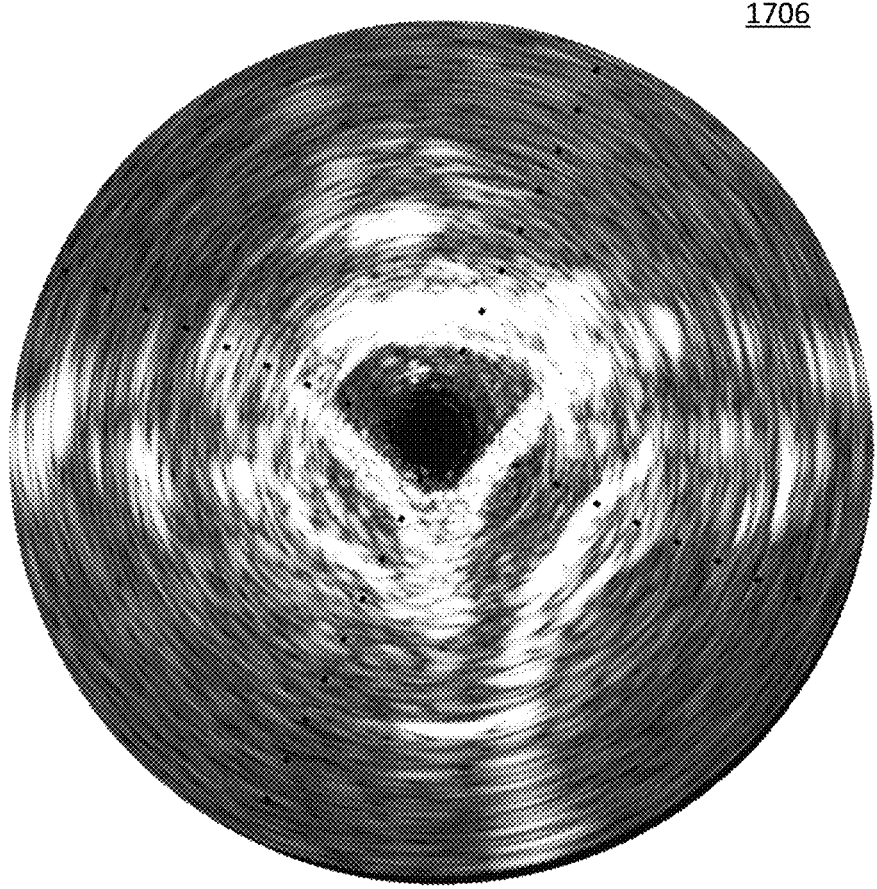
FIG. 17D is an ultrasound image of a superior sagittal sinus, according to embodiments.

Also described here are methods for accessing an extravascular intracranial space (e.g., supratentorial parasagittal intradural compartment) using a transvenous approach using the systems and devices described herein. It may be helpful to briefly identify and describe the relevant anatomy. The intradural compartment is composed of the subdural space, the subarachnoid space with their expansions (e.g., cisterns), the brain tissue, and the brain ventricles (e.g., fluid filled cavities inside the brain). The supratentorial compartment is considered the intracranial space above the tentorium, and the infratentorial compartment is considered the intracranial space above the tentorium. FIG. 16 is a perspective cut-away view 1600 of a head of a subject including a skull 1610, brain 1620, dura 1630, and a superior sagittal sinus 1640. FIG. 17A is a cross-sectional view 1700 of a head of a subject. FIG. 17B is a schematic diagram 1702 of a superior sagittal sinus. FIG. 17C is an axial cut of a computer tomography scan 1704 of a subject with a subdural hematoma. FIG. 17D is an ultrasound image 1706 of a superior sagittal sinus.

In some embodiments, the systems and devices described herein may be navigated into the dural venous sinuses (e.g., including the superior sagittal sinus and the superior petrosal sinus) from a peripheral venous approach, and create an opening through the venous wall and dura to the subdural space for access to the extravascular space.

For example, a delivery sheath can be navigated from a peripheral venous access into the jugular vein, the sigmoid and transverse sinuses and into the superior sagittal sinus. The sheath may be directed towards a lateral wall of the sinus ipsilateral. The shape of the SSS is generally triangular with the largest side being the base oriented against the skull. The delivery sheath may be disposed at the base of the triangle (e.g., the skull) and oriented towards the lateral wall of the sinus towards the subdural space. In some embodiments, the dural sinus wall may be penetrated by a shaft. Then, one or more devices may be navigated into the extravascular space, including a catheter configured to suction fluid (e.g., from a SDH). After completion of the intervention in the extravascular space, the device may be withdrawn and the opening closed using a hemostatic device as described herein. Accordingly, the methods may minimize blood extravasation while the passageway is patent, enable navigation within the intracranial compartment without brain perforation or damage, allow drainage of subdural collections (e.g., SDH), and facilitate durotomy closure upon the removal of the catheter assembly.

In some embodiments, one or more devices may be placed (e.g., implanted) in the extravascular space temporarily or permanently. For example, the devices may include one or more electrodes, sensors, transmitter, receivers, grids, ports, catheters, biopsy needles or punches, implantable chemotherapy wafers or radiation seeds, combinations thereof, and the like.

It should be understood that the devices, systems, and methods described herein are not exclusively for drainage of fluid, clots and particulate matter from the subdural space. Instead, the methods and systems described herein can be adapted to obtain safe access and drain fluid and clots in the epidural space, for example, such as for evacuation of acute epidural hematomas, cystic fluid and pus.

In addition, the methods and systems described herein can be adapted to obtain access to any intracranial target in the intradural compartment, including the subarachnoid space, the cisterns, the brain tissue and the brain ventricles. It should be understood that the methods and systems described herein can be adapted and used to obtain safe access to the subdural or epidural space and drain fluid, particulate matter and clots though veins, the dural venous sinuses and any other natural corridor. For example, the devices, systems, and methods described herein can be used to obtain safe and stable transvascular access to any extravascular space and then close the arteriotomy or venotomy site. It should also be understood that the methods and systems described herein can be adapted and used to obtain safe access to the intradural compartment in the spine.

Figure 20A:
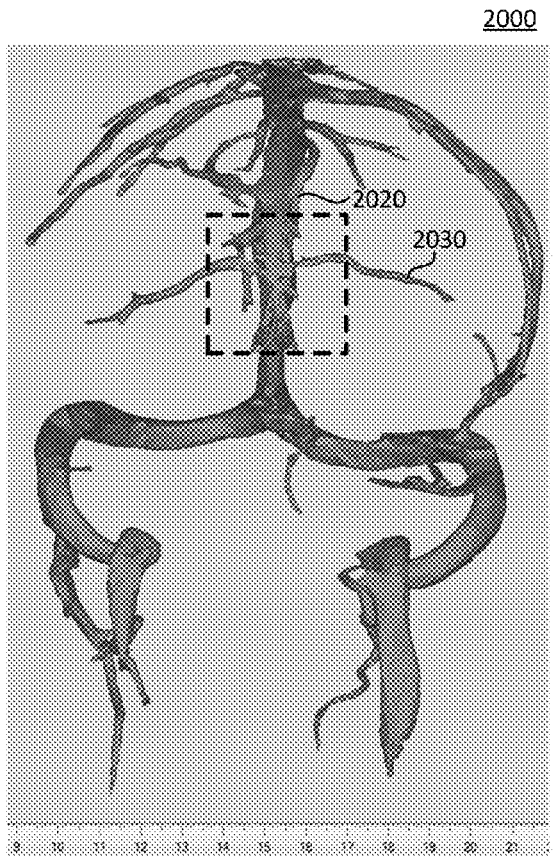
FIG. 20A is a three-dimensional image of a set of veins and dural sinuses in a head of a subject, according to embodiments.
Figure 21A:
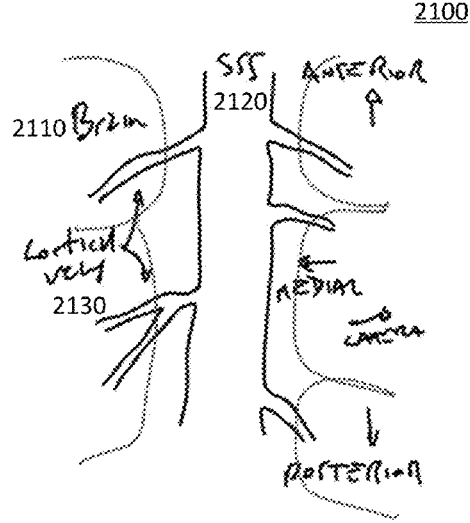
FIG. 21A is a schematic top view of a head of a subject, according to embodiments.

FIG. 20A is a three-dimensional image 2000 (e.g., reconstruction) of a set of veins and dural sinuses in a head of a subject including the superior sagittal sinus 2020 and cortical veins 2030 branching therefrom. FIG. 21A is a corresponding schematic diagram 2100 of a top view of cranial anatomy including a brain 2110, superior sagittal sinus 2120, and cortical veins 2130. The SSS 2120 runs along the midline and the cortical veins 2130 drain into the SSS 2120.

Figure 20B:
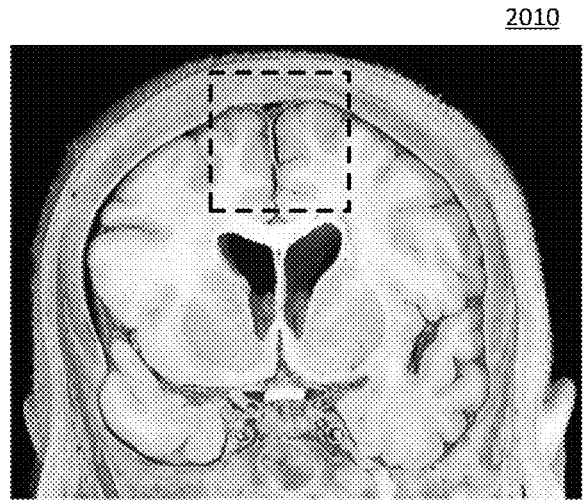
FIG. 20B is a coronal cross-sectional view of a head of a subject, according to embodiments.
Figure 21B:
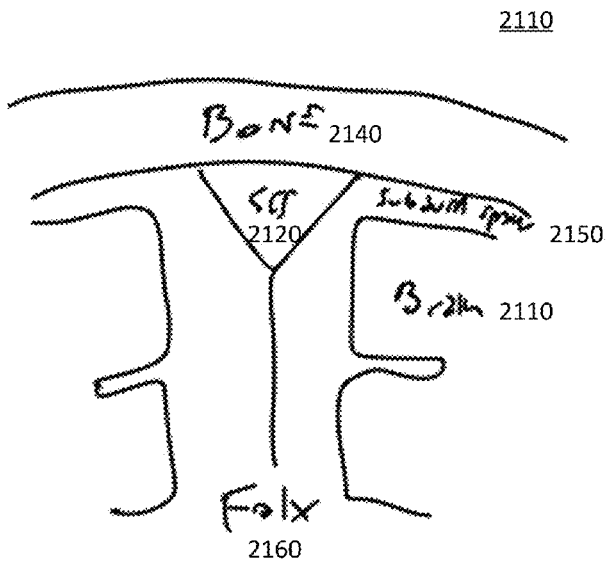
FIG. 21B is a schematic coronal cross-sectional view of a head of a subject, according to embodiments.

FIG. 20B is a coronal cross-sectional view 2010 of a head of a subject. FIG. 21B is a corresponding schematic diagram 2110 of a coronal cross-sectional view of cranial anatomy including the brain 2110, SSS 2120, bone 2140, subdural space 2150 (e.g., between brain 2110 and SSS 2120), and falx cerebri 2160.

Figure 22:
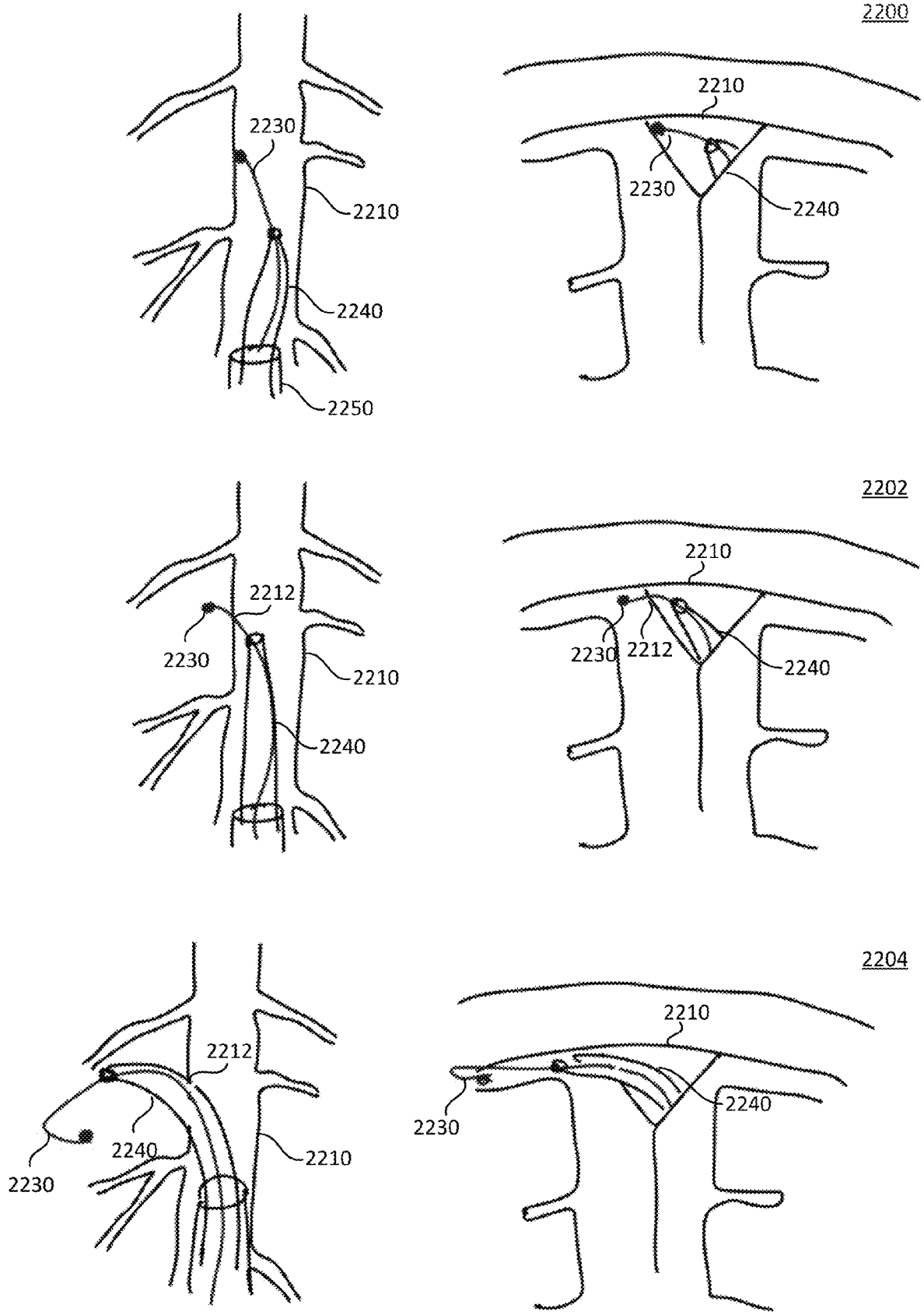
FIG. 22 are schematic top views and coronal cross-sectional views of a head of a subject, according to embodiments.

FIG. 22 are schematic top views and coronal cross-sectional views of a head of a subject having a catheter assembly as described herein. For example, a shaft 2230 and a catheter 2240 of a catheter assembly are disposed within the superior sagittal sinus 2210. A delivery catheter 2250 may be configured to navigate the catheter assembly into the SSS 2210. The shaft 2230 and catheter 2240 may include components that are structurally and/or functionally similar to the shaft and catheters described with respect to FIGS. 5-9. In some embodiments, the catheter 2240 may include a dilator having a tapered distal end having a distal opening. In some embodiments, a distal portion of the shaft 2230 may be formed of a memory shape material (e.g., nitinol) having a predetermined curve such that the distal portion of the shaft 2230 curves as it is advanced from a distal end of the catheter 2240. In some embodiments, the unconstrained curve of the shaft 2230 may be configured to contact a wall of the SSS 2210. As shown in the cross-sectional view of 2200, the curve of the shaft 2230 will accommodate the geometry of the generally triangular cross-sectional shape of the SSS 2210. For example, the extended shaft 2230 will generally accommodate (e.g., conform to, follow) the medial lateral projection of the SSS 2210, thereby providing consistent wall apposition. At 2202, energy (e.g., RF energy) may be delivered to the wall of the SSS 2210 and dura so as to create an opening (e.g., slit) 2212 through which the shaft 2230 advances through. At 2204, The shaft 2230 is further advanced through the subdural space and the catheter 2240 is advanced through the opening 2212. For example, the unconstrained shape of the shaft 2230 may form a J shape. Although not shown, the delivery catheter 2250 may be advanced over the catheter 2240 through the opening 2212. Thereafter, a medical procedure may be performed as described herein.

Figure 23:
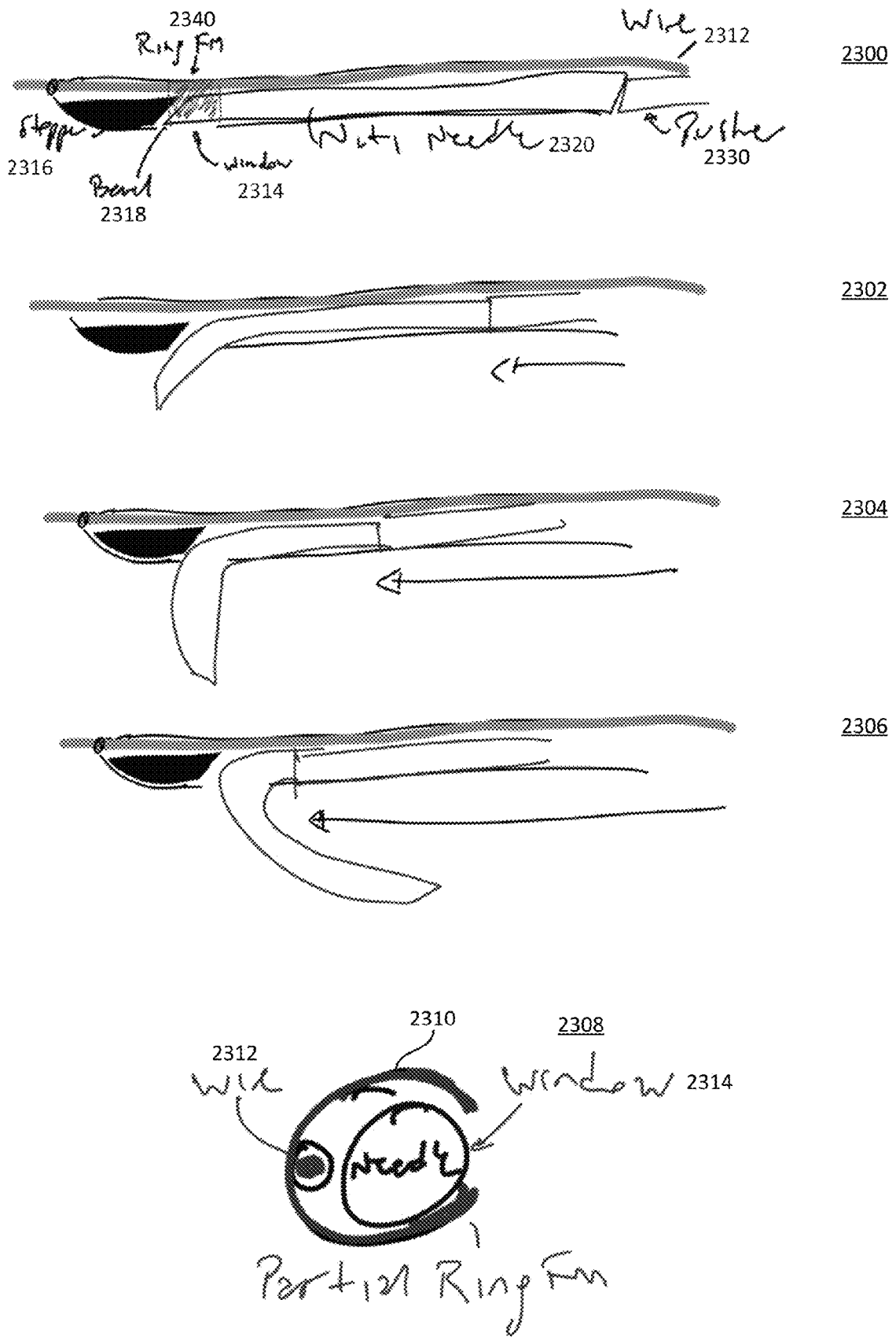
FIG. 23 are schematic side views and a cross-sectional view of a shaft, according to embodiments.

FIG. 23 are schematic cross-sectional side views 2300, 2302, 2304, 2306 and a cross-sectional view 2308 of a catheter 2310. In some embodiments, the catheter 2310 may include a wire 2312, a perforating element 2320 (e.g., nitinol needle), and a pusher 2330 configured to translate the perforating element 2320. A distal portion of the catheter may include a stopper 2316 having a bevel 2318 (e.g., tapered portion, bend, slope, angle) configured to direct the perforating element 2320 out of an opening (e.g., window) 2314 of the catheter 2310. The perforating element 2320 may be configured to be translated within and advanced out of the catheter 2310 using a pusher 2330 slidably disposed within the catheter 2310. The perforating element 2320 may include a cutting edge (e.g., blade, bevel, cutter). For example, once the perforating element 2320 contacts the bevel 2318 of the stopper 2316, the perforating element 2320 may curve out of the opening 2314 in a predetermined manner. In FIG. 23, the curvature of the perforating element 2320 increases as it is advanced out of the catheter 2310. In some embodiments, the predetermined curvature of the perforating element 2320 may determine a trajectory of the perforating element 2320 within the subdural space. This may facilitate, for example, delivery of a cortical implant to a predetermined portion of the brain.

In some embodiments, the catheter 2310 may include a ring-shaped fluoromarker configured to aid visualization and guide positioning of the catheter within a subject. For example, the ring-shaped fluoromarker 2340 may have a C-shape as shown in the cross-sectional view 2308. In particular, the fluoromarker 2340 may be disposed about the opening 2314 of the catheter 2310. In some embodiments, the stopper 2316 may comprise an ultrasound device (e.g., intravascular ultrasound)

Figure 24:
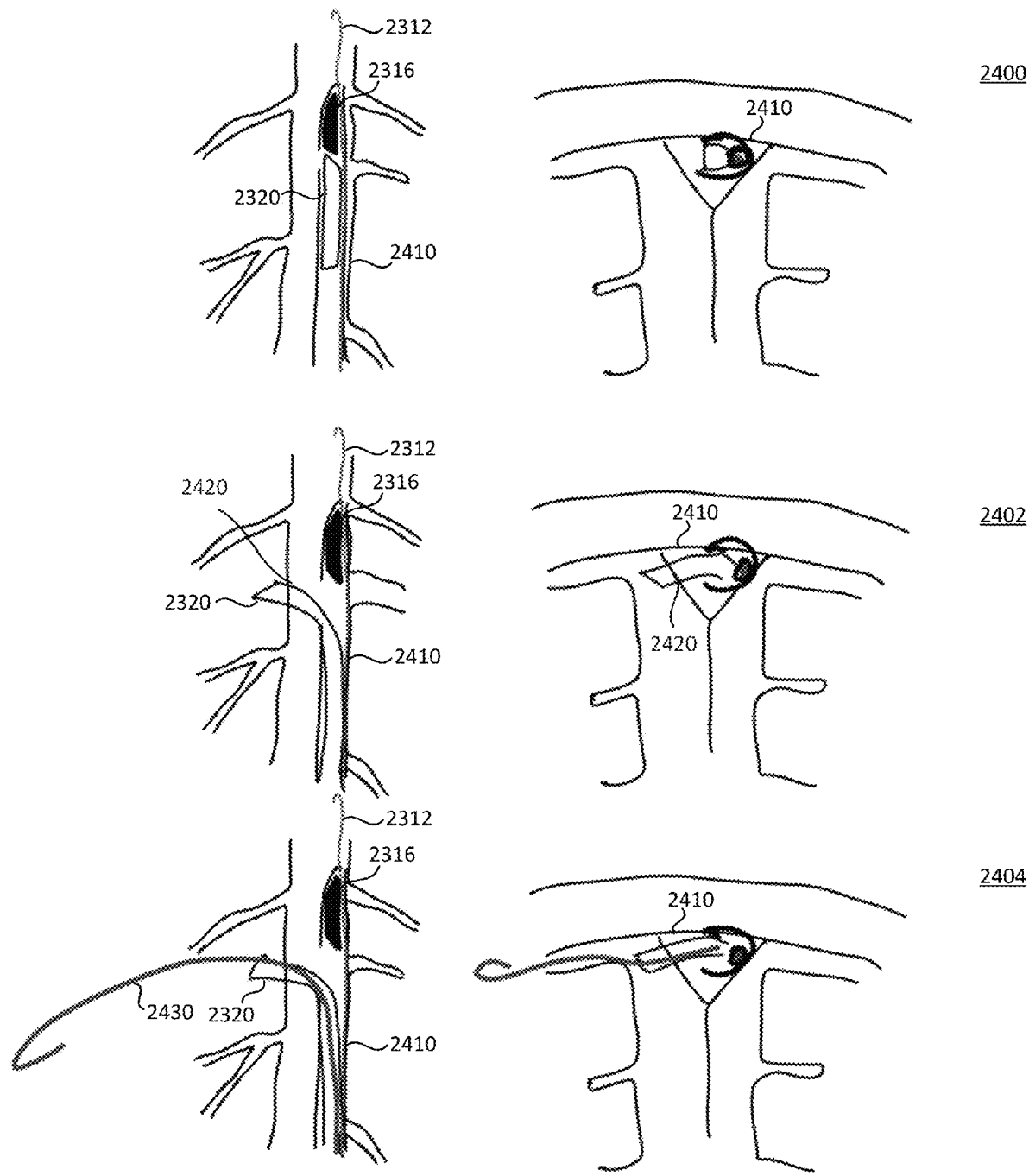
FIG. 24 are schematic top views and coronal cross-sectional views of a head of a subject, according to embodiments.

FIG. 24 are schematic top views and coronal cross-sectional views of a head of a subject having a catheter assembly as shown and described with respect to FIG. 23. The catheter 2310 may be disposed within a superior sagittal sinus 2410 of the subject. At 2400, the catheter 2310 may be guided via imaging (e.g., X-ray) within the SSS 2410 such that an opening 2420 formed by the catheter 2310 is not formed in a cortical vein. An opening 2314 of the catheter 2310 may be oriented towards the opening 2420 to be formed in the SSS 2410. The ring-shaped fluoromarker may be visualized within the SSS 2410 and used to determine an orientation of the opening 2314 within the SSS 2410.

At 2402, the perforating element 2320 may be advanced out of the catheter 2310 towards a wall of the SSS 22410 to form the opening 2420 in the SSS 2410. Due to the strength of the dura, while the perforating element 2320 contacts and advances through the wall of the SSS 2410 and dura, a counterforce is developed where the catheter 2310 is pushed against an opposing sidewall of the SSS 2410. In some embodiments, a length of a curved distal tip portion of the perforating element 2320 may be between about 15 mm and about 25 mm, including all ranges and sub-values in-between. At 2404, a shaft 2430 may be advanced from a lumen of the perforating element 2320 and into a subdural space to perform a medical procedure as described herein (e.g., drain a SDH, deliver an electrode).

Figure 25:
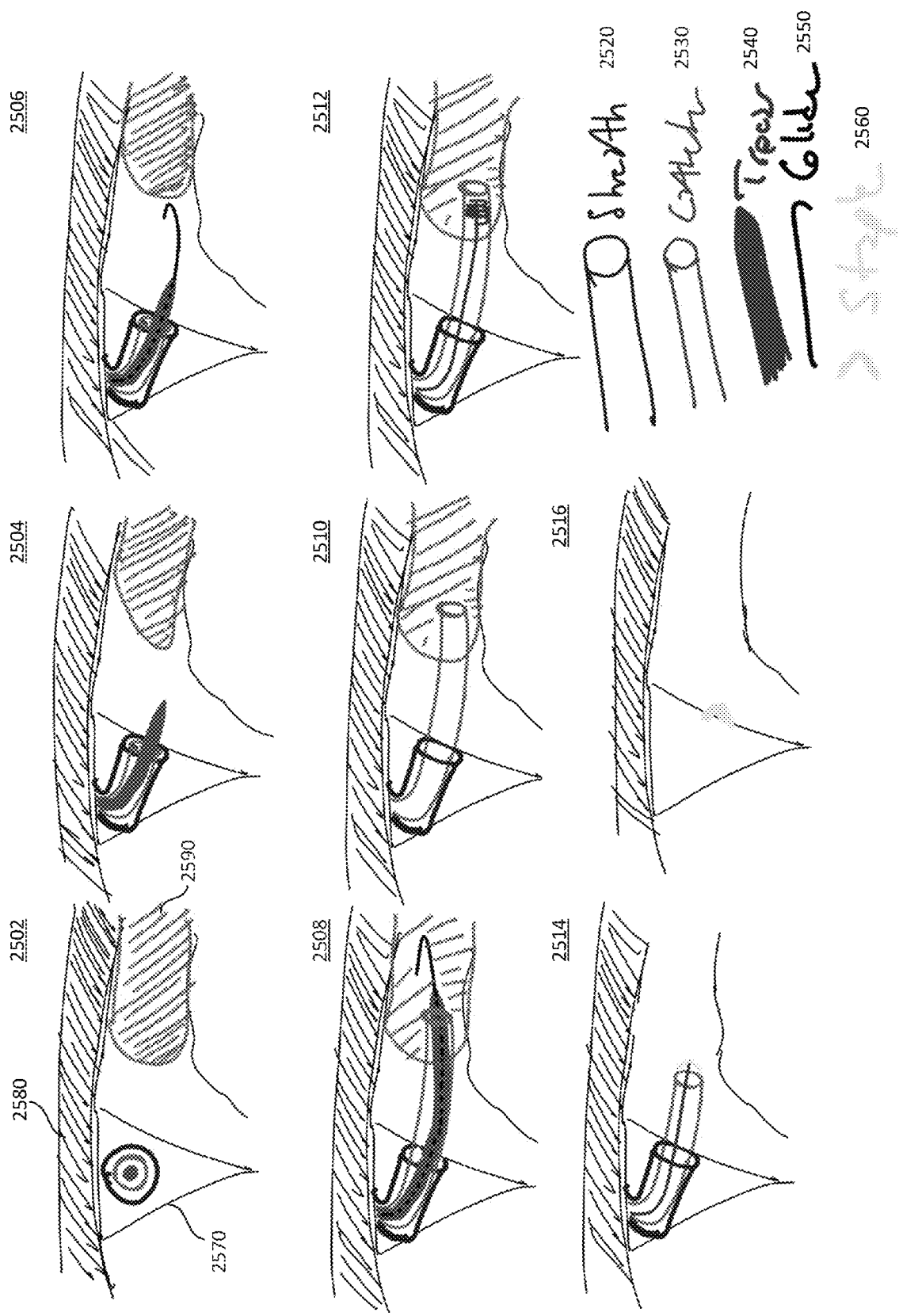
FIG. 25 are schematic coronal cross-sectional views of a head of a subject, according to embodiments.

FIG. 25 are schematic coronal cross-sectional views of a head of a subject. In some embodiments, a delivery catheter 2520 may be articulated using one or more of a pull wire or a push wire to direct a distal end of the catheter assembly towards a predetermined wall of an SSS 2570, as well as provide sufficient stiffness to provide a counterforce against the resistance of the SSS 2570 and dura as an opening is being created. That is, at 2502, the delivery catheter 2520 may be configured to be anchored against a wall of the SSS 2570. At 2504, a perforating element 2540 may be advanced through a wall of the SSS 2570 and dura to form an opening. At 2506, a guidewire 2550 may be advanced into the subdural space through a lumen of the perforating element 2540. At 2508, a catheter 2530 such as a dilator may be advanced into the subdural space over the perforating element 2540. One or more of the catheter 2530, perforating element 2540, and guidewire 2550 may be advanced into a subdural hematoma 2590. At 2510, the perforating element 2540 and guidewire 2550 are withdrawn to facilitate suction of the SDH 2590 through a lumen of the catheter 2530. At 2512, a device (e.g., coil) may be delivered into the subdural space using the catheter 2530. At 2514, a staple 2560 may be delivered using the catheter 2530. At 2516, the staple 2560 may be used to close the opening formed in the SSS 2570. However, if an implantable device (e.g., a catheter, a sensor, one or more wires, electrodes) remains through the transvascular passageway, a staple (or other closure device) may not be used.

Figure 26:
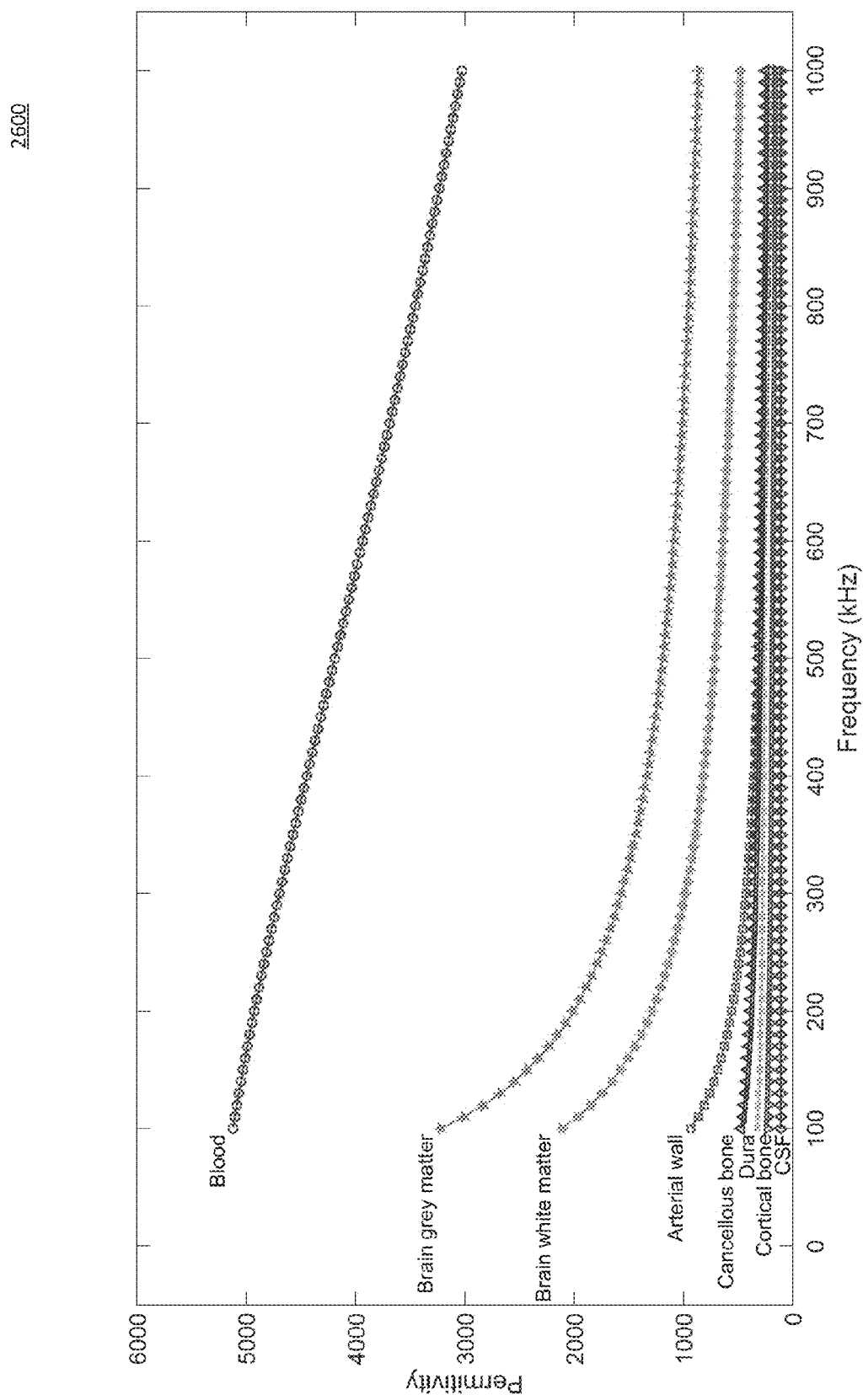
FIG. 26 is a plot of permittivity and frequency for a set of tissue types, according to embodiments.
Figure 27:
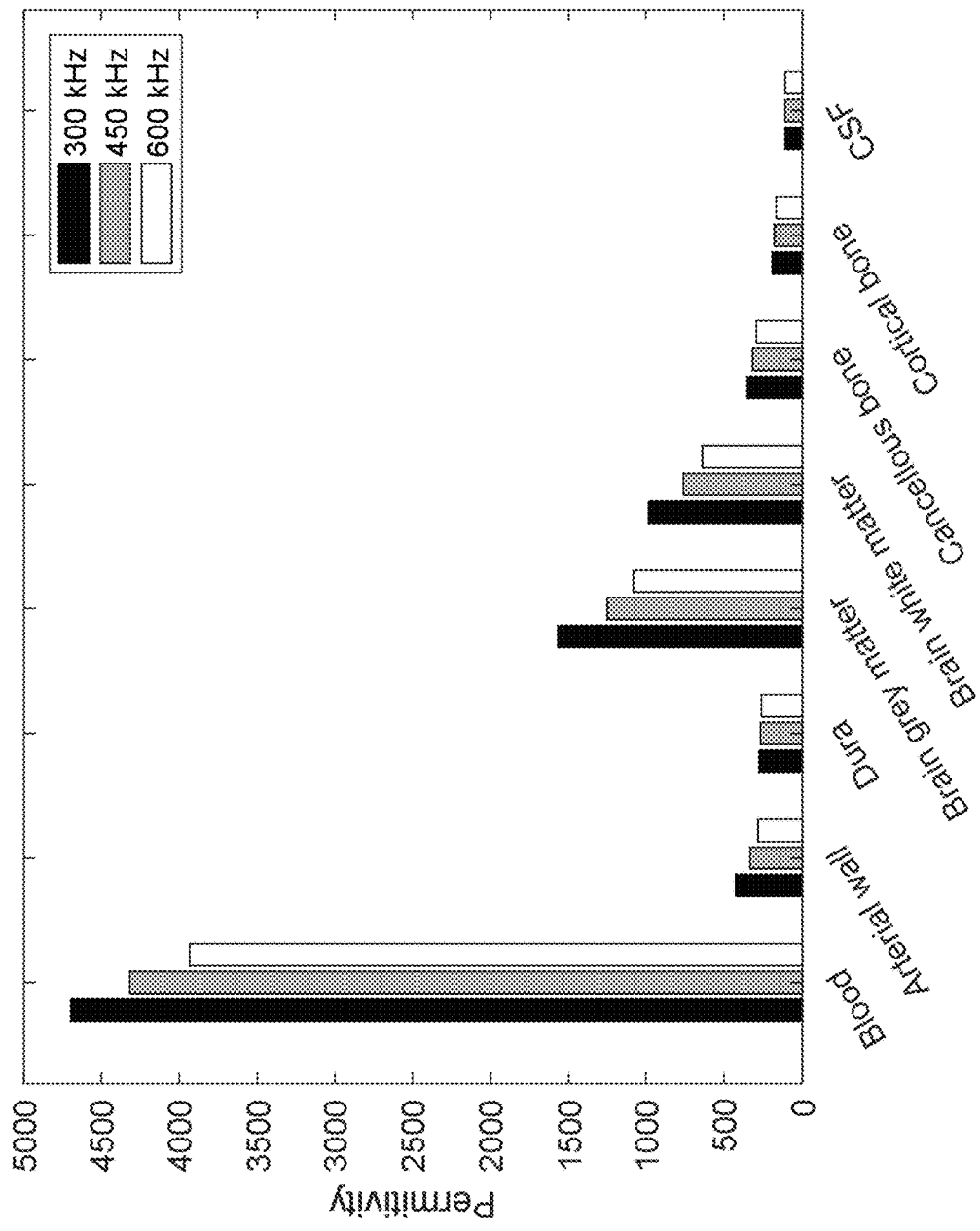
FIG. 27 is a plot of permittivity of a set of tissue types for a set of RF frequencies according to embodiments.

FIG. 26 is a plot of permittivity and frequency of a set of tissue types including blood, brain grey matter, brain white matter, arterial wall, cancellous bone, dura, cortical bone, and cerebrospinal fluid. The order of permittivity did not change for RF frequencies below 520 kHz. At higher frequencies, the descending order of permittivity is blood, brain grey matter, brain white matter, arterial wall or cancellous bone or dura, cortical bone, and cerebrospinal fluid. FIG. 27 is a plot of permittivity of a set of tissue types for a set of RF frequencies.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The specific examples and descriptions herein are exemplary in nature and embodiments may be developed by those skilled in the art based on the material taught herein without departing from the scope of the present invention.

The invention claimed is:

1. An apparatus for draining a subdural hematoma disposed in an intracranial extravascular space of a patient, the apparatus comprising:
 a suction catheter disposable within an intracranial vessel of the patient, the suction catheter defining a lumen; and
 a shaft configured to be advanced through the lumen of the suction catheter until a distal tip portion of the shaft is disposed within the intracranial vessel, the shaft including:
  (1) a perforating element disposed at a distal end of the distal tip portion of the shaft, the perforating element configured to cut through a wall of the intracranial vessel and dura of the patient to create a longitudinal slit that functions as a passageway from the intracranial vessel lumen to the intracranial extravascular space;
  (2) a preset curved section of the shaft configured to be constrained to a substantially straight configuration when disposed within the lumen of the catheter and to curve toward the wall of the intracranial vessel upon exiting the lumen of the catheter, the preset curved section further configured to transition to a curved configuration in response to the perforating element puncturing through the wall of the intracranial vessel and the dura and to cause the perforating element to follow an arc that forms the longitudinal slit in the wall of the intracranial vessel and the dura; and (3) a wider section of the shaft disposed proximal to the preset curved section, the wider section having an outer diameter substantially equal to an inner diameter of the suction catheter to prevent ovalization of the suction catheter, the suction catheter configured to be advanced through the longitudinal slit and to the subdural hematoma to allow fluid or matter from the subdural hematoma to be transvascularly drained out of the intracranial extravascular space via the lumen of the catheter.

2. The apparatus of claim 1, wherein the suction catheter includes a proximal end that is configured to be coupled to a suction source such that the suction source can apply suction to the lumen to drain the fluid or the matter from the subdural hematoma.

3. The apparatus of claim 1, wherein the preset curved section has a J-shape or a U-shape in the curved configuration.

4. The apparatus of claim 1, wherein the perforating element has an atraumatic shape.

5. The apparatus of claim 1, wherein the perforating element is configured to generate radiofrequency (RF) energy to cut through the wall of the intracranial vessel and the dura.

6. The apparatus of claim 1, wherein the shaft further includes an offset configured to orient the perforating element in a direction toward the wall of the intracranial vessel and the dura while a proximal portion of the shaft faces a skull of the patient.

7. The apparatus of claim 6, wherein the offset has a non-circular cross-sectional shape configured to preferentially bend in a first plane over a second plane.

8. The apparatus of claim 1, wherein a distal end of the suction catheter includes a first radiopaque element, and the shaft includes a second radiopaque element disposed near the wider section, such that the wider section can be aligned with the distal end of the suction catheter prior to advancing the suction catheter through the longitudinal slit.

9. The apparatus of claim 1, wherein the shaft includes a first radiopaque element disposed at the perforating element and a second radiopaque element disposed proximal of the curved section, the first and second radiopaque elements configured to facilitate confirmation of a configuration of the curved section.

10. The apparatus of claim 9, wherein, when the curved section is in the curved configuration, the perforating element and the first radiopaque element forms an angle with respect to the second radiopaque element of between about 5° and about 15°.

11. The apparatus of claim 1, wherein the shaft further includes a proximal section having an outer diameter that varies along a length of the proximal section.

12. The apparatus of claim 11, wherein the proximal section tapers from a first outer diameter to a second outer diameter for a length of between about 4 mm and about 6 mm.

13. The apparatus of claim 12, wherein the first outer diameter of the proximal section of shaft is substantially equal to an inner diameter of the suction catheter to restrict a length that the shaft advances distally beyond a distal end of the suction catheter.

14. An apparatus for draining a subdural hematoma disposed in an intracranial extravascular space of a patient, the apparatus comprising:

a suction catheter having a working length of at least 120 cm and including a distal portion having an inner diameter of up to about 0.060 inches such that the distal portion of the suction catheter is disposable within a middle meningeal artery (MMA) of the patient, the suction catheter defining a lumen; and a shaft configured to be advanced through the lumen of the suction catheter until a distal tip portion of the shaft is disposed within the MMA, the shaft including:

a perforating element disposed at a distal end of the distal tip portion, the perforating element configured to cut through a wall of the MMA and dura of the patient to create a passageway from the MMA into the intracranial extravascular space, the perforating element configured to be angled with respect to the distal tip portion such that, when the perforating element is disposed distally beyond the distal end of the suction catheter, the perforating element can be directed toward the wall of the MMA and the dura and cut through the wall of the MMA and the dura at an oblique angle, the shaft is configured to be advanced within the intracranial extravascular space to the subdural hematoma, and the suction catheter configured to be advanced over the shaft such that the suction catheter is guided by the shaft through the passageway and to the subdural hematoma to allow fluid or matter from the subdural hematoma to be transvascularly drained out of the intracranial extravascular space via the lumen of the catheter.

15. The apparatus of claim 14, wherein the perforating element forms an angle of between about 1° and about 90° with respect to the distal tip portion when the perforating element is disposed distally beyond the distal end of the suction catheter.

16. The apparatus of claim 14, wherein the suction catheter includes a proximal end that is configured to be coupled to a suction source such that the suction source can apply suction to the lumen to drain the fluid or the matter from the subdural hematoma.

17. The apparatus of claim 14, wherein the perforating element has an atraumatic shape.

18. The apparatus of claim 14, wherein the shaft further includes an offset configured to orient the perforating element in a direction toward the wall of the MMA and the dura while a proximal portion of the shaft faces a skull of the patient.

19. The apparatus of claim 14, wherein the shaft further includes a wider section having a lateral dimension that is equal to or substantially equal to an inner diameter of the lumen of the suction catheter to prevent ovalizing of the suction catheter as the suction catheter is advanced through the longitudinal slit.

20. The apparatus of claim 14, wherein the shaft further includes a proximal section having an outer diameter that tapers from a first outer diameter substantially equal to an inner diameter of the suction catheter to a second outer diameter, such that the proximal section is configured to restrict a length that the shaft can advance distally beyond the distal end of the suction catheter.

21. An apparatus for draining a subdural hematoma disposed in an intracranial extravascular space of a patient, the apparatus comprising:

a suction catheter disposable within an intracranial vessel of the patient, the suction catheter defining a lumen; and a shaft configured to be advanced through the lumen of the suction catheter until a distal tip portion of the shaft is disposed within the intracranial vessel, the shaft including:
  (1) a perforating element disposed at a distal end of the distal tip portion of the shaft, the perforating element configured to cut through a wall of the intracranial vessel and a dura of the patient to create a passageway from the intracranial vessel into the intracranial extravascular space;
  (2) a curved section of the shaft having a preset curvature, the curved section configured to be radially constrained within the lumen of the suction catheter and to curve toward the wall of the intracranial vessel and the dura upon exiting the lumen of the catheter; and
  (3) a partial helix or twist of the shaft disposed proximal of the curved section, the partial helix or twist configured to orient the preset curvature of the curved section to follow a curvature of the intracranial vessel as the shaft is advanced through the lumen of the suction catheter, the suction catheter configured to be advanced through the passageway and to the subdural hematoma to allow fluid or matter from the subdural hematoma to be transvascularly drained out of the intracranial extravascular space via the lumen of the catheter.

22. The apparatus of claim 21, wherein the shaft further includes a bend at a location between the perforating element and the curved section.

23. The apparatus of claim 22, wherein the bend is configured to direct the perforating element toward the wall of the intracranial vessel and the dura.

24. The apparatus of claim 22, wherein the preset curvature of the curved section has a first radius of curvature, and the bend has a second radius of curvature that is smaller than the first radius of curvature.

25. The apparatus of claim 21, wherein the curved section is first curved section that includes a convex curvature, and the shaft further includes a second curved section proximal of the first curved section, the second curved section including a concave curvature.

* * * * *